(12) United States Patent
Bambury et al.

(10) Patent No.: US 10,028,733 B2
(45) Date of Patent: Jul. 24, 2018

(54) FISTULA TREATMENT DEVICE

(71) Applicant: National University of Ireland, Galway, Galway (IE)

(72) Inventors: Eoin Bambury, Galway (IE); Moshe Zilversmit, Campbell, CA (US)

(73) Assignee: National University of Ireland, Galway, Galway (IE)

( * ) Notice: Subject to any disclaimer, the term of this patent is extended or adjusted under 35 U.S.C. 154(b) by 0 days.

(21) Appl. No.: 15/595,619

(22) Filed: May 15, 2017

(65) Prior Publication Data

US 2017/0311937 A1 Nov. 2, 2017

Related U.S. Application Data

(63) Continuation-in-part of application No. PCT/EP2016/061944, filed on May 26, 2016.

(30) Foreign Application Priority Data

| May 28, 2015 | (EP) | ................................ | 15169640 |
| Jun. 17, 2016 | (EP) | ................................ | 16174951 |
| Nov. 29, 2016 | (EP) | ................................ | 16201270 |

(51) Int. Cl.
*A61B 17/08* (2006.01)
*A61B 17/00* (2006.01)
*A61B 17/04* (2006.01)

(52) U.S. Cl.
CPC ...... *A61B 17/0057* (2013.01); *A61B 17/0401* (2013.01); *A61B 17/08* (2013.01); *A61B 2017/00641* (2013.01); *A61B 2017/0464* (2013.01)

(58) Field of Classification Search
CPC ...... A61B 17/0057; A61B 2017/00641; A61B 2017/0649
USPC ........................................................ 606/213
See application file for complete search history.

(56) References Cited

U.S. PATENT DOCUMENTS

| 4,204,541 | A | 5/1980 | Kapitanov |
| 4,745,919 | A | 5/1988 | Bundy et al. |
| 5,108,420 | A | 4/1992 | Marks |
| 5,309,927 | A | 5/1994 | Welch |
| 5,330,503 | A | 7/1994 | Yoon |
| 5,476,505 | A | 12/1995 | Limon |
| 5,582,616 | A | 12/1996 | Bolduc et al. |
| 5,628,762 | A | 5/1997 | Al-Tameem |

(Continued)

FOREIGN PATENT DOCUMENTS

| WO | WO 2007/090150 A2 | 8/2007 |
| WO | WO 2013/005752 A1 | 1/2013 |
| WO | WO 2014/117087 | 7/2014 |

OTHER PUBLICATIONS

Absorv®—Bioabsorbable Extrusions, http://www.zeusinc.com/advanced-products/asorv-bioabsorbable. Aug. 11, 2017 (7 pages).

(Continued)

*Primary Examiner* — Diane Yabut
*Assistant Examiner* — Martin T Ton
(74) *Attorney, Agent, or Firm* — Bookoff McAndrews, PLLC

(57) ABSTRACT

A fistula treatment system comprises a guide such as a guide coil 1101 which is adapted to extend partially around a tissue tract and an implant element 1102. The implant element 1102 is activated to draw tissue surrounding the tract inwardly.

30 Claims, 58 Drawing Sheets

(56) References Cited

U.S. PATENT DOCUMENTS

| | | | |
|---|---|---|---|
| 5,643,305 A | 7/1997 | Al-Tameem | |
| 5,645,565 A | 7/1997 | Rudd et al. | |
| 5,782,844 A | 7/1998 | Yoon et al. | |
| 5,810,851 A * | 9/1998 | Yoon | A61B 17/06 606/139 |
| 5,810,882 A | 9/1998 | Bolduc et al. | |
| 5,824,008 A | 10/1998 | Bolduc et al. | |
| 5,904,696 A | 5/1999 | Rosenman | |
| 5,964,772 A | 10/1999 | Bolduc et al. | |
| 5,972,001 A | 10/1999 | Yoon | |
| 6,010,517 A | 1/2000 | Baccaro | |
| 6,059,825 A | 5/2000 | Hobbs et al. | |
| 6,080,182 A | 6/2000 | Shaw et al. | |
| 6,245,079 B1 | 6/2001 | Nobles et al. | |
| 6,296,656 B1 | 10/2001 | Bolduc et al. | |
| 6,375,671 B1 | 4/2002 | Kobayashi et al. | |
| 6,537,300 B2 | 3/2003 | Girton | |
| 6,551,319 B2 | 4/2003 | Lieberman | |
| 6,562,051 B1 | 5/2003 | Bolduc et al. | |
| 6,663,633 B1 | 12/2003 | Pierson, III | |
| 6,790,218 B2 | 9/2004 | Jayaraman | |
| 6,884,248 B2 | 4/2005 | Bolduc et al. | |
| 7,077,850 B2 | 7/2006 | Kortenbach | |
| 7,115,274 B2 | 10/2006 | Keller et al. | |
| 7,189,251 B2 | 3/2007 | Kay | |
| 7,485,087 B2 | 2/2009 | Burgard | |
| 7,645,229 B2 | 1/2010 | Armstrong | |
| 7,811,295 B2 | 10/2010 | Kortenbach | |
| D629,899 S | 12/2010 | Meinero | |
| 7,897,167 B2 | 3/2011 | Armstrong et al. | |
| 8,177,809 B2 | 5/2012 | Mavani et al. | |
| 8,206,416 B2 | 6/2012 | Mavani et al. | |
| 8,221,451 B2 | 7/2012 | Mavani et al. | |
| 8,377,094 B2 | 2/2013 | Mavani et al. | |
| 8,414,634 B2 * | 4/2013 | Sekido | A61B 17/12022 623/1.11 |
| 8,465,516 B2 | 6/2013 | Pavcnik et al. | |
| 8,486,155 B2 | 7/2013 | McAlister et al. | |
| 8,491,256 B2 | 7/2013 | Cronin et al. | |
| 8,501,217 B2 | 8/2013 | Armstrong et al. | |
| 8,535,349 B2 | 9/2013 | Chen et al. | |
| 8,556,930 B2 | 10/2013 | Ellingwood | |
| 8,568,446 B2 | 10/2013 | Kurokawa et al. | |
| 8,579,919 B2 | 11/2013 | Bolduc et al. | |
| 8,647,351 B2 | 2/2014 | Kortenbach | |
| 8,685,072 B2 | 4/2014 | Neuberger | |
| 8,702,644 B2 | 4/2014 | Hall et al. | |
| 8,764,791 B2 | 7/2014 | Armstrong | |
| 8,784,436 B2 | 7/2014 | Ho et al. | |
| 8,840,917 B2 | 9/2014 | Armstrong et al. | |
| 8,858,546 B2 | 10/2014 | Hall et al. | |
| 8,915,941 B2 | 12/2014 | Obermiller | |
| 8,936,616 B2 | 1/2015 | Nelson | |
| 8,986,331 B2 | 3/2015 | Chekan et al. | |
| 9,113,851 B2 | 8/2015 | Agnew | |
| 9,131,941 B2 | 9/2015 | Carrison et al. | |
| 9,138,210 B2 | 9/2015 | Schulte et al. | |
| 9,149,262 B2 | 10/2015 | Obermiller et al. | |
| 8,932,325 B2 | 11/2015 | Stanley et al. | |
| 9,211,116 B2 | 12/2015 | Carrison et al. | |
| 9,226,736 B2 | 1/2016 | Obermiller et al. | |
| 9,277,904 B2 | 3/2016 | Paul, Jr. et al. | |
| 9,345,476 B2 | 5/2016 | Surti | |
| 9,433,410 B2 | 9/2016 | Kortenbach | |
| 9,456,813 B2 | 10/2016 | Obermiller et al. | |
| 9,456,815 B2 | 10/2016 | Armstrong et al. | |
| 9,474,514 B2 | 10/2016 | Agnew et al. | |
| 9,492,149 B2 | 11/2016 | Obermiller et al. | |
| 9,526,484 B2 | 12/2016 | Armstrong | |
| 9,532,773 B2 | 1/2017 | Jimenez et al. | |
| 9,538,996 B2 | 1/2017 | Patel et al. | |
| 2002/0183786 A1 | 12/2002 | Girton | |
| 2002/0193808 A1 | 12/2002 | Belef et al. | |
| 2004/0069312 A1 | 4/2004 | Ohmi | |
| 2004/0147957 A1 | 7/2004 | Pierson, III | |
| 2004/0193217 A1 | 9/2004 | Lubbers et al. | |
| 2005/0038460 A1 | 2/2005 | Jayaraman | |
| 2005/0049626 A1 | 3/2005 | Burgard | |
| 2005/0159776 A1 | 7/2005 | Armstrong | |
| 2005/0182495 A1 | 8/2005 | Perrone | |
| 2005/0187568 A1 | 8/2005 | Klenk et al. | |
| 2005/0251201 A1 | 11/2005 | Roue et al. | |
| 2006/0074447 A2 | 4/2006 | Armstrong | |
| 2006/0280720 A1 * | 12/2006 | Fitz | A61L 24/046 424/78.27 |
| 2007/0083230 A1 | 4/2007 | Javois | |
| 2007/0088445 A1 | 4/2007 | Patel et al. | |
| 2007/0129757 A1 | 6/2007 | Armstrong | |
| 2007/0179507 A1 | 8/2007 | Shah | |
| 2007/0198059 A1 | 8/2007 | Patel et al. | |
| 2007/0248601 A1 | 10/2007 | Karabey et al. | |
| 2008/0004657 A1 | 1/2008 | Obermiller et al. | |
| 2008/0051831 A1 * | 2/2008 | Deal | A61B 17/0057 606/213 |
| 2008/0097523 A1 | 4/2008 | Bolduc et al. | |
| 2008/0215076 A1 | 9/2008 | Baker | |
| 2008/0245374 A1 | 10/2008 | Agnew | |
| 2008/0275402 A1 | 11/2008 | Schnell | |
| 2009/0069843 A1 | 3/2009 | Agnew | |
| 2009/0112238 A1 | 4/2009 | Pitts et al. | |
| 2009/0326577 A1 | 12/2009 | Johnson et al. | |
| 2010/0049246 A1 | 2/2010 | Obermiller et al. | |
| 2010/0076463 A1 * | 3/2010 | Mavani | A61B 17/0057 606/151 |
| 2010/0082056 A1 | 4/2010 | Mavani et al. | |
| 2010/0249830 A1 | 9/2010 | Nelson | |
| 2010/0274266 A1 | 10/2010 | Rimer et al. | |
| 2011/0046607 A1 | 2/2011 | Halevy | |
| 2011/0054413 A1 | 3/2011 | Romhild et al. | |
| 2011/0054492 A1 | 3/2011 | Clark | |
| 2011/0054520 A1 | 3/2011 | Deal et al. | |
| 2011/0060362 A1 | 3/2011 | Patel et al. | |
| 2011/0238088 A1 | 9/2011 | Bolduc et al. | |
| 2011/0282334 A1 | 11/2011 | Groenhoff | |
| 2011/0282368 A1 | 11/2011 | Swayze et al. | |
| 2011/0282381 A1 | 11/2011 | Cronin et al. | |
| 2011/0295282 A1 | 12/2011 | Glick et al. | |
| 2012/0035644 A1 | 2/2012 | Eskaros et al. | |
| 2012/0046690 A1 | 2/2012 | Blom | |
| 2012/0323271 A1 | 12/2012 | Obermiller et al. | |
| 2013/0158595 A1 | 6/2013 | Mavani et al. | |
| 2013/0237816 A1 | 9/2013 | Armstrong | |
| 2013/0338706 A1 | 12/2013 | Jimenez et al. | |
| 2014/0018850 A1 | 1/2014 | Ellingwood | |
| 2014/0200604 A1 | 7/2014 | Carrison et al. | |
| 2014/0227337 A1 | 8/2014 | Keighley | |
| 2014/0243794 A1 | 8/2014 | Halskov et al. | |
| 2014/0257376 A1 | 9/2014 | Armstrong | |
| 2014/0277116 A1 | 9/2014 | Stanley et al. | |
| 2014/0288491 A1 | 9/2014 | Halskov et al. | |
| 2014/0303603 A1 | 10/2014 | Kullas et al. | |
| 2014/0379025 A1 | 12/2014 | Carrison et al. | |
| 2014/0379026 A1 | 12/2014 | Carrison et al. | |
| 2015/0045612 A1 | 2/2015 | Ostrovsky et al. | |
| 2015/0073471 A1 | 3/2015 | Clark | |
| 2015/0230802 A1 | 8/2015 | Lagodzki et al. | |
| 2015/0250460 A1 | 9/2015 | Horeman et al. | |
| 2015/0297807 A1 | 10/2015 | Leblanc et al. | |
| 2016/0000416 A1 | 1/2016 | Carrison et al. | |
| 2016/0000507 A1 | 1/2016 | Neuberger | |
| 2016/0007978 A1 | 1/2016 | Obermiller et al. | |
| 2016/0038128 A1 | 2/2016 | Carrison | |
| 2016/0143656 A1 | 5/2016 | Tasci | |
| 2016/0157840 A1 | 6/2016 | Carrison et al. | |
| 2016/0166380 A1 | 6/2016 | Seguin et al. | |
| 2016/0184069 A1 | 6/2016 | Lv et al. | |
| 2016/0262737 A1 | 9/2016 | Paul et al. | |

OTHER PUBLICATIONS

Chew, J., "Relieving that pain in the butt (Straits Times, Mind Your Body)," Singapore General Hospital, Mar. 21, 2013, 3 pages, http://www.sgh.com.sg/.

(56) References Cited

OTHER PUBLICATIONS

Dudukgain, H. et al., "Why do we have so much trouble treating anal fistula," World Journal of Gastroenterology, Jul. 28, 2011, vol. 17, Issue 28, pp. 3292-3296, http://wjgnet.com/1007-9327office.
Lewis, R. et al., "Novel biological strategies in the management of anal fistula," Colorectal Disease, The Association of Coloproctology of Great Britain and Ireland, Aug. 10, 2012, pp. 1445-1455.
Parks, A.G., et al. "A classification of fistula-in-ano," The British Journal of Surgery, Jan. 1976, vol. 63, No. 1, pp. 1-12.
Vasilevsky, M.D, CA et al., "The Incidence of Recurrent Abscesses or Fistula-in-ano Following Anorectal Suppuration," Diseases of the Colon & Rectum, 1984; Issue 27, pp. 126-130.
"Our purpose is to advance innovation in surgery," last updated Aug. 14, 2017, 2 pages, www.ethicon.com/healthcare-professionals/products.
Wilhelm, Dr. A, "FILAC Fistula-tract Laser Closure," 3 pages.
Villanueva-Herrero, Dr. Juan Antonio "Silicone disk to seal & Collagen matrices to heal Fistula Tracts," 2 pages, http://mintcare.sg/product_category/curaseal/.
"Peramacol™ Collagen Paste for Anorectal Fistula Repair" 4 pages, http://www.hungaronotes.hu/minden/notes2016/kiallitok/covidien2.pdf, 2013 Covidien 5.13 M130535.
Stamos, MD Michael J. et al. "Advances in Anal Fistula Repair: Minimizing Risk for Incontinence," General Surgery News, Dec. 2010, 4 pages.
"New Technique for Anal Fistula Showing Success" GeneralSurgeryNews.com, Special Report May 2006, 4 pages.
"OTSC Proctology in the treatment of anorectal fistulas," vol. 2 Anorectal Fistula, 2 pages, Oct. 10, 2012.
Piercarlo Meinero, M.D. "VAAFT: Video-Assisted Anal Fistula Treatment with closure of the internal fistula opening by stapler—the Meinero Technique," 24 pages, www.karlstorz.com, 2011.
Julián Panés et al. "Expanded allogeneic adipose-derived mesenchymal stem cells (Cx601) for complex perianal fistulas in Crohn's disease: a phase 3 randomised, double-blind controlled trial," Jul. 28, 2016, http://dx.doi.org/10.1016/S0140-3736(16)31203.x, 10 pages.

* cited by examiner

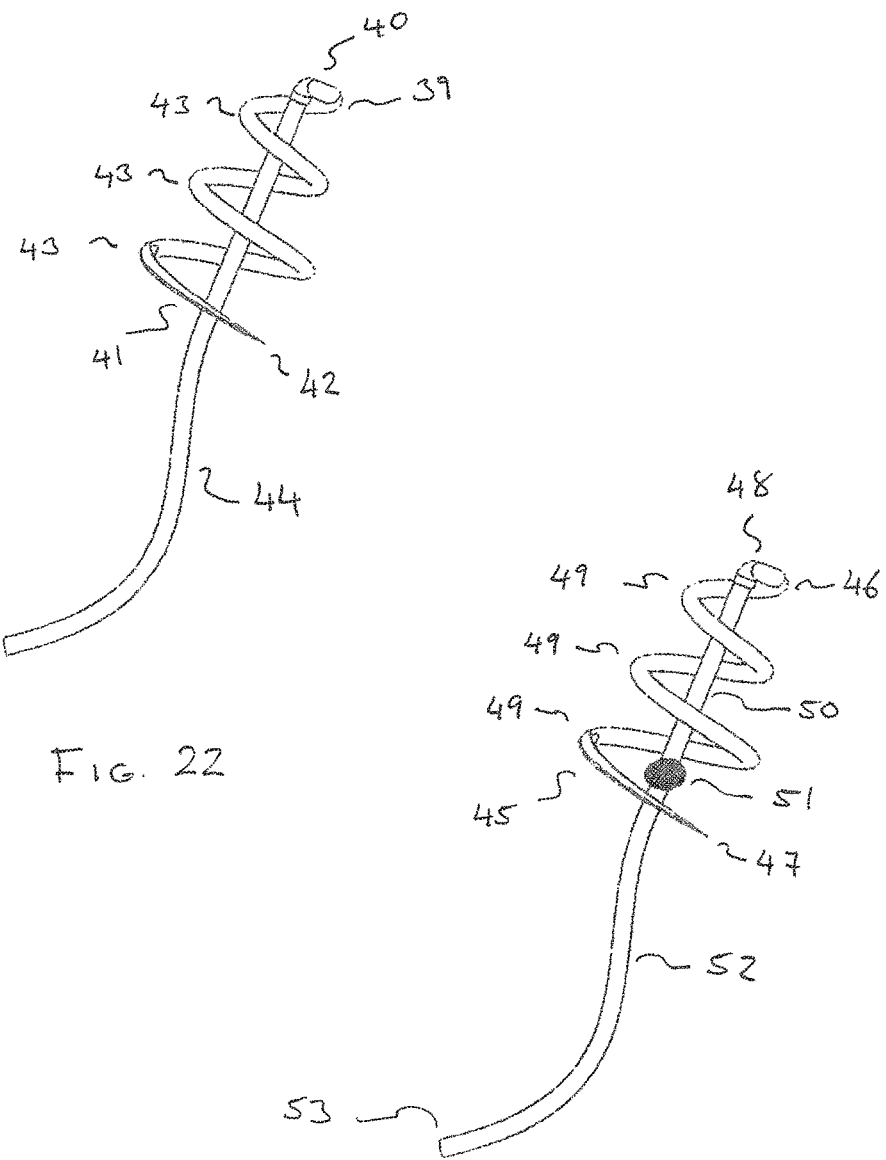

FISTULA TREATMENT DEVICE

CROSS-REFERENCE TO RELATED APPLICATIONS

This application is a continuation-in-part of International Application No. PCT/EP2016/061944, filed on May 26, 2016, which claims the benefit of priority of European Application No. 15169640.8, filed on May 28, 2015. This application also claims the benefit of priority of European Application No. 16201270.2, filed Nov. 29, 2016, and European Application No. 16174951.0, filed Jun. 17, 2016, all of which are incorporated by reference herein in their entireties.

INTRODUCTION

The invention relates to a device and a system for the treatment of perianal fistulas.

A perianal fistula is an artificial tunnel that, in the majority of cases, develops from an infection that begins within a blocked anal gland. If the infection cannot be cleared from the anal gland an abscess forms and the infection burrows though the sphincteric muscles and exits at the buttocks integument. Patients experience pain associated with the tract and associated abscesses and suffer faecal and blood discharge from the fistula tract. Perianal fistulas may also result from gastro-intestinal diseases such as Crohn's disease, ulcerative colitis, colorectal cancers and their associated treatment and complications due to rectal fissures and trauma.

The global incidence of perianal fistula is 2 per 10,000 population. Over 100,000 fistula procedures are performed between the United States and Western Europe each year. Thirty percent of the procedures performed are reoperations due to treatment failure contributing to a significant preventable cost to the healthcare systems.

Given the inadequate treatment options and poor surgical outcomes there is a defined clinical need for a more effective perianal treatment device.

There is currently no single "gold standard" technique that a surgeon can perform to effectively cure a perianal fistula and not render the patient incontinent. A common fistula treatment is a fistulotomy procedure. A fistulotomy involves the dissection of the sphincteric muscles and the laying open of the fistula tract. Fistulotomies have a relatively high cure rate, however, this procedure results in a high risk of faecal incontinence.

From a patient's point of view, many are happy to assume the risk of incontinence in order to resolve the painful fistula tract. However, this is obviously not an ideal treatment pathway and for many patient population groups the secondary outcome is far from acceptable.

Another commonly used fistula treatment methodology is the use of a seton. Setons are used as a sphincter sparing technique and is simply a suture or vascular strap that is passed through the tract of the fistula and the rectum and tied in a loop. The seton maintains tract patency allowing the infection in the fistula tract to drain, help the tract constrict in length and may cure the tract. If the tract is not cured by the seton the physician can perform a fistulotomy. This approach of trying to preserve the sphincter with setons has been used for over 2500 years and is still the preferred method used by surgeons today.

In an effort to provide a non-destructive perianal fistula treatment various glues and plugs have been developed and introduced to colorectal surgeons in the past 20 years. However, these techniques are not very successful and their use is not widespread. Such glues which are injected into the fistula tract generally become brittle and are not able to occlude the tract for a long enough period to fully heal, faeces re-enter the tract resulting in abscess formation and refistulisation. Physicians often attempt to treat perianal fistulas with glues and plugs even though there may only be a 10 percent chance of effectiveness because it is a sphincter sparing technique and they can always resort to a seton and eventual fistulotomy if all fails.

Attempts have also been made to use plugs to occlude perianal fistula tracts. For example, US2005/004926A describes a plug-like fistula closure device with an attached flexible application string which also serves to evacuate liquids out of a fistula. However, generally the plugs fail because they become extruded from the tract, allowing faeces to enter the tract resulting in reinfection, abscess formation and refistulisation.

There is therefore a need for an improved method and device for the treatment of perianal fistulas.

STATEMENTS OF INVENTION

According to the invention there is provided a fistula treatment system comprising a guide which is adapted to extend at least partially around a tissue tract. Also provided is an implant element which is adapted to track the pathway of a guide.

In one embodiment the implant element has a tracking configuration in which the implant element follows the pathway of the guide and an activated configuration, the implant in the activated configuration being adapted to draw tissue surrounding a tract inwardly.

The implant element in some cases comprises an anchor.

The anchor may comprise at least one barb.

The anchor may have a collapsed delivery configuration and a radially extending configuration.

The anchor may comprise a plurality of filaments.

In some cases the anchor is located at a distal end of the implant element.

In one embodiment the implant element forms a coil in the collapsed deployed configuration.

The coil in one case has a substantially uniform lateral extent along a length thereof.

The coil may be tapered along a length thereof.

In one embodiment the implant element is an activatable element. The activatable element may have a collapsed delivery configuration, a deployed configuration and an activated configuration. The activatable element may comprise an expansile element such as a balloon, or a foam.

In some embodiments the implant element comprises a shape memory material such as Nitinol.

In one case the implant element is at least partially bioabsorbable.

In some embodiments there are a plurality of implant elements.

In some embodiments the guide comprises a guide coil.

The guide coil may have a substantially uniform lateral extent along a length thereof.

The guide coil may be tapered along a length thereof.

In some cases the coil comprises a rail for the implant element.

The coil may be solid or hollow.

In one case the guide coil comprises a sharp distal tip.

In some embodiments the system comprises a drain or seton having an anchoring feature for anchoring the drain/seton in situ.

The anchoring feature may be provided at a compression zone or region of the seton.

In some cases the anchoring feature comprises a step or projection on the seton, such as one or more of a knot, a barb or a quill.

The seton may be hollow or solid.

In some cases the seton has a plurality of peripheral holes.

In some embodiments the shape of seton in cross section is selected from one or more of round, oval, star and cross.

The seton may comprise multiple elements. The elements of the seton may be braided.

In some cases at least a portion of the seton is bioabsorbable. In one case the seton is of differential bioabsorption. A proximal portion of the seton may be bioabsorbable.

The seton may extend from the implant.

In some cases at least a portion of the implant is bioabsorbable and at least a portion of the seton is configured to bioabsorb in advance of bioabsorption of the implant.

In another case the seton is bioabsorbable and the implant is not bioabsorbable.

The invention also provides a method for treating a perianal fistula comprising the steps of:—
  providing an implant;
  inserting the implant into the bulk tissue of the sphincteric muscle complex adjacent to the fistula; and
  using the implant to draw tissue surrounding the fistula inwardly.

The method may further comprise:—
activating the implant to draw tissue surrounding the tract inwardly.

The method may comprise anchoring the implant in the tissue.

In some cases the implant is anchored prior to activation of the implant.

The invention further provides a method for closing a fistula comprising:—
  providing a guide and an implant element;
  advancing the guide to extend at least partially around a tissue tract;
  advancing the implant element to follow the track of the guide; and
  withdrawing the guide leaving the implant element in place surrounding the tissue tract.

The method may further comprise activating the implant element to draw tissue surrounding the tract inwardly. The method may further comprise anchoring the implant element in tissue, prior to activating the implant element.

According to the invention there is also provided a perianal fistula treatment device comprising an implant coil having an anti-rewind feature. The anti-rewind feature may be selected from one or more of:
  a positive feature such as a barb, arrowhead or fishhook-like feature;
  a negative feature such as a trough, a slot or a groove, and
  a surface feature such as surface roughening.

In one embodiment the device comprises a tapered portion which is configured for insertion into bulk tissue surrounding a fistula and a driver interface portion which is configured for engagement with a driver for rotation of the coil to draw tissue surrounding a fistula inwardly.

The invention also provides a drainage seton having an anchoring feature for anchoring the seton in situ. In some cases the anchoring feature is provided at a compression zone or region of the seton.

In some embodiments the anchoring feature comprises a step or projection on the seton, such as one or more of a knot, a barb or a quill.

The invention further provides a fistula treatment system comprising a fistula treatment device of the invention and a driver implement for rotation of the coil to draw tissue surrounding a fistula inwardly. In one embodiment the driver implement comprises a driver coil which is configured for engagement with the driver interface of the implant coil.

In some cases at least a portion of the outer surface of the driver coil is lubricious.

There may be engagement features on the driver coil and/or the implant coil for temporarily locking the driver coil to the implant coil for delivery of the implant coil.

The invention also provides a fistula treatment system comprising a fistula treatment device of the invention and a tissue stabilising device for stabilising the mucosal tissue for delivery of the implant.

In some embodiments the stabilising device comprises a hollow element attached to the delivery mechanism and surrounding the implant prior to delivery. The hollow element may be spring loaded or otherwise to apply pressure to the mucosal surface.

In one embodiment a leading surface of the hollow element that interfaces to the mucosal surface interacts with the mucosal surface to prevent rotation and/or twisting of the mucosal lining. The hollow element may comprise features such as needles for penetration into the mucosal surface.

The invention also provides a method for treating a perianal fistula comprising the steps of:—
  providing a tapered coil;
  inserting the coil into the bulk tissue of the sphincteric muscle complex adjacent to the fistula; and
  rotating the coil to draw tissue surrounding the fistula inwardly.

In some embodiments the method comprises:—
  providing a drainage seton;
  embedding the seton in the sphincter muscle complex; and
  leading the seton so that the distal end of the seton protrudes through the external
  opening of a fistula tract.

Also provided is a method for treating a perianal fistula comprising the steps of:—
  providing an implant coil with a delivery interface region;
  providing a delivery device with an implant coil interface region;
  inserting the implant coil into the delivery device; and
  rotating the implant coil using the delivery device.

In some cases, after insertion of the implant coil, the delivery device is released from the coil.

The method may further comprise:—
  providing a drainage seton;
  attaching the seton to the coil; and
  leading the seton externally of the fistula.

The method may comprise:—
  providing a drainage seton;
  embedding the seton in the sphincter muscle complex; and
  leading the seton so that the distal end of the seton protrudes through the external
  opening of a fistula tract.

According to the invention there is provided a perianal fistula treatment device comprising an implant coil having a tapered portion which is configured for insertion into bulk tissue surrounding a fistula and a driver interface portion which is configured for engagement with a driver for rotation of the coil to draw tissue surrounding a fistula inwardly.

In one embodiment the driver interface portion of the coil has a substantially uniform lateral extent along a length thereof.

In one case the coil has a leading end, a transition region, and a trailing end, the tapered portion of the coil extending from the leading end to the transition region and the driver interface portion extending from the transition region.

Preferably the tapered portion of the coil decreases in lateral extent between the leading end and the transition region.

In one case the leading end of the tapered portion has a pointed tissue insertion tip.

In one embodiment at least the driver interface portion of the coil is solid.

Alternatively at least the driver interface portion of the coil is hollow.

In one case the coil is solid.

Alternatively the coil is hollow.

In some cases the shape of the coil in cross section is selected from one or more of round, oval, triangular, multifaced and ribbon.

In one embodiment at least a portion of the coil is bioabsorbable.

In one case the fistula treatment device further comprises a drainage seton.

The seton may extend from the coil.

In one case the seton is hollow.

In one case the seton is solid.

In one embodiment the seton has a plurality of peripheral holes.

The shape of seton in cross section in some cases is selected from one or more of round, oval, star and cross.

In one embodiment the seton comprises multiple elements. The elements of the seton may be braided.

In one case at least a portion of the seton is bioabsorbable.

In one case the seton is of differential bioabsorption. In one embodiment a proximal portion of the seton is bioabsorbable, for example, to facilitate removal of a remainder of the seton. In another embodiment a distal portion of the seton is bioabsorbable to facilitate closure of the enternal opening of the fistula prior to full absorption of the seton.

In one embodiment at least a portion of the coil is bioabsorbable and at least a portion of the seton is configured to bioabsorb in advance of bioabsorption of the coil.

The invention also provides a fistula treatment system comprising a fistula treatment device and a driver implement for rotation of the coil to draw tissue surrounding a fistula inwardly.

In one case the driver implement comprises a driver coil which is configured for engagement with the driver interface of the implant coil.

In one embodiment the driver coil has a substantially uniform lateral extent along a length thereof for engagement with the corresponding driver interface portion of the implant coil.

In one case the driver coil is hollow and the corresponding driver interface portion of the implant coil is solid.

In another case the driver coil is solid and the corresponding driver interface portion of the implant coil is hollow.

The invention also provides a perianal fistula treatment device comprising an implant coil which is configured for insertion into bulk tissue surrounding a fistula and being rotatable to draw tissue surrounding the fistula inwardly and a drainage seton extending from the tapered coil.

In one case the coil is tapered.

The invention also provides a perianal fistula treatment device comprising a tapered coil and a drainage seton mounted to and extending from the tapered coil.

The invention also provides a perianal fistula treatment device comprising an implant coil which is configured for insertion into tissue surrounding a fistula and a drainage seton wherein at least a portion of the seton is bioabsorbable.

In one embodiment the seton is of differential bioabsorption.

In one case a proximal portion of the seton is bioabsorbable to facilitate removal of a remainder of the seton.

The tapered coil is preferably configured for insertion at the site of the internal opening of a fistula and being rotatable to draw bulk tissue, including sphincteric muscle, surrounding the fistula inwardly.

In one case the coil has a leading end and a trailing end, the coil decreasing in lateral extent between the leading and trailing ends. The leading end may include a pointed tissue insertion tip.

In one embodiment the device comprises a seton attachment feature.

The attachment feature may be selected from one or more of:—a protrusion such as a ball-shape; a hook; a cleat; a butt joint; or a bond such as a thermal and/or adhesive bond.

In one embodiment the centering element has a recess or hole for reception of a seton. The seton may be bonded or fixed to the recess or hole in the centering feature, for example by adhesive and/or thermal bonding, and/or crimping.

In another embodiment the device comprises a delivery mechanism attachment feature.

In one case the device comprises a centre element which extends at least partially along a longitudinal axis of the coil.

The centre element may extend from the trailing end of the coil towards the leading end of the coil.

The centre element may extend to a distance beyond the leading end of the coil.

The centre element may comprise a seton attachment feature and/or a delivery mechanism attachment feature.

In one case the seton is hollow.

The seton may have a plurality of peripheral holes.

The shape of the seton in cross section may be selected from one or more of round, oval, star and cross.

In one case the seton comprises multiple elements which may be braided.

In one case the coil is solid. In another case the coil is hollow.

The shape of the coil in cross section may be selected from one or more of round, oval, triangular, multifaced and ribbon.

The invention also provides a fistula treatment device comprising a tapered coil which is configured for insertion into bulk tissue surrounding a fistula and being rotatable to draw tissue surrounding the fistula inwardly, the coil having a centering element that extends at least partially along a longitudinal axis of the coil.

The device may further comprise a drainage seton mounted to and extending from the tapered coil.

In one case the coil has a leading end and a trailing end, the coil decreasing in lateral extent between the leading and trailing ends. The leading end may include a pointed tissue insertion tip.

In one embodiment the device comprises a seton attachment feature.

In one embodiment the device comprises a delivery mechanism attachment feature.

In one case the centering element extends from the trailing end of the coil towards the leading end of the coil.

In one embodiment the centering element comprises a seton attachment feature. The attachment feature may be selected from one or more of:—a protrusion such as a ball-shape; a hook; a cleat; a butt joint; or a bond such as a thermal and/or adhesive bond.

The centering element may have a recess or hole for reception of a seton. The seton may be bonded or fixed to the recess or hole in the centering feature, for example by adhesive and/or thermal bonding, and/or crimping.

In one embodiment the centering element comprises a delivery mechanism attachment feature. The seton may be hollow or solid. The seton may have a plurality of peripheral holes. The seton in cross section may be selected from one or more of round, oval, star and cross. The seton comprises multiple elements. The elements may be braided. The coil may be solid or hollow. The shape of the coil in cross section may be selected from one or more of round, oval, triangular, multifaced and ribbon.

The invention also provides a system comprising a fistula device of the invention and a delivery device for the perianal fistula treatment device.

In one embodiment the delivery device comprises a hollow element through which the tapered coil is delivered.

In one embodiment the delivery device comprises a solid element over which a hollow tapered coil is delivered.

In one embodiment the delivery device comprises a hollow element through which a straight cylindrical coil is delivered.

In one embodiment the delivery device comprises a solid element over which a hollow straight cylindrical coil is delivered.

The hollow delivery element may comprise a coil.

In one embodiment the delivery device comprises a rail for the delivery of the tapered coil. The rail and the coil may comprise interengagable track features.

The invention also provides a method for treating a perianal fistula comprising the steps of:—
 providing a tapered coil;
 inserting the coil into the bulk tissue of the sphincteric muscle complex adjacent to the fistula; and
 rotating the coil to draw tissue surrounding the fistula inwardly.

In one embodiment the method further comprises:
 providing a drainage seton;
 attaching the seton to the coil;
 using the seton to provide apposition of the coil and mucosal surface prior to delivery of the coil; and
 leading the seton externally of the fistula;

In one case the method comprises embedding the seton in the sphincter muscle complex and leading the seton so that the distal end of the seton protrudes through the external opening of a fistula tract.

The invention also provides a method for treating a perianal fistula comprising the steps of:—
 providing an implant coil with a delivery interface region;
 providing a delivery device with an implant coil interface region;
 inserting the implant coil into the delivery device; and
 rotating the implant coil using the delivery device.

In one embodiment, after insertion of the implant coil, the delivery device is released from the coil.

The method may further comprise:—
 providing a drainage seton;
 attaching the seton to the coil; and
 leading the seton externally of the fistula.

The method may comprise:—
 providing a drainage seton;
 embedding the seton in the sphincter muscle complex; and
 leading the seton so that the distal end of the seton protrudes through the external opening of a fistula tract.

The perianal fistula treatment device has the advantages of:
 effective healing of the fistula tract;
 preservation of continence; and
 improved healing time.

The device preserves the patient's continence by protecting the sphincteric muscles from division. The device is securely anchored into the fistula tract, effectively sealing the tract and preventing faecal matter from entering the internal opening during the healing process.

The device allows any remaining abscess materials to drain from the tract during the healing process. The device may be integrated into the tissue over the healing process, and may be ultimately absorbed as the tract is healed.

The invention removes variability due to surgeon skill by providing a standardised technique for treating perianal fistulas.

The device facilitates gathering and apposing sphincter muscle tissue allowing repair of a defect in the muscle bulk.

A single ended drainage seton is attached to allow drainage of a fistula tract post closure of the internal opening of a tract.

A delivery mechanism is provided with attachment feature(s) to interface with the tapered coil and seton.

The tapered coil may have an anchor for a single ended seton.

The tapered coil may be of metal, bioabsorbable polymer, bioabsorbable metal.

The drainage seton may be made from any suitable materials including bioabsorbable, synthetic.

The system may be capable of delivering multiple coils.

The system may be capable of delivering a tapered coil located at the distal portion of an endoscope.

The method for treating an anal fistula may include any or all of the following steps:
 using seton for location/tension/mucosal wall apposition prior to delivering;
 using a delivery mechanism to deliver a closure device to repair a defect in the bulk tissue of the sphincteric muscle complex;
 delivering a closure device below the surface of the mucosal lining of the rectum at the dentate line into bulk tissue to allow remodelling of the mucosal lining over the site of delivery; and
 embedding a seton in the sphincter muscle complex with the distal end protruding through the external opening of a fistula tract in order to allow drainage and healing of a fistula tract.

Aspects of the present disclosure may be directed to a method of treating a perianal fistula with an implant. The implant may have a proximal end and a distal end, and the perianal fistula may have an internal opening from the rectum, an external opening in an external surface of a buttocks, a fistula tract extending between the internal opening and the external opening, and fistula tissue surrounding the fistula tract. The method may include:
 engaging the distal end of the implant about the internal opening to compress fistula tissue via the implant, sealing closed the internal opening of the fistula tract while leaving open the external opening of the fistula tract, and embedding the proximal end of the implant in the fistula tissue such that none of the implant may be exposed to the rectum.

The sealing may include sealing against pressure of up to 150 mmHg.

The sealing may include sealing against pressure of up to 200 mmHg.

The compressing may include compressing fistula tissue in an opposed configuration.

The method may further include facilitating a passageway through the external opening to allow for draining.

The method may further include positioning a drainage member within the fistula tract.

At least a portion of the drainage member may extend from a location within the fistula tract and through the external opening.

The compressing may include progressively compressing fistula tissue such that a compression force imparted to fistula tissue via the distal end of the implant may be less than a compression force imparted to fistula tissue via the proximal end of the implant.

Following the compressing, a majority of the fistula tract may remain open.

Aspects of the present disclosure may be directed to a method of treating a perianal fistula with an implant. The implant may have a proximal end and a distal end, and the perianal fistula may have an internal opening from the rectum, an external opening in an external surface of a buttocks, a fistula tract extending between the internal opening and the external opening, and fistula tissue surrounding the fistula tract. The method may include:

forming a perianal sinus by closing the internal opening with the implant.

The forming the perianal sinus may include rotating the implant to advance the implant through fistula tissue toward the external opening.

The rotating of the implant may cause compression of the fistula tissue.

The method may further include drawing fistula tissue radially inwardly, a first region of fistula tissue may be drawn radially inwardly to a greater extent than at least a second region of fistula tissue, and the first region may be closer to the internal opening than the second region.

The implant may comprise a tapered portion, the forming the sinus may include drawing tissue radially inwardly via the tapered portion, a proximal end of the tapered portion having a diameter less than a distal end of the tapered portion, the implant being deployed such that the proximal end may be closer to the internal opening than the distal end.

The method may further include positioning a drainage member within the fistula tract, at least a portion of the drainage member may extend from a location within the fistula tract and through the external opening.

The method may include embedding the proximal end of the implant in the fistula tissue.

The forming of the perianal sinus may further include forming a seal against pressure of up to 150 mmHg.

Aspects of the present disclosure may be directed to a method of treating a perianal fistula with an implant. The implant may have a proximal end and a distal end, and the perianal fistula may have an internal opening from the rectum, an external opening in an external surface of a buttocks, a fistula tract extending between the internal opening and the external opening, and fistula tissue surrounding the fistula tract. The method may include:

contacting the fistula tissue with the implant about the internal opening, the implant may include a coil having a plurality of coil loops extending between the proximal end and the distal end, at least a portion of the coil may be tapered along a length of the coil between the proximal end and the distal end;

rotating the implant into fistula tissue to advance the distal end of the implant toward the external opening, causing a diameter of at least a portion of the fistula tract to be reduced via the tapered portion; and facilitating drainage through the external opening after the implant is in place.

The method may further include compressing fistula tissue via the implant, the compressing may include progressively compressing fistula tissue such that a compression force imparted to fistula tissue via the distal end of the implant may be less than a compression force imparted to fistula tissue via the proximal end of the implant.

The method may further include compressing fistula tissue so as to close the internal opening while maintaining the external opening open.

The facilitating drainage through the external opening may include positioning a drainage member in the fistula tract, at least a portion of the drainage member may extend from a location within the fistula tract and through the external opening.

The at least one of the implant or the drainage member may be bioabsorbable.

Both of the implant and the drainage member may be bioabsorbable, and a rate of absorption of the implant may be faster than a rate of absorption of the drainage member.

Both of the implant and the drainage member may be bioabsorbable, and a rate of absorption of the drainage member may be faster than a rate of absorption of the implant.

A method of closing an opening in tissue may include:

delivering a helical implant into tissue such that a plurality of helical loops of the implant may pass through tissue surrounding the opening and may compress the tissue radially inwardly; and fixing a drain element relative to the implant such that after the implant is delivered the drain element may extend from within the opening to a location outside of the opening, the drain element may be configured to facilitate fluid drainage from the opening along the drain element.

The method may further include drawing tissue around the opening radially inwardly toward a center of the implant, a first region of tissue may be drawn radially inwardly to a greater extent than at least a second region of tissue.

The implant may include a tapered coil portion tapering toward a proximal end of the coil.

The method may further include sealing closed only one end of the opening.

The method may further include engaging a tapered distal section of a delivery device with an inner surface of the implant.

The method may further include engaging a non-tapered distal section of a delivery device with an external surface of the implant.

An implant for treating a fistula may comprise:

a shaft having a proximal end, a distal end, and a plurality of coil loops; and a plurality of barbs positioned on the shaft, each of the plurality of barbs may be located distally of a proximal-most coil loop of the plurality of coil loops;
the shaft may include a tapered portion.
The shaft may further include a non-tapered portion.
Each of the plurality of barbs may be located distally of the non-tapered portion.
The non-tapered helical coil portion may extend along a minority of a length of the shaft between the proximal end and the distal end.
Each of the plurality of barbs may be a pre-formed, positive, anti-rotation feature.
An implant for treating a fistula may comprise:
a shaft having a proximal end and a distal end and forming a helical coil therebetween, the helical coil may have:
a tapered portion comprising a first plurality of coil loops; and
a non-tapered portion comprising a second plurality of coil loops.
The tapered portion may include more coil loops than the non-tapered portion.
A longitudinal length of the non-tapered portion may be smaller than a longitudinal length of the tapered portion.
The implant may include a channel extending along a surface of at least some of plurality of coil loops.
The implant may further include a drainage member having a deployed configuration in which the drainage member may be fixed relative to the implant.
The implant may further include a driving abutment positioned between the proximal end and the distal end.
A system for treating a fistula may comprise:
an implant extending between a proximal end and a distal end, the implant may include:
a helical coil having a plurality of coil loops including a tapered portion; and
a driver coil extending between a proximal end and a distal end, the driver coil and the helical coil of the implant may have a common pitch; and
in a first configuration, a section of the driver coil may be engaged with a portion of the implant, and in a second configuration, the section of the driver coil may be disengaged from the portion of the implant.
The implant may include a channel extending along a surface of at least some of plurality of coil loops.
The driver coil may be a non-tapered coil.
The implant may further include a non-tapered portion.
The implant may further include a driving abutment located along the non-tapered portion.
The non-tapered portion may extend along a minority of a length of the implant between the proximal end and the distal end of the implant.
In the first configuration, one of the section of the driver coil and the portion of the implant may be received within the other of the section of the driver coil and the portion of the implant.
The portion of the implant may be the non-tapered portion.
The system may further include a drainage member having a deployed configuration in which the drainage member may be fixed relative to at least one of the implant or the driver coil.
A kit for closure of an opening in human tissue may comprise:
an implant having a shaft forming a helical coil and having a proximal end and a distal end, at least a portion of the helical coil may have a tapered coil portion; and
a longitudinally extending drain member.

The helical coil may further include a non-tapered coil portion.
The tapered coil portion may include a first plurality of coil loops and the non-tapered coil portion may include a second plurality of coil loops, the first plurality of coil loops may include a greater number of coil loops than the second plurality of coil loops.
A longitudinal length of the non-tapered helical coil portion may be smaller than a longitudinal length of the tapered helical coil portion.
A driving abutment may be positioned between the proximal end and the distal end.
At least one of the implant or the drain member may be bioabsorbable.
Both of the implant and the drain member may be bioabsorbable, and a rate of absorption of the implant may be faster than a rate of absorption of the drain member.
Both of the implant and the drain member may be bioabsorbable, and a rate of absorption of the drain member may be faster than a rate of absorption of the implant.

BRIEF DESCRIPTION OF THE DRAWINGS

The invention will be more clearly understood from the following description of an embodiment thereof, given by way of example only, with reference to the accompanying drawings, in which.

FIG. 22 is an isometric view of a device with pointed tip and centre feature and seton;

FIG. 23 is an isometric view of a device with pointed tip and centre seton attachment feature with attached seton;

DETAILED DESCRIPTION

The device is capable of one or more of the following: accommodating varied fistula tract physiology;

occluding and sealing the internal opening of the tract;
preventing faecal matter re-infecting the tract;
preserving sphincteric function;
enhancing fistula tract healing; and
facilitating drainage during healing.

The perianal fistula treatment device ensures sparing of the sphincter, occluding of the fistula tract internal opening, and promotion of drainage and tissue healing.

The device consists of a head with anchoring and sealing mechanisms which is secured in the tissue tract and prevents re-infection of the wound. A tail section provides seton-like drainage and prevents re-abscessing due to premature closure of the skin site.

The anchoring and sealing mechanism of the device consists of a tapered coil. The coil geometry is designed to pull tissue together as is it deployed into the sphincter muscle complex, resulting in a strong anchor but also, importantly, an effective compressive seal preventing reinfection of the fistula tract and close tissue approximation to enhance tissue healing.

The perianal fistula treatment device preserves sphincteric and anatomical conditions and functions, prevents re-fistulisation, and improves healing time over the current treatment methods. The device consists of a tapered coil and a drainage seton. There may be a centering alignment feature. A delivery mechanism is also described. The coil may be led into the fistula tract by the drainage seton and centered into the tract by means of the centering feature. The larger diameter of the tapered coil is abutted against the tissue surface, surrounding the internal opening of the fistula tract with adequate margin. The delivery mechanism rotates the coil until it is just submucosal positioned. The coil closes the fistula internal opening by compressing the tract's surrounding tissue inwardly such that the tissue is brought within close approximation creating a seal impermeable to foreign materials and promoting tissue growth across the closely approximated fistula tract. The drainage seton provides a conduit to drain any abscess and remaining or newly formed exudate and fluids from the fistula tract throughout the time of the healing process. The centering feature insures the coil device is placed easily into the fistula tract and the outer coil is placed within the adequate margins surrounding the fistula tract and acts as a securing mechanism for the drainage seton.

Figure 1:
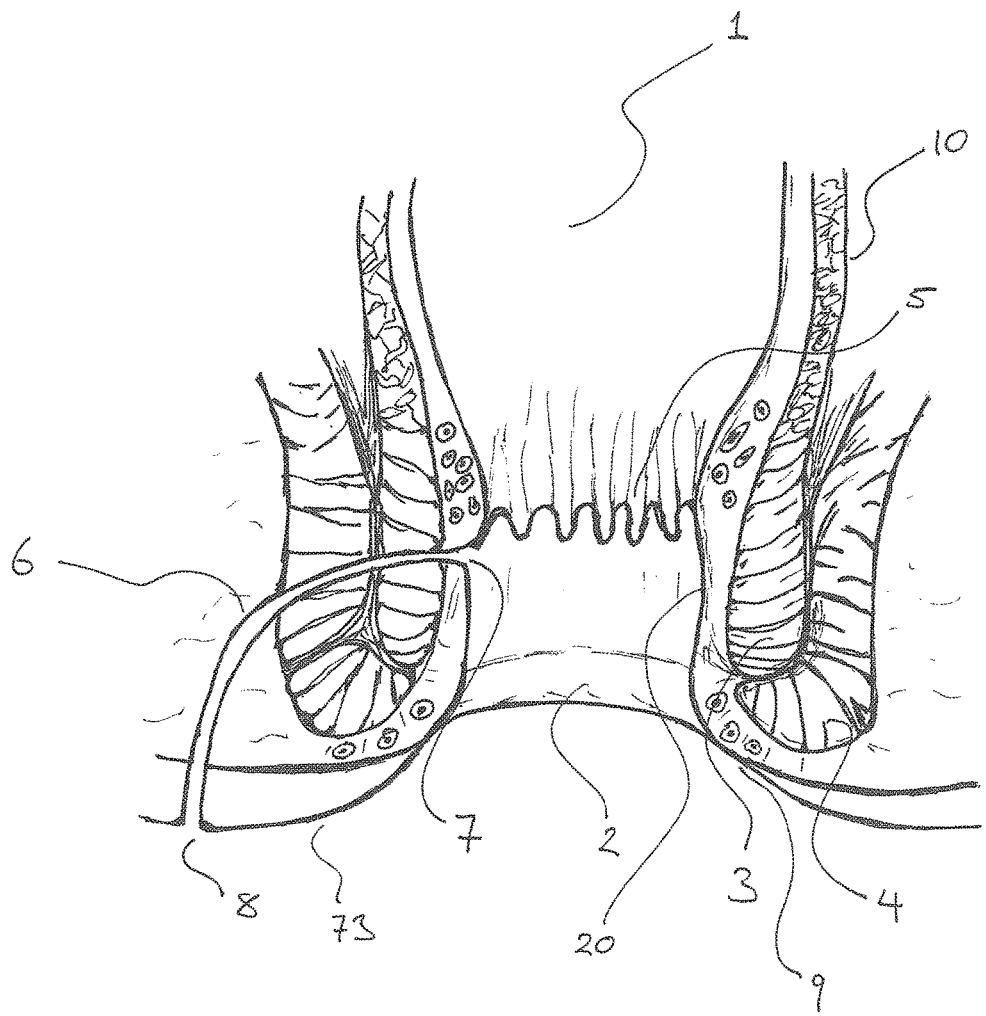
FIG. 1 is a cross-sectional view of an anatomy and disease state addressed by the invention.

The following numerals are used in the drawings:
1. Rectum
2. Anus
3. Internal Sphincter Muscle
4. External Sphincter Muscle
5. Dentate Line
6. Fistula Tract
7. Internal Opening
8. External Opening
9. Anal Verge
10. Levator Ani Muscle
11. Coil
12. Seton
13. Seton Distal End
14. Seton Attachment
15. Coil Distal Tip
16. Delivery Mechanism Member
17. Delivery Mechanism Interface
18. Delivery Mechanism
19. Internal Opening Mucosal Surface
20. Musocal Surface
21. Internal Opening
22. Compressed Sphincter Muscle Tissue
23. Coil
24. First End
25. Second End
26. Medial Portion
27. Coil Member
28. Pointed Tip
29. Delivery Mechanism Interface Feature
30. First End
31. Second End
32. Coil Member
33. First End
34. Second End
35. Pointed Tip
36. Centre Feature
37. Coil Member
38. Delivery Mechanism Interface Feature
39. Second End
40. Delivery Mechanism Interface Feature
41. First end
42. Pointed Tip
43. Coil Member
44. Centre Seton Feature
45. First End
46. Second End
47. Pointed Tip
48. Delivery Mechanism Interface Feature
49. Coil Member
50. Centre Feature
51. Seton Attachment Feature
52. Drainage Seton
53. Drainage Seton End
54. Cross Shape Seton Cross Section
55. Oval Seton Cross Section
56. Round Seton Cross Section
57. Outer Wall Hollow Round Seton Cross Section
58. Round Hollow Cross Section
59. Hollow Perforated Seton
60. First End
61. Second End
62. Hollow Centre Section
63. Perforation
64. Hollow Star Seton Cross Section
65. Solid Star Seton Cross Section
66. Hollow Perforated Star Seton
67. First End
68. Second End
69. Hollow Feature
70. Perforation
71. Cross Shape Seton Cross Section
72. Braided Seton Cross Section
73. Integument
200. Implant coil
201. Coil straight section
202. Coil tapered section
203. Transition from straight to tapered section
204. Hollow delivery assembly
205. Hollow delivery coil
206. Solid coil implant
207. Coil straight section
208. Coil tapered section
209. Interface
210. Solid delivery assembly
211. Hollow coil implant
212. Solid delivery coil
213. Coil straight section
214. Coil tapered section
220. Leading end
221. Trailing end FIG. 1 illustrates an anal fistula tract 6, which is an abnormal connection between the rectum 1 and the integument of the buttocks 73. The internal opening 7 of the fistula is located at the mucosal surface 20 of the rectum 1. The fistula tract 6 may generally originate at the dentate line and pass through the sphincteric muscle complex which consists of the internal sphincter muscle 3 and external sphincter muscle 4. The external opening 8 of the fistula tract 6 is located at the integument surface of the buttocks 73.

Figure 2:
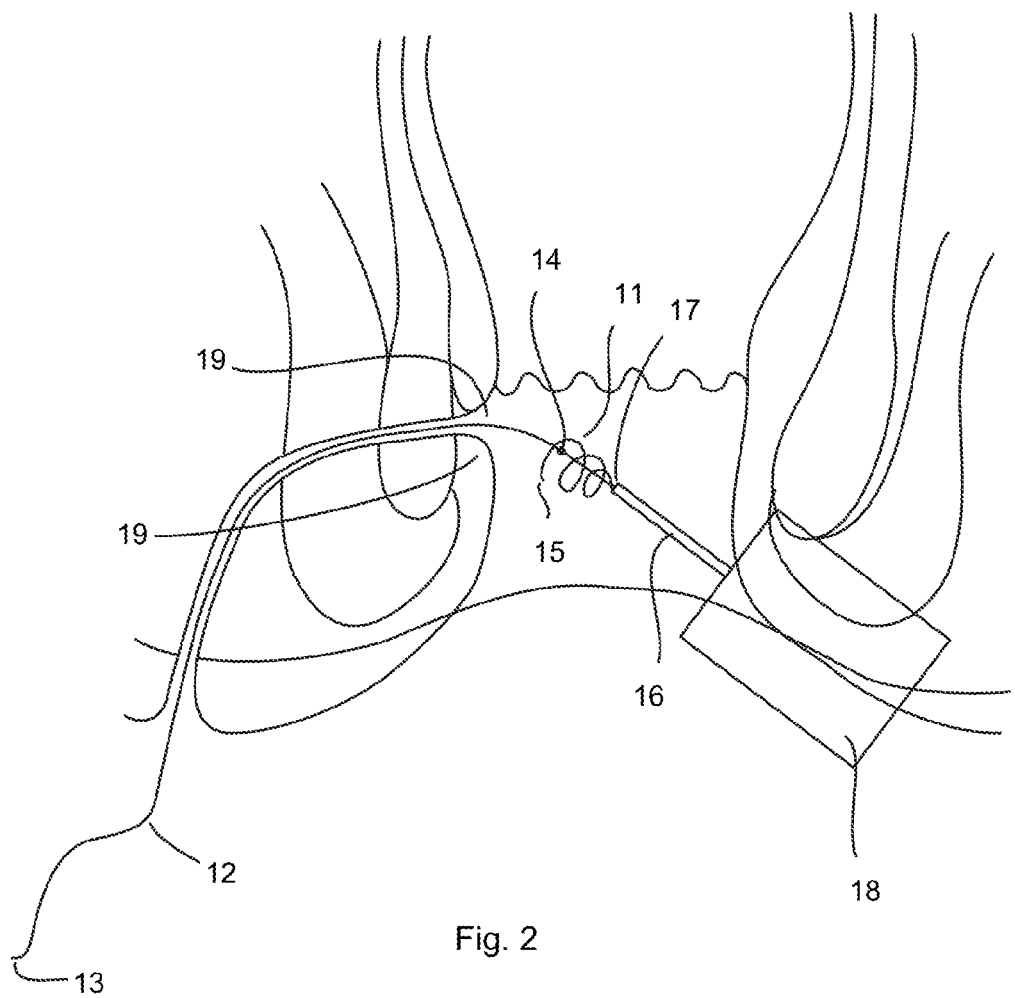
FIG. 2 is a cross-sectional view of the treatment device of the invention being delivered through the fistula tract.

FIG. 2 shows the device consisting of a tapered coil 11, drainage seton 13, and delivery mechanism 18 being drawn through the fistula tract by means of tension applied to second end of drainage seton 13.

Figure 3:
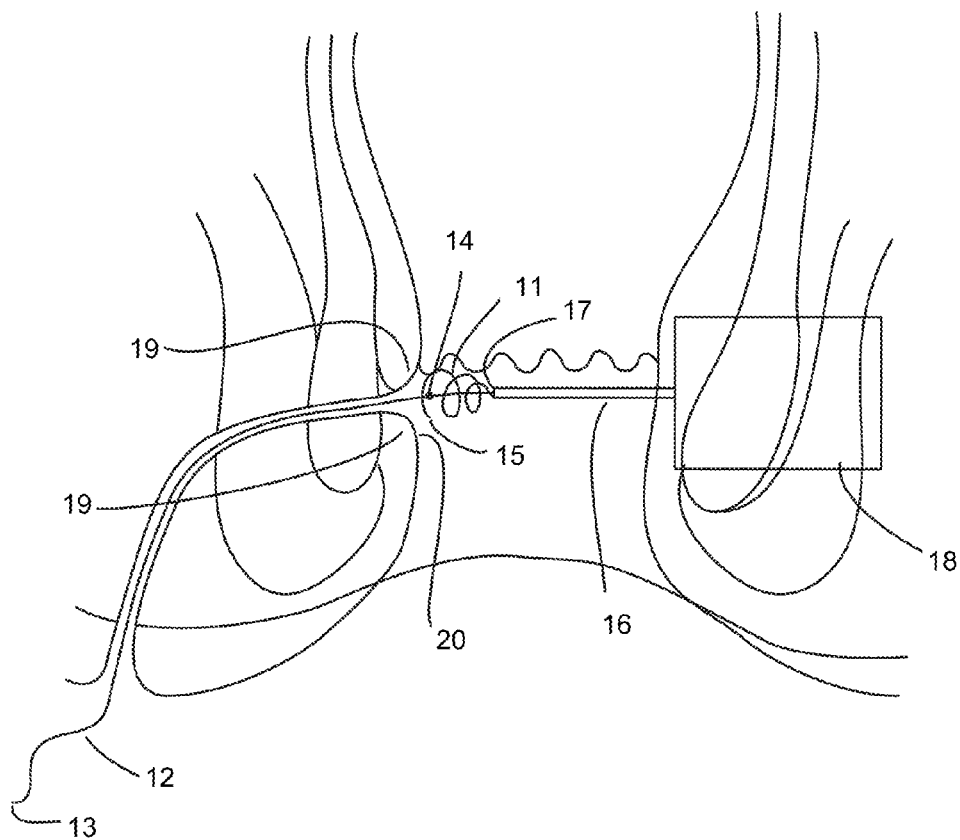
FIG. 3 is cross-sectional view of the device at a point of apposition to the mucosal surface at the site of the internal opening of the fistula tract.

The tapered coil 11 is brought into apposition to the mucosal tissue wall of the rectum 20 as shown in FIG. 3. The coil is centered on the internal opening of the fistula tract 7 at the dentate line 5 via tension applied to the second end 13 of the drainage seton 12 and the support of the bioabsorbable mechanism 18 interface 17.

Figure 4:
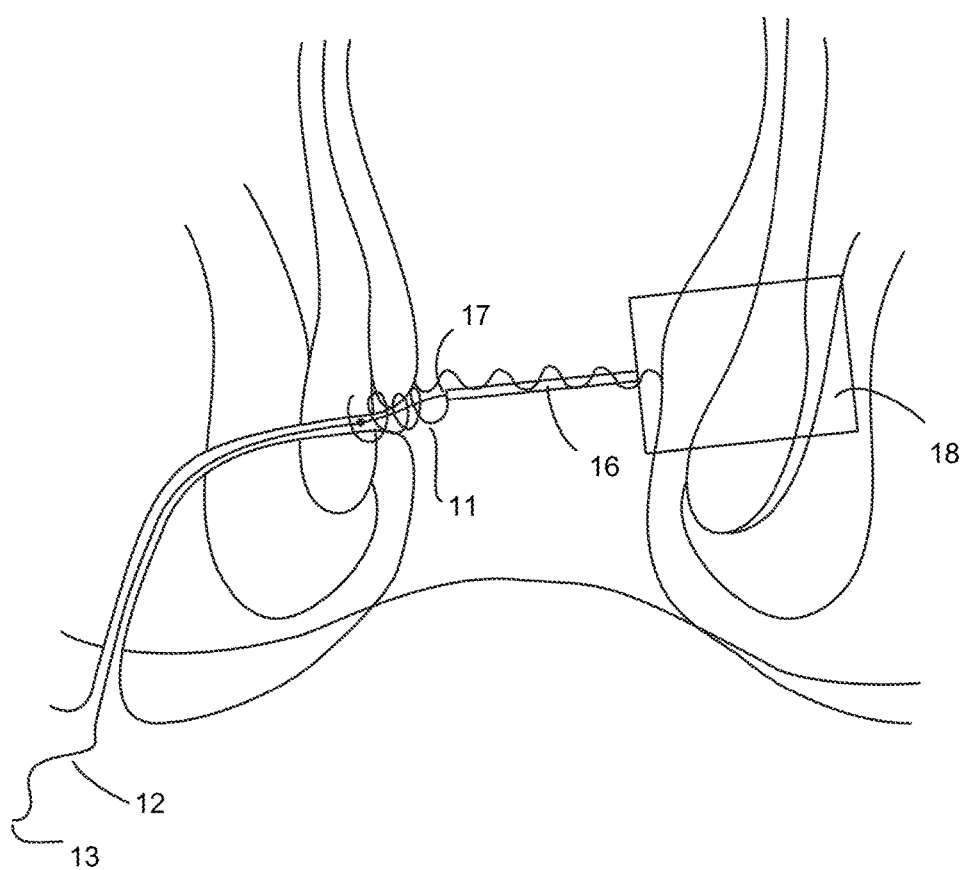
FIG. 4 is cross-sectional view of the device partially delivered through the mucosal surface and into the sphincter muscle complex.

The driver mechanism 17 delivers the coil 11 through the mucosal lining 20 of the rectum 1 via rotatory or other means (FIG. 4). The distal tip 15 of the coil 11 punctures through the musocal lining surface 20 and engages initially with the internal sphincter muscle 3 surrounding the internal opening 7 of the fistula tract 6.

Figure 45:
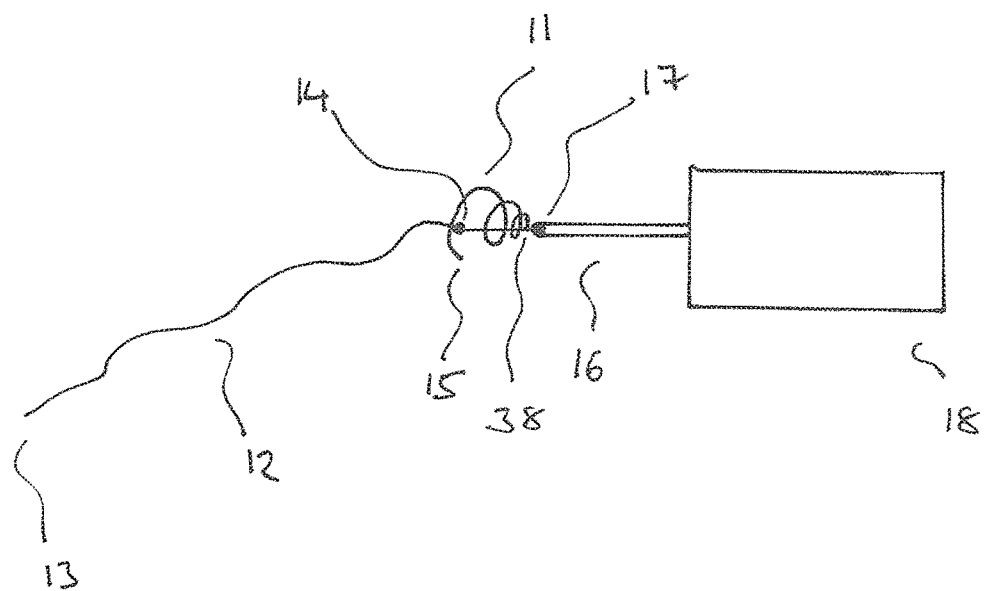
FIG. 45 illustrates the component parts of the system.

FIG. 45 illustrates the system component parts. The delivery mechanism interface feature 38 of the coil 11 is attached to the delivery mechanism member 16 of the delivery mechanism 18. The drainage seton 12 is attached to a coil centering feature 50 via the seton attachment feature 14.

Figure 5:
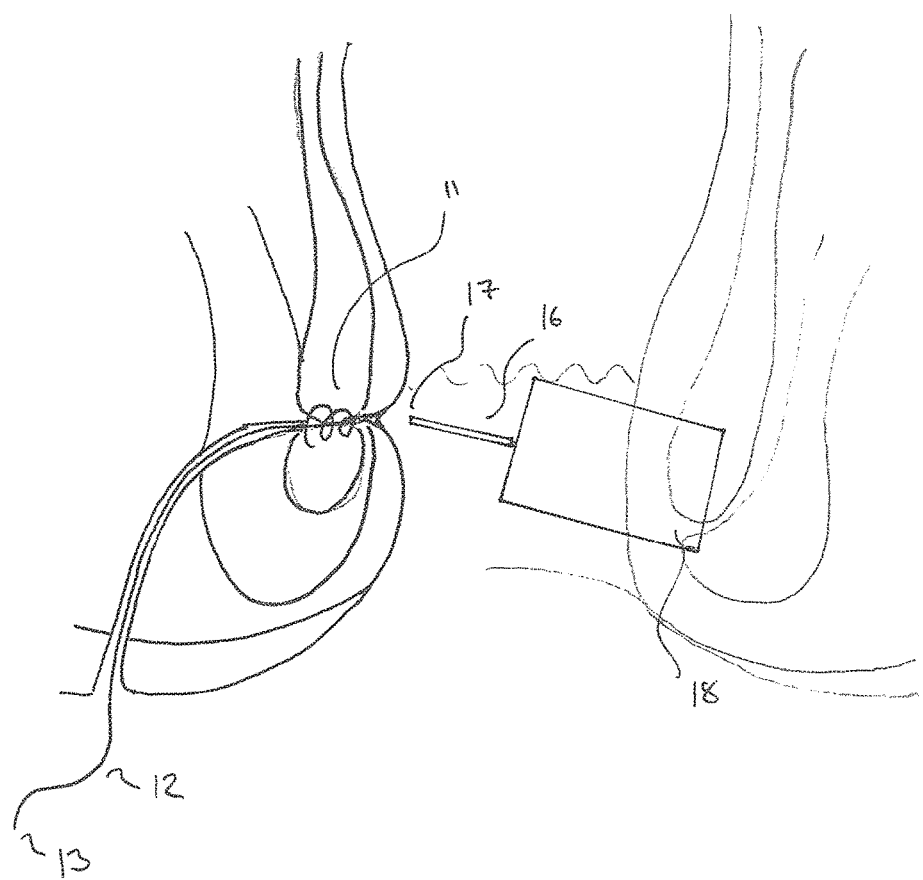
FIG. 5 is cross-sectional view of the device fully delivered into the sphincter muscle complex and detached from the delivery mechanism.

FIG. 5 illustrates the coil 11 completely delivered through and past the mucosal surface 20 and into the sphincter complex consisting of the internal 3 and external 4 sphincter muscles. The delivery mechanism interface 17 located distally on the delivery mechanism member 16 detaches from the tapered coil 11 and the delivery mechanism 18 is removed from the surgical field.

The mechanism of action of the delivery of the tapered coil results in sphincter muscle complex tissue being drawn into the centre of the coil 11 construct. The mechanism of action is illustrated in FIGS. 6-10.

Figure 6:
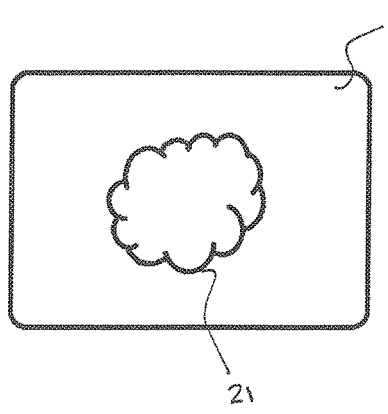
FIG. 6 is a plan view illustrating the internal opening of a fistula tract at the mucosal surface.
Figure 7:
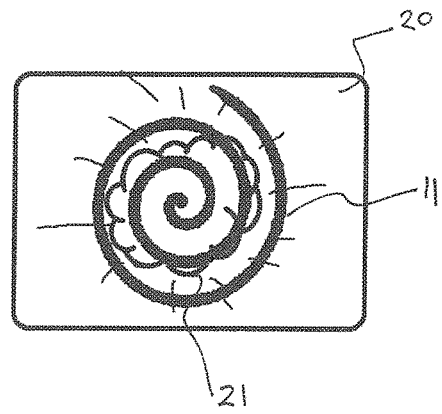
FIG. 7 is a plan view illustrating the device located at the internal opening of a fistula tract in apposition with the mucosal surface.
Figure 8:
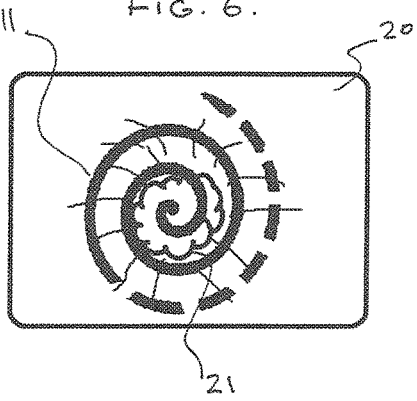
FIG. 8 is a plan view illustrating the device partially delivered through the mucosal surface and beginning to gather tissue internally to the device resulting in narrowing of the fistula internal opening.
Figure 9:
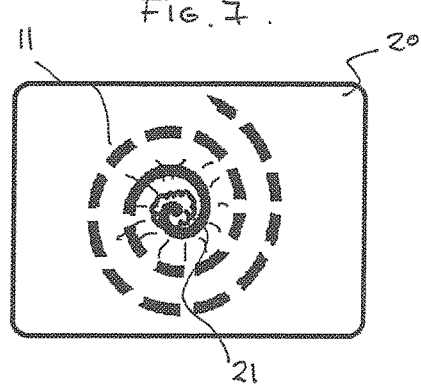
FIG. 9 is a plan view illustrating the device further delivered through the mucosal surface and into the sphincter muscle complex with further gathering of tissue internally to the device resulting in additional narrowing of the fistula internal opening.
Figure 10:
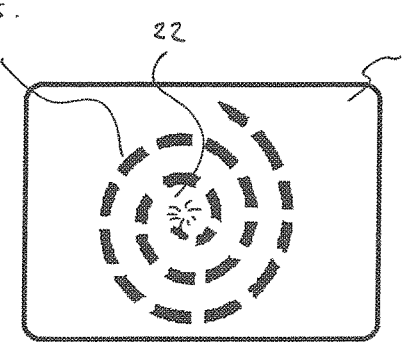
FIG. 10 is a plan view illustrating the device completely delivered sub-mucosally and entirely into the sphincter muscle complex with tissue internal to the device resulting in complete closure of the fistula internal opening.

FIG. 6 illustrates a plan view of an internal opening 21 of a fistula tract 6 located at the surface of the musical lining of the rectum 20 at the dentate line 5. FIG. 7 shows the closure coil 11 being brought into apposition to the musical surface 20 and being centred on the fistula tract 7 internal opening 21. As the closure coil 11 is delivered through the mucosal surface 20 and into the internal sphincter muscle 3 the sphincter muscle tissue begins to be gathered into the centre of the closure coil 11. FIG. 9 illustrates further delivery of the closure coil 11 resulting in an increased mass of sphincter muscle tissue being gathered internally in the coil. FIG. 10 illustrated complete delivery of the closure coil 11 entirely past the mucosal surface 20 and completely into the sphincter muscle complex including the internal 3 and external 4 sphincter muscles. The complete delivery of the coil 11 results in closure of the internal opening 21 of the fistula tract 6 by mechanism of gathering and compression of sphincter muscle tissue. This mechanism as described allows both the sphincter muscle tissue to knit together, and the mucosal surface to remodel to cover the site of delivery over a period of time, eventually resulting in complete resolution of the sphincter muscle defect associated with the internal opening of the fistula tract.

Figure 11:
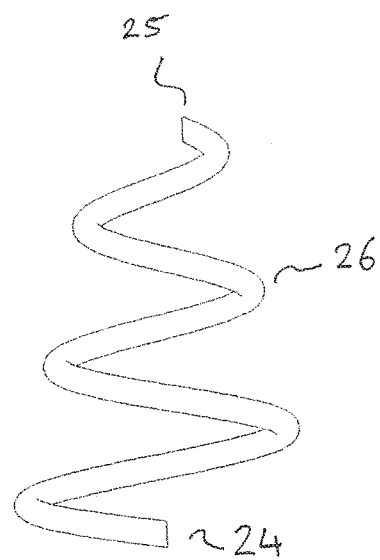
FIG. 11 is a front view of an embodiment of a perianal fistula treatment device.
Figure 12:
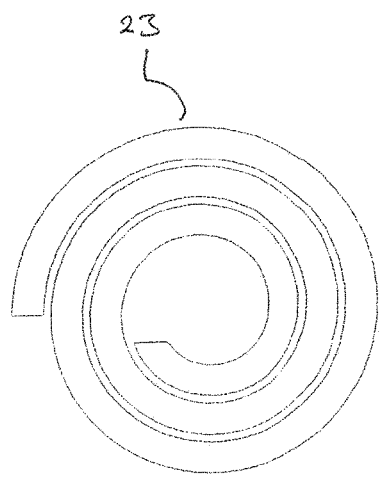
FIG. 12 is a plan view of the device of FIG. 11.
Figure 13:
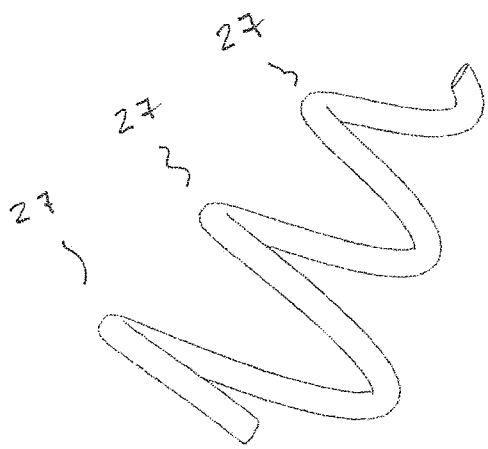
FIG. 13 is a side view of the device of FIGS. 11 and 12.
Figure 14:
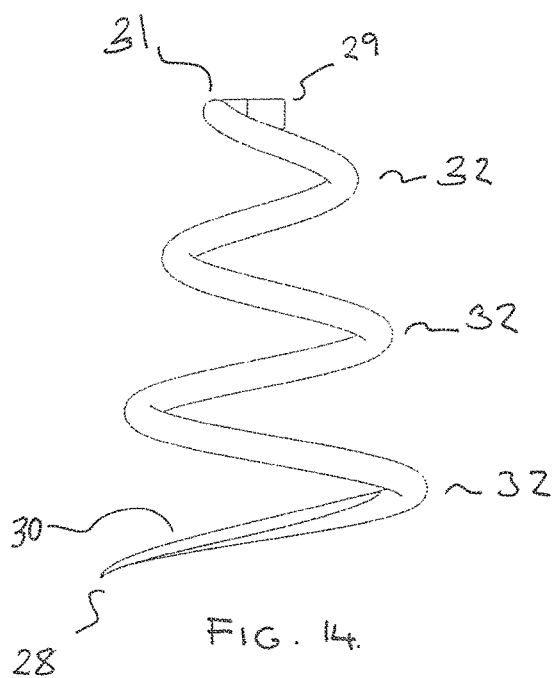
FIG. 14 is a front view of another fistula device with pointed tip.
Figure 15:
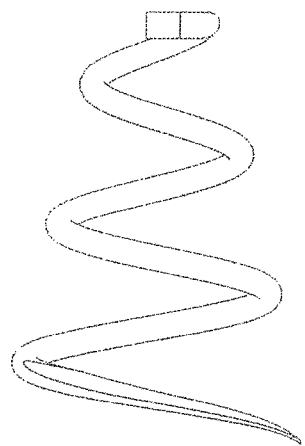
FIG. 15 is a side view of the device of FIG. 14.
Figure 16:
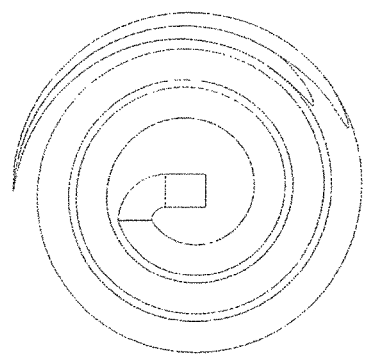
FIG. 16 is a plan view of the device of FIGS. 14 and 15.
Figure 17:
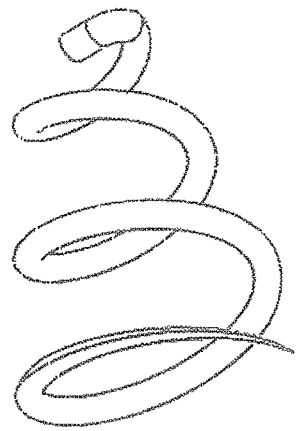
FIG. 17 is an isometric view of the device of FIGS. 14 to 16.
Figure 18:
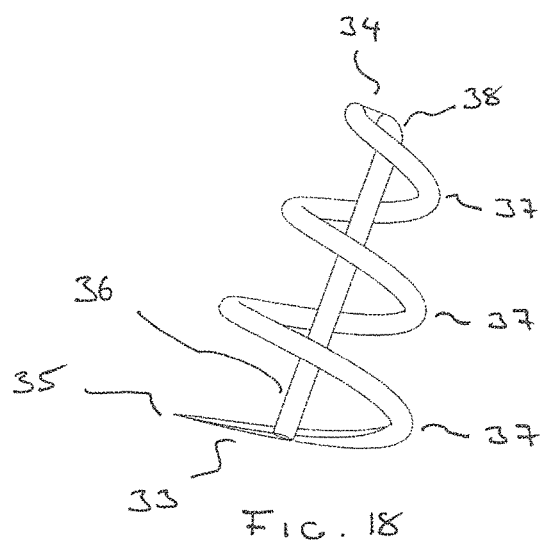
FIG. 18 is an isometric view of a further fistula treatment device with pointed tip and centre feature.
Figure 19:
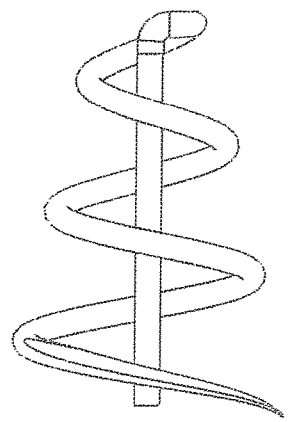
FIG. 19 is a front view of the device of FIG. 18.
Figure 20:
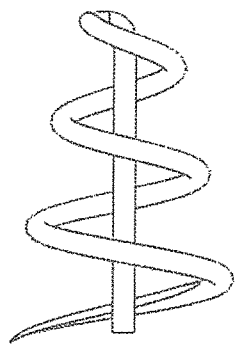
FIG. 20 is a side view of the device of FIGS. 18 and 19.
Figure 21:
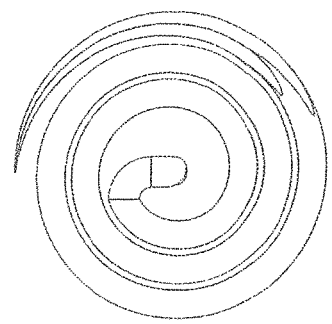
FIG. 21 is a plan view of the device of FIGS. 18 to 20.
Figure 24:
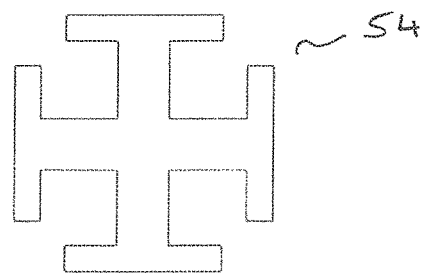
FIG. 24 is a cross-sectional view of a cross shape seton.
Figure 25:
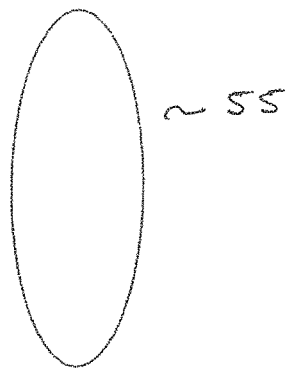
FIG. 25 is a cross-sectional view of an oval shape seton.
Figure 26:
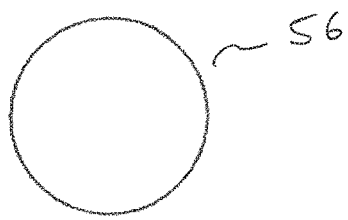
FIG. 26 is a cross-sectional view of a round shape seton.
Figure 27:
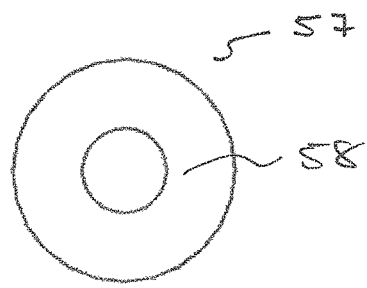
FIG. 27 is a cross-sectional view of a round hollow shape seton.

Referring to FIGS. 11 to 13 there is illustrated a tapered coil 12 which has a leading end 24 and a trailing end 25. The coil is in this case conical and decreases in lateral extent between the leading and trailing ends.

The implant is a coiled body structure. The leading end of the implant is the largest coil and initially surrounds the tissue defect with appropriate margin. As the implant is advanced the leading end provides a large surface area to effectively anchor the implant. Each subsequent coil provides (adds to) the anchoring and compression function. The smallest coil towards the trailing end provides the highest amount of tissue compression. As the implant is turned into the tissue each coil further compresses the captured tissue toward the center of the tissue defect, thus effectively completely compressing the surrounding tissue inwardly. The close approximation of tissue allows for the tissue to heal together. This compression provides an effective seal against the pressures generated in the rectum and prevents entering of passing faeces into the fistula tract thus preventing re-infection. The smaller diameters of the implant coils retain the captured tissue from separating and prevents the breakdown of the healing process or foreign material from entering the tissue defect. This is a major advantage over sutures and suture based surgical techniques such as the advancement flap (dermal flap) and the LIFT procedures.

The compression ensures close approximation of tissue throughout the center of the implant. At the most proximal surface the close approximation of tissue provides support to the healing mucosal lining of the rectum over the implant and tissue defect. Thus the healing tissue is fully supported by the implant during the healing process and is capable of surviving pressures of 150 mmHg and upwards of 200 mmHg which can be generated in the rectum.

The coil is delivered submucosal (at a predetermined depth) below the surface of the mucosa. This is to ensure that there is a full mucosal seal at the rectal mucosa surface to provide for a bacterial seal barrier. With the implant just below the surface the tissue is drawn inwards for complete compression and supports the mucosa healing process.

As the implant is turned into the tissue the compression becomes greater along the depth of the coil (progressive compression) and the length of the tract captured internal of the implant is compressed completely. This close approximation of tissue aids in the healing process.

Referring to FIGS. 14 to 17 it will be noted that in this case the tapered coil 12 has a pointed tissue insertion tip 28. The coil 12 also has a delivery mechanism interface feature 29.

FIGS. 18 to 21 illustrate another tapered coil 12 which also has a pointed tissue insertion tip 35 and a delivery mechanism interface feature 38. In this case the coil also has a centering feature 36. The centering feature 36 passes through the centre of the fistula tract and allows attachment of the drainage seton. The centering feature 36 allows centering of the coil in a concentric fashion to the fistula tract internal opening.

It will be appreciated that a coil device with a centering feature such as the centering feature 36 illustrated in FIGS. 18 to 21, with or without an attached seton, may be used to close fistula openings that may commonly occur in other areas of the body, such as: biliary (created during gallbladder surgery, connecting bile ducts to the surface of the skin), cervical (either an abnormal opening into the cervix or in the neck), craniosinus (between the space inside the skull and a nasal sinus), enterovaginal (between the bowel and vagina), faecal or anal (the faeces is discharged through an opening other than the anus), gastric (from the stomach to the surface of the skin), metroperitoneal (between the uterus and peritoneal cavity), umbilical (between the navel and gut). These fistulas may be:—blind also known as a sinus (open on one end only, but connects to two structures); complete (has both external and internal openings); horseshoe (connecting the anus to the surface of the skin after going around the rectum); or incomplete (a tube from the skin that is closed on the inside and does not connect to any internal structure).

FIG. 22 illustrates a coil device with a centre seton feature 44. In this embodiment the coil, centre feature and drainage seton are constructed from a single continuous monolithic structure.

FIG. 23 illustrates a coil which has a centre feature 50 with a seton attachment feature 51 at the distal end. A drainage seton 52 is attached to the feature 50.

It will be appreciated that the tapered coil may be of any suitable shape in transverse cross section. Some examples are illustrated in FIGS. 34 to 44. For example, the coil may be round, oval, triangular, multifaced or ribbon-like. In some cases the coil may be hollow.

The coil may be intended for subsequent removal or may be bioabsorbable.

Typical materials for the coil include

Bioabsorbable magnesium (including MgFe and other magnesium alloys) would be a material of choice because it offers the strength of stainless steel and similar metals, yet is bioabsorbable. MgFe alloys are well studied and have been used in medical products.

PLA) and PLGA (poly(lactic-co-glycolic acid)) are bioabsorbable polymers and would be a material of choice as they are commonly used bioabsorbable materials and have been well studied and used in medical products for over 70 years.

The coil may also be constructed from other common materials used for suture applications A bioabsorbable tapered coil would be beneficial to treatment of perianal fistulas due to the body's natural tendency to reject foreign materials.

The system of the invention also comprises a delivery device for the perianal fistula treatment device.

Figure 38:
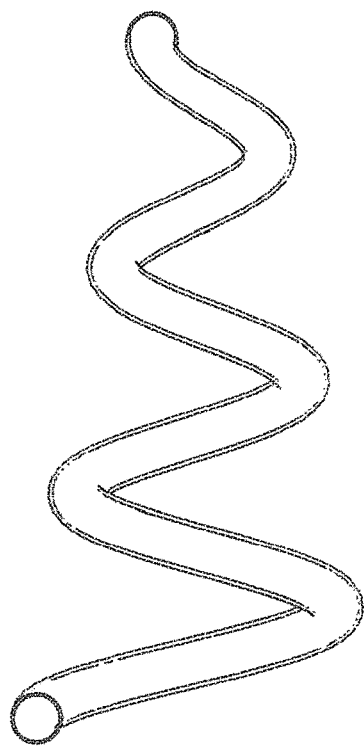
FIG. 38 is an isometric view of a hollow delivery mechanism of the tapered coil.
Figure 39:
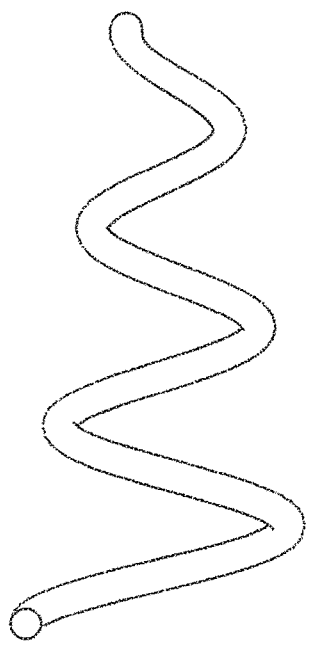
FIG. 39 is an isometric view of a solid coil to be delivered by the hollow delivery mechanism of FIG. 38.

The delivery device may comprise a hollow element such as illustrated in FIG. 38 through which the tapered coil is delivered. The hollow delivery element may comprise a coil. FIG. 39 illustrates a solid coil to be delivered by a hollow delivery element of FIG. 38 and FIG. 40 shows the hollow delivery element with the solid coil in place.

Figure 40:
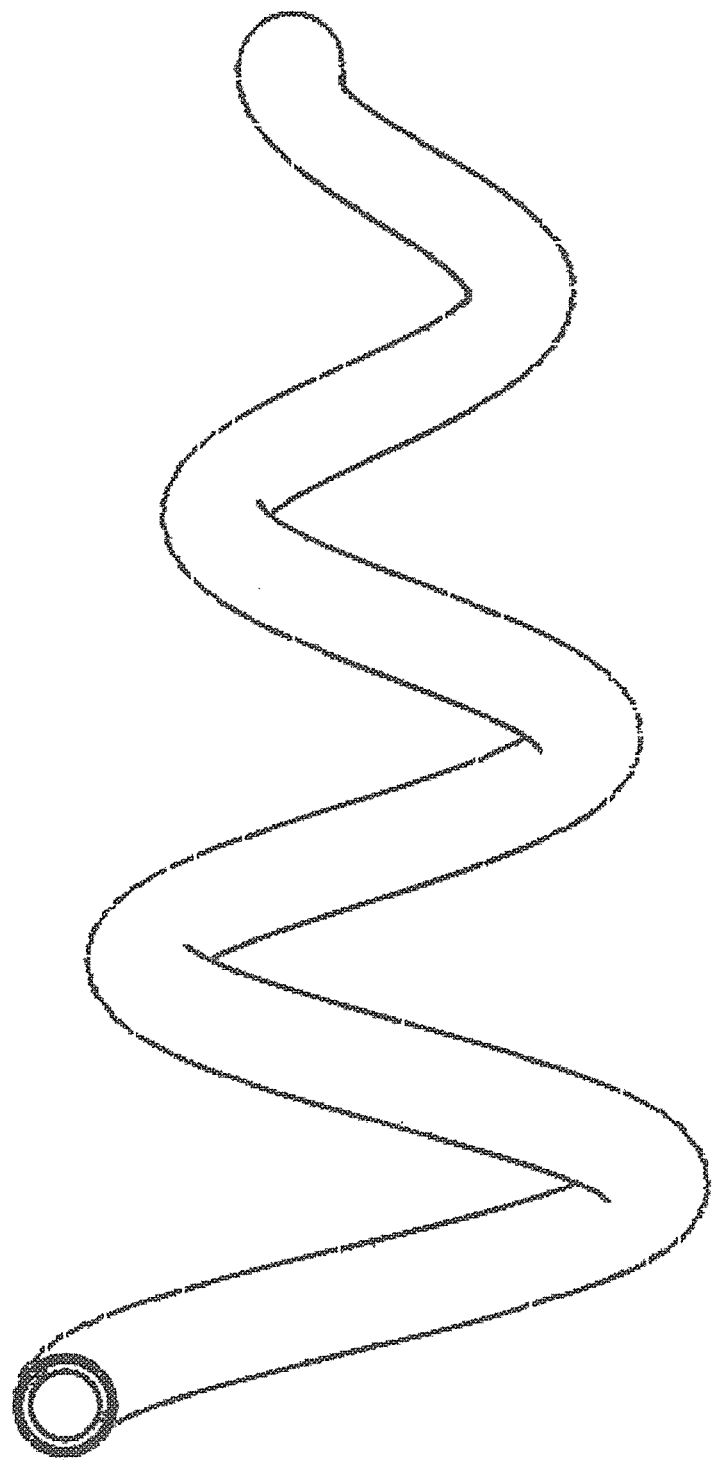
FIG. 40 is an isometric view of the hollow delivery mechanism of FIG. 38 and the solid coil of FIG. 39 in place.
Figure 41:
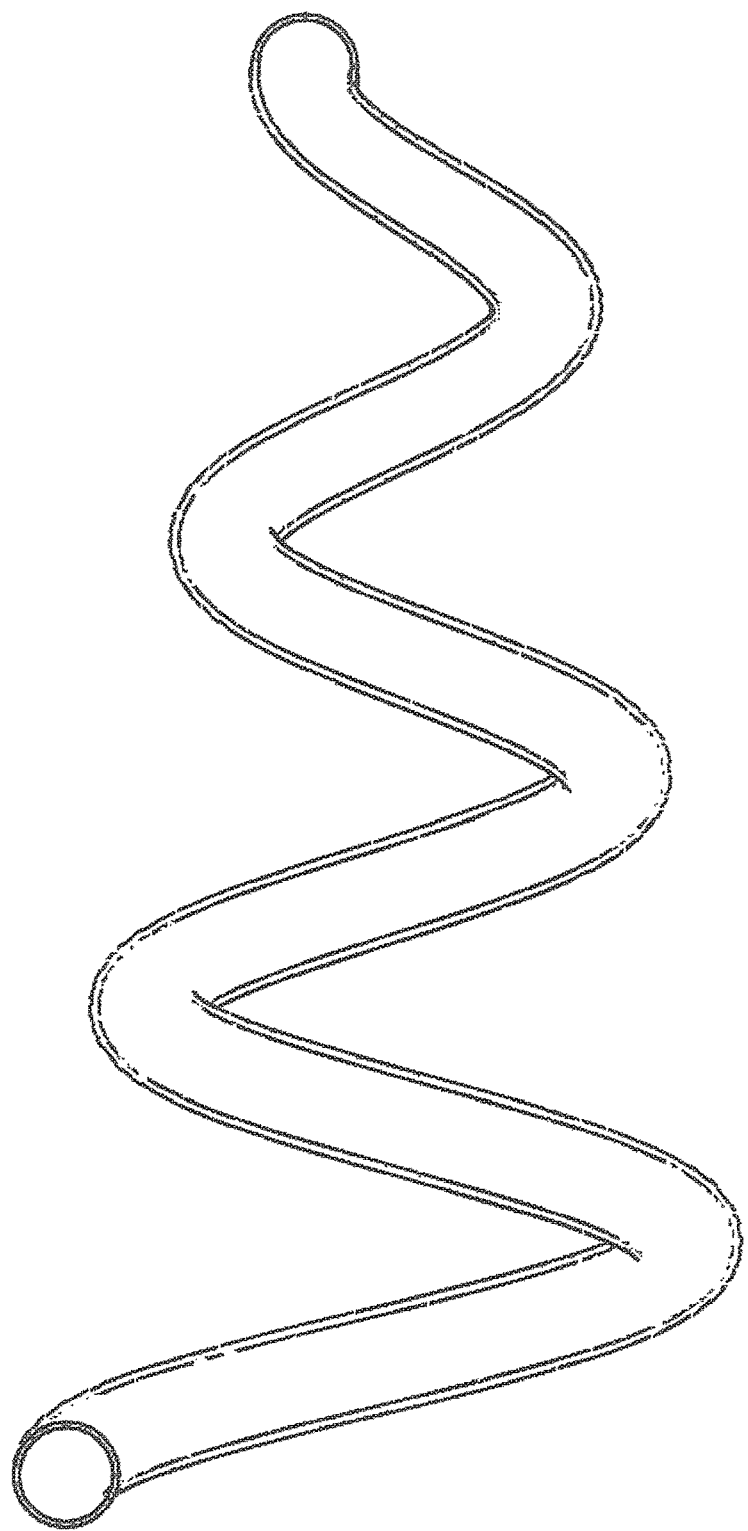
FIG. 41 is an isometric view of a solid core delivery mechanism with a hollow coil in place.

The system consists FIG. 40 of a hollow delivery element FIG. 38 that contains (houses) the implantable element FIG. 39. The implantable element FIG. 39 is housed in the delivery element FIG. 38 during the rotational delivery process. Once the delivery element FIG. 38 has reached the desired delivery position, it is uncoupled from the implantable element FIG. 39 and then rotated in the opposite direction of the direction of delivery (most commonly counter clockwise), leaving the implantable element FIG. 39 in place of the tissue bulk.

It will be appreciated that the system may be reversed with a hollow coil delivered over a solid delivery element.

In some cases the delivery device comprises a rail for the tapered coil. The rail and the coil may have interengagable features. Some examples are illustrated in FIGS. 42 to 44.

Figures 42, 43:
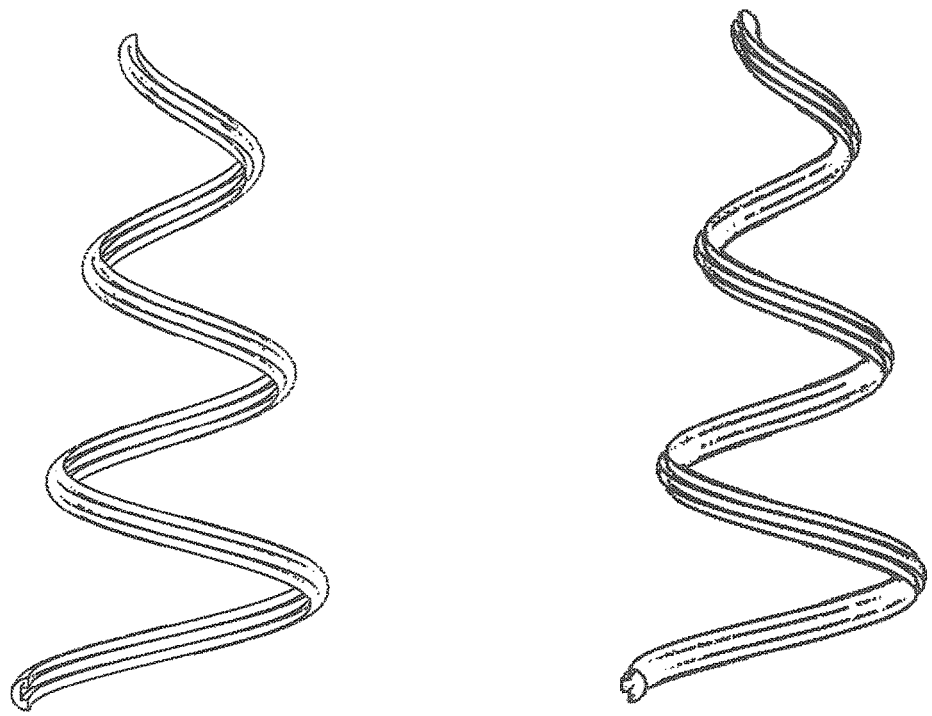
FIG. 42 is an isometric view of a rail support structure for delivering a mating coil.
FIG. 43 is an isometric view of a coil that mates with the support structure of FIG. 42.
Figure 44:
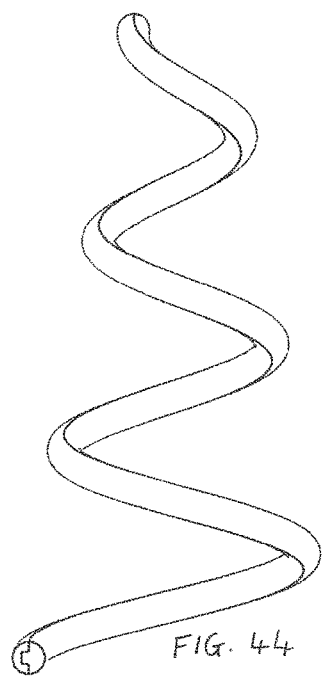
FIG. 44 is an isometric view of the combination of a coil and rail type delivery mechanism.

The rail system FIG. 44 consists of an outer implantable coil element FIG. 42, and an inner support rail element FIG. 43. The two elements interlock. The system FIG. 44 is rotated (most commonly in a clockwise direction) to the desired tissue depth. Upon the system FIG. 44 reaching the desired tissue depth, the elements are uncoupled FIG. 42 and the inner support rail is reversed out of the tissue bulk by rotation opposite in direction to insertion (commonly counter clockwise), leaving behind the outer implantable coil element FIG. 42 in place surrounding, compressing and closing the fistula tract.

It will be appreciated that the system may be reversed with an inner implantable coil delivered over an outer support rail.

Figure 48:
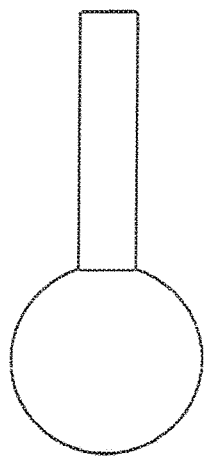
FIG. 48 illustrates a ball type centre feature seton attachment mechanism.

Ball Attachment FIG. 48:

The centre feature may have a ball feature along the shaft to aid in anchoring a seton that may be tied or looped around the centre feature. The ball provides a back stop where the knotted or looped seton will not detach from the centre feature.

Figure 49:
FIG. 49 illustrates a hook type centre feature seton attachment mechanism.

Hook Attachment FIG. 49:

The centre feature may have a hook feature along the shaft to aid in anchoring a seton that may be tied or looped around the centre feature. The hook provides a back stop where the knotted or looped seton will not detach from the centre feature.

Figure 50:
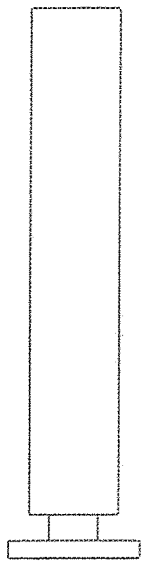
FIG. 50 illustrates a cleat type centre feature seton attachment mechanism.

Cleat Attachment FIG. 50:

The centre feature may have a cleat feature along the shaft to aid in anchoring a seton that may be tied or looped around the waist of the cleat feature. The cleat provides a back stop where the knotted or looped seton will not detach from the centre feature.

Figure 51:
FIG. 51 illustrates a hollow type centre feature seton attachment mechanism.
Figure 52:
FIG. 52 illustrates a hollow type centre feature seton attachment mechanism.

Internal to Centre Feature FIGS. 51 and 52

Figure 53:
FIG. 53 illustrates a swage type centre feature seton attachment mechanism.

The centre feature may be hollowed as in FIG. 51 and the seton may be placed in the hollowed portion. It may be glued or heat staked as shown in FIG. 52 or crimped as shown in FIG. 53.

Figure 54:
FIG. 54 illustrates a crimp type centre feature seton attachment mechanism.
Figure 55:
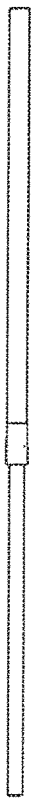
FIG. 55 illustrates a thermal bond type centre feature seton attachment mechanism.

Butt Joint FIG. 54:

The seton may be attached by a butt joint as shown in FIG. 55. The centre feature and seton are inserted into a tubular element with opposite ends facing each other as in FIG. 55. The three components may be joined by heating, glue as shown in FIG. 55, or by crimping/swaging as shown in FIG. 54. The join may have multiple crimp points along the tubular element to securely attach the seton and centre feature.

Figure 56:
FIG. 56 illustrates a butt joint type centre feature seton attachment mechanism.

Thermal Bond FIG. 56

The seton and centre feature may be thermally bonded/joined together as in FIG. 56, where both materials are made of a material with similar glass transition temperatures (Tg) and brought to their Tg and allowed to flow together creating a secure junction.

It will be appreciated that the embodiments of this system may also incorporate features such as previously described, including, but not limited to, a centre feature, a seton attachment feature, an integrated drainage seton and an integrated sharp tip located on the drive rail.

The seton 12 is used as a guidance and positioning mechanism and once the device is implanted serves as a means of fistula tract drainage. The seton 12 may be constructed of bioabsorbable materials, tissue healing enchantment properties, infection control agents and be constructed of part or composite of these materials.

After the fistula tract preparation, the seton 12 is attached using standard surgical technique to the existing surgical probe, suture, or seton already in place in the fistula tract. Once the seton 12 is attached, the system is pulled through the fistula tract proximally (towards the physician) until the coil device is adjacent to the tissue wall (rectal wall). The seton 12 ensures that the outer leading coil is centred around the outside of the fistula tract. Tension may be applied to the seton 12 as the coil is advanced into the tissue to aid in advancement and to maintain a centred position around the fistula tract.

The seton 12 is attached to the central portion of the coil 11. With the coil knitting together the sphincteric muscle and closing the fistula tract's internal opening the seton 12 maintains the proximal portion of the fistula tract's patency to facilitate drainage of any abscess, pus, and new accumulation of bodily fluids to prevent infection occurrence. The seton 12 prevents the tract from closing in on itself proximal of any fluid accumulation and acts as a conduit allowing material drainage between the wall of the tract and the outer wall of the seton 12. The seton 12 may also have a central lumen with tangential drainage holes entering from the external wall of the seton 12. The seton 12 may be constructed with a multi surface external wall to create channels and optimize the fluid drainage and prevent the fistula tract wall from occluding drainage around the seton. The seton 12 may be constructed of part or all elements as described and illustrated in FIGS. 24 to 33.

The seton 12 is constructed of materials that are strong enough to allow for surgical placement in the fistula tract. The seton 12 may be constructed of materials that are non-absorbable and meant to be removed at a later time. Alternatively, the seton 12 may be made of materials that bioabsorb throughout and upon completion of the fistula tract healing processes (examples include magnesium, PLA, PLGA). The seton 12 may be constructed of or include anti-infection agents to prevent infection of the fistula tract (silver ions, antibacterial agents). The seton 12 may be constructed of materials that aid in tissue growth (stem cell, collagen matrix). The seton 12 may be constructed of part or all elements as described.

Figure 28:
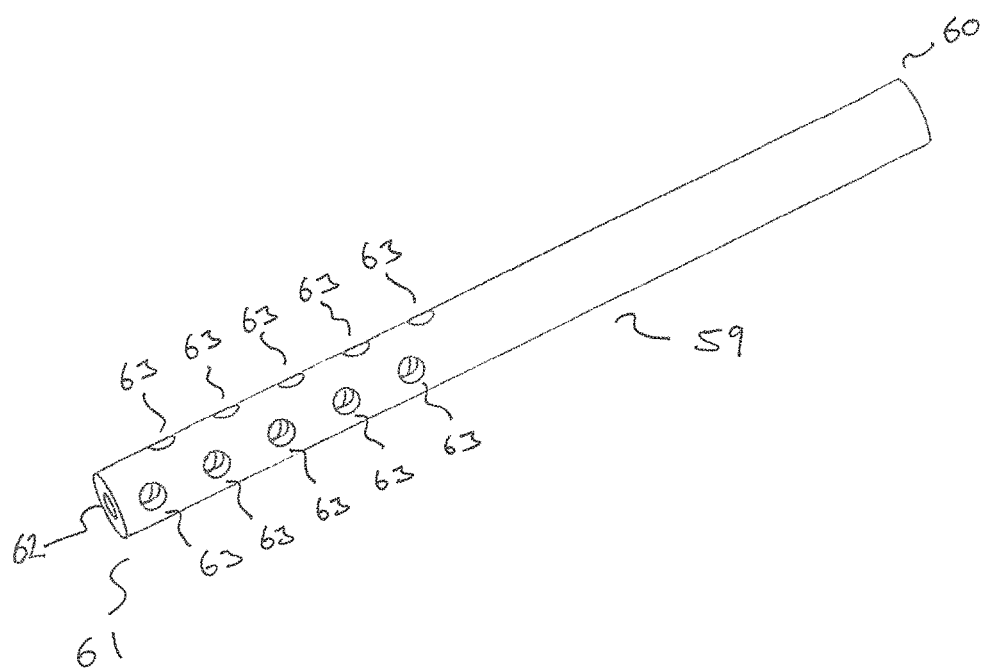
FIG. 28 is an isometric view of a round hollow perforated embodiment of a seton.
Figure 29:
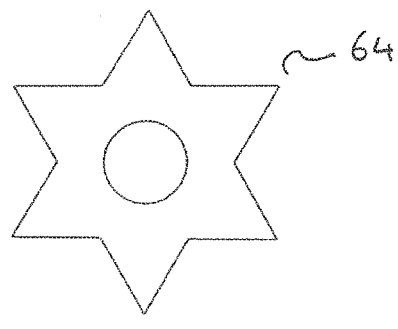
FIG. 29 is a cross-sectional view of a hollow star shape seton.
Figure 30:
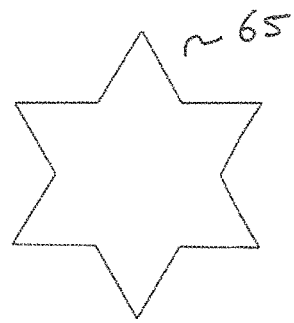
FIG. 30 is a cross-sectional view of a star shape seton.
Figure 31:
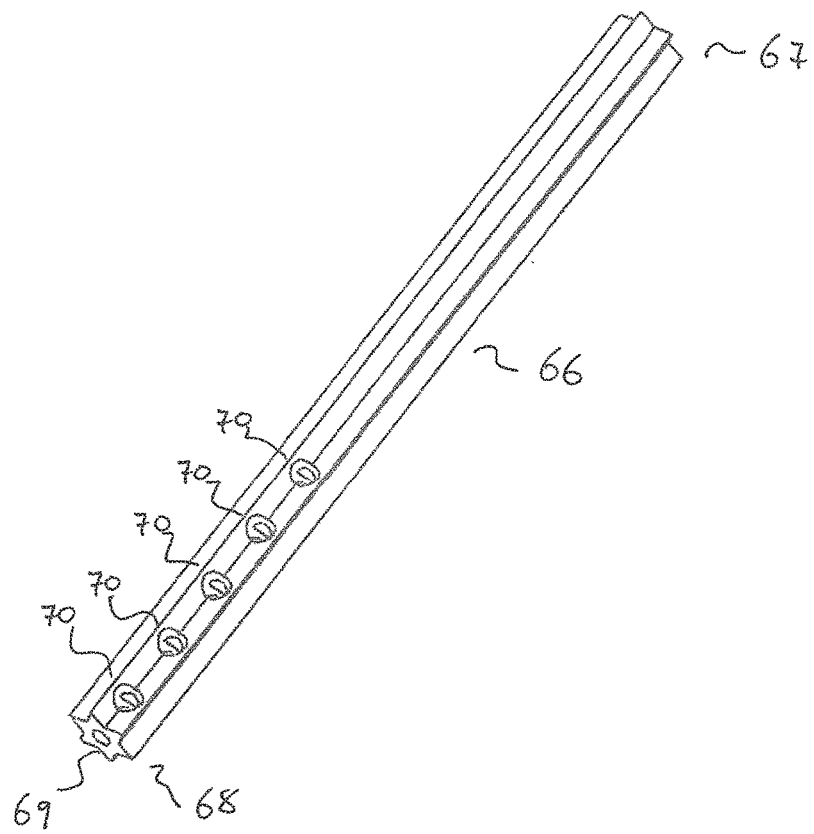
FIG. 31 is an isometric view of a star shape hollow perforated embodiment of a seton.
Figure 32:
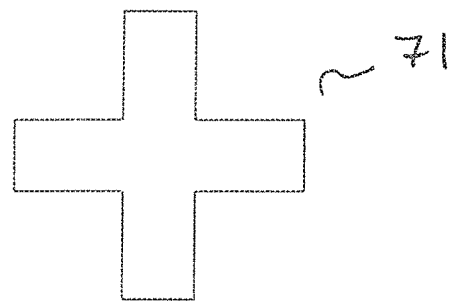
FIG. 32 is a cross-sectional view of a cross shape seton.
Figure 33:
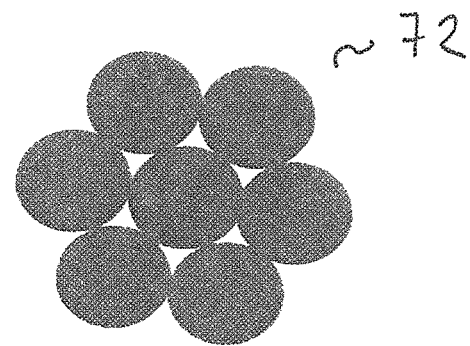
FIG. 33 is a cross-sectional view of a multi-braid embodiment of a seton.
Figure 34:
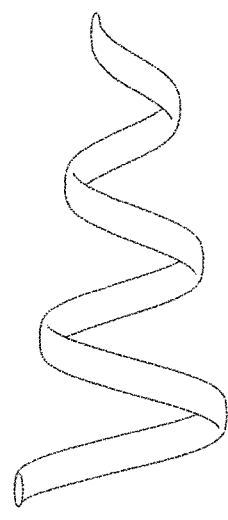
FIG. 34 is an isometric view of an oval cross-section embodiment of the closure coil device.
Figure 35:
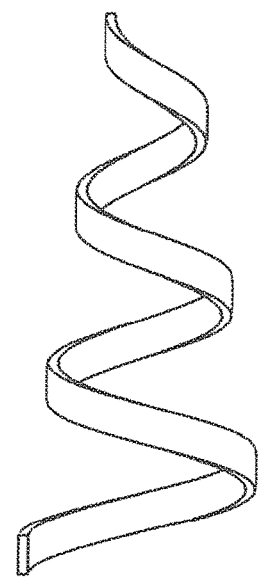
FIG. 35 is an isometric view of a ribbon type tapered coil of a perianal fistula treatment device.
Figure 36:
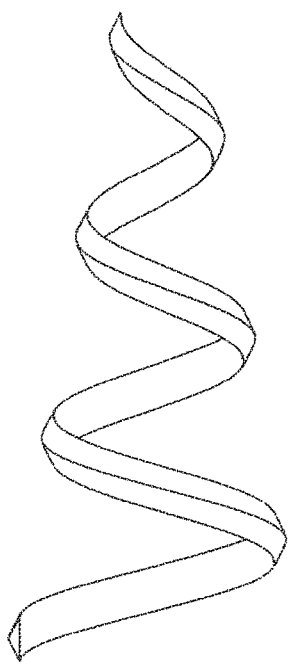
FIG. 36 is an isometric view of a triangular cross-section embodiment of a tapered coil.
Figure 37:
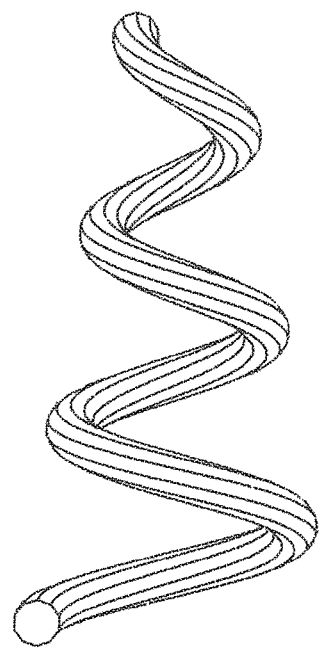
FIG. 37 is an isometric view of a multi-faced cross-section embodiment of the tapered coil.

The seton may be of any suitable shape in cross section such as round, oval, cross shape, star or braid as illustrated in FIGS. 24 to 26 and FIGS. 30, 32, 33. In all cases the seton may be hollow as illustrated in FIGS. 27, 28, 29 and 31 to further enhance drainage. The seton may have peripheral holes as illustrated in FIGS. 28 and 31 to provide for increased drainage effectivity. The holes allow additional surfaces of drainage, by increasing drainage surface area/channels the fluid drains more quickly and reduces the chance that any of the channels will become occluded and prevent fluid drainage at the same moment in time.

Figure 46:
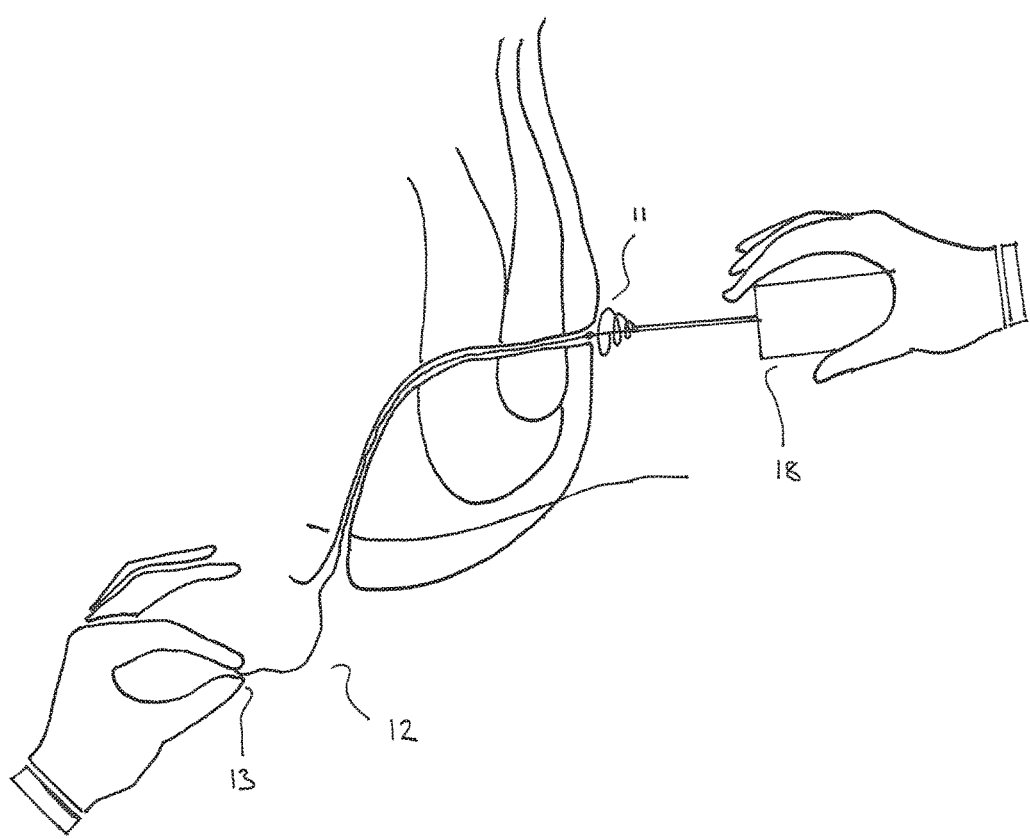
FIG. 46 illustrates the delivery of the system through the fistula tract prior to deployment of the coil.

FIG. 46 illustrates the delivery of the system through the fistula tract prior to deployment of the coil. The seton, attached to the centre feature allows the coil to be drawn into apposition against the mucosal wall, and located concentric to the fistula tract internal opening.

Figure 47:
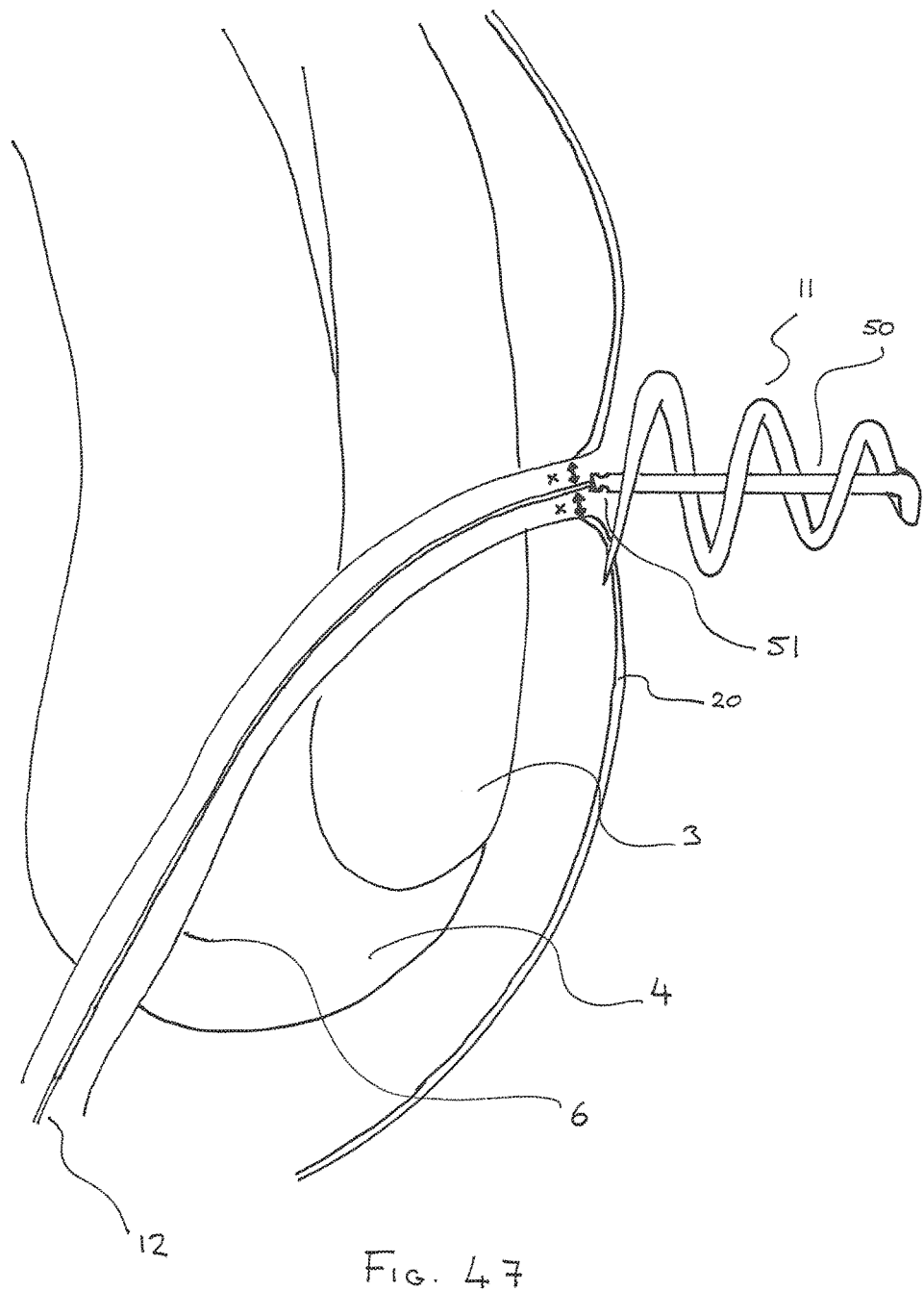
FIG. 47 illustrates the position of the coil prior to deployment.

FIG. 47 illustrates the position of the coil prior to deployment and demonstrates the effect of the centering feature in combination with the seton in positioning the coil concentrically around the fistula tract internal opening. (Dimensions 'x' being equal).

As noted above, one or other or both of the coil and seton may comprise bioabsorbable materials.

Typical materials for the coil include:
Bioabsorbable magnesium (including MgFe and other magnesium alloys) is one material of choice because it offers the strength of stainless steel and similar metals, yet is bioabsorbable. MgFe alloys are well studied and have been used in medical products.
Synthetic bioabsorbable materials may include PLA and PLGA (poly (lactic-co-glycolic acid)) (PLGA, PCL, Polyorthoesters, Poly(dioxanone), Poly(anhydrides), Poly(trimethylene carbonate), Polyphosphazenes), and or natural bioabsorbable materials may include fibrin, collagen, chitosan, gelatin, Hyaluronan are bioabsorbable polymers and would be a material of choice as they are commonly used bioabsorbable materials and have been well studied and used in medical products for over 70 years.

For example, companies such as Ethicon market a number of such products with different absorption rates such as http://www.ethicon.com/healthcare-professionals/products/. Absorbable polymer materials are also available from medical material companies such as Zeus, see http://www.zeus-inc.com/advanced-products/absorv-bioabsorbables.

Typical materials for the seton include:
Bioabsorbable magnesium (including MgFe and other magnesium alloys) is one material of choice because it offers the strength of stainless steel and similar metals, yet is bioabsorbable. MgFe alloys are well studied and have been used in medical products.
Synthetic bioabsorbable materials may include PLA and PLGA (poly(lactic-co-glycolic acid)) (PLGA, PCL, Polyorthoesters, Poly(dioxanone), Poly(anhydrides), Poly(trimethylene carbonate), Polyphosphazenes), and or natural bioabsorbable materials may include fibrin, collagen, chitosan, gelatin, Hyaluronan are bioabsorbable polymers and would be a material of choice as they are commonly used bioabsorbable materials and have been well studied and used in medical products for over 70 years.

In one case both the coil and the seton are bioabsorbable, and the seton degrades prior to the degradation of the coil. This may be achieved in a number of different ways, such as the seton being of a different bioabsorbable material to the coil.

For example the coil implant may be constructed of PLLA which degrades slowly, typically within 18 to 36 months depending on formulation, cross section, and surface modifications, and the Seton drain may be constructed of PLGA (85L/15G) which typically degrades "faster" in 1 to 2 months depending on formulation, cross section, and surface modifications Another method of altering the time of degradation (degradation (absorption) properties) is by providing a reduced cross sectional area, more porosity, less crystallinity, more reactive hydrolytic groups in the backbone, more hydrophilic end groups, and/or more hydrophilic backbone.

In one case, the seton begins to absorb 5 weeks post-surgical implantation. This is variable depending upon the healing time of the patient, with full healing usually occurring within a 5 to week period. By way of example the coil implant may remain for a period of at least 10 weeks after healing and may degrade over a 6 to 18 month time period from the date of implantation.

Advantageously, the closure mechanism of the device is maintained during the entire healing process. In some cases the coil remains in situ to withstand rectal pressures and maintain closure of internal tract opening for at least 10 weeks to prevent re-opening of the tract.

The coil implant may remain in place longer to allow full healing of the internal opening of the fistula tract. The seton drain may degrade at a faster rate compared to the coil implant so long as the seton drain is in place for a long enough time for all remaining abscess and infection, to drain from the fistula tract and any side branches. It is advantageous that the seton drain absorbs faster than the coil so that the patient does not have any visually remnant feature of the device or thoughts of fistula. The seton is not needed for as long a period as the coil implant, with the seton drain absorbing faster than the implant, the patient will not have to return to the surgeon for removal during the internal opening healing process.

Also, the implant remains in place for a long enough period of time (e.g. greater than 1 week) to allow remodelling of the defect in the mucosa and formation of a mucosal layer. This mucosal layer acts as a bacterial seal preventing reinfection of the tract from entering of fasces. The reformation of the musical layer in conjunction with the sphincter muscle closure mechanism prevents fasces entering the tract.

The implant coil and draining seton may be doped or loaded with healing and antimicrobial agents (such as stem cell, silver ions, silver particles, antibiotics, antibacterial agents and the like).

The seton may be of differential bioabsorption wherein the seton is absorbed at a different rate along its length.

The seton may be of differential bioabsorption wherein the distal portion of the drain absorbs more quickly than the proximal portion. This differential absorption of the seton results in the seton remaining attached to the coil via the proximate portion until fully absorbed. Advantageously, this allows for the external opening to close and remove the chance of the seton being pulled out through the external opening.

The seton may also be of differential bioabsorption wherein the proximal portion of the seton absorbs more quickly—in this case the anchoring mechanism of the closure device with relation to the seton could be broken at an earlier time than the full seton absorption allowing the seton to be removed (by the patient or doctor or naturally fall out) through the external opening.

In both differential absorption embodiments, the entire seton would have to remain in place for full healing (and drainage) time of the tract (e.g. 10 weeks).

The bioabsorbable materials used in the construction of the implant coil, or drainage seton, or both, can be both natural or synthetic polymers such as those listed below.

Natural Polymers
Fibrin
Collagen
Chitosan
Gelatin
Hyaluronan
Synthetic Polymers
PLA, PGA, PLGA, PCL, Polyorthoesters
Poly(dioxanone)
Poly(anhydrides)
Poly(trimethylene carbonate)
Polyphosphazenes The selection of the material used can be made whilst taking the following factors into account.

Factors that Accelerate Polymer Degradation:
More hydrophilic backbone.
More hydrophilic endgroups.
More reactive hydrolytic groups in the backbone.
Less crystallinity.
More porosity.
Smaller device size.

The implant coil of the invention may be delivered by a number of techniques. In one case the coil is delivered by a coil delivery mechanism. In this case, the implant coil may have an interface region for interfacing with the delivery mechanism.

Figure 57:
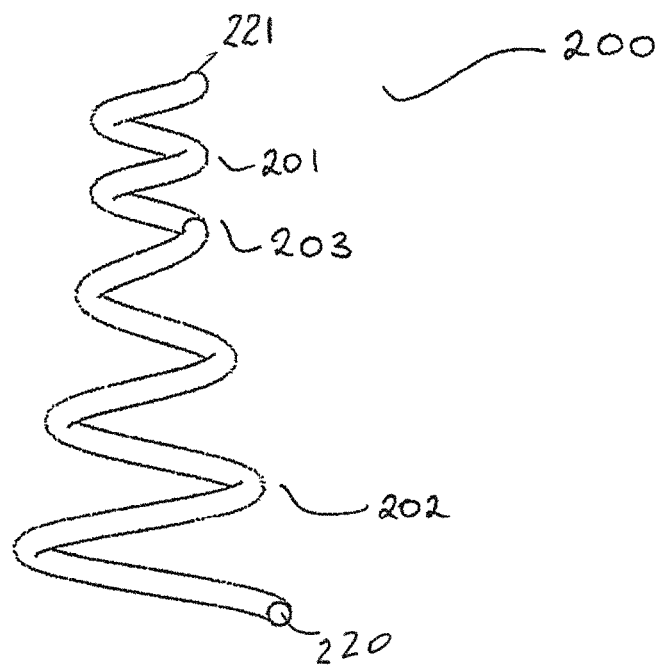
FIG. 57 is an isometric view of a coil with a partially straight section.

A perianal fistula treatment device may comprise an implant coil having a tapered portion which is configured for insertion into bulk tissue surrounding a fistula. The implant coil may have a driver interface portion which is configured for engagement with a driver implement for rotation of the coil to draw tissue surrounding a fistula inwardly. The advantages of such an implant coil are:

Ability to be delivered deep into the sphincter muscle complex allowing for greater anchoring and sphincter muscle apposition at the muscle defect Ability to disengage from the delivery mechanism in a spiral nature, allowing reversing of the delivery mechanism through the same tract as delivery preventing further damage to the tissue Prevents the mucuosa of the rectum being pulled down towards the sphincter muscle complex Ability to be delivered through and past the anoderm resulting in lower pain due to interference with the nerve endings of the anoderm Prevention of bacterial tracking by delivering deep sub mucosally allowing a new mucosal lining to form at the fistula internal opening One such implant coil 200 is illustrated in FIG. 57 and comprises a tapered section 202 and a driver interface portion which in this case is provided by straight coil section 201 which has a substantially uniform lateral extent along a length thereof. The implant coil 200 has a leading end 220, a transition region 203 and a trailing end 221. The tapered portion 202 of the coil extends from the leading end 220 to the transition region 203 and the driver interface portion 201 extends from the transition region 203 to the trailing end 221. It will be noted that, as described in other embodiments, the tapered portion of the coil decreases in lateral extent between the leading end 220 and the transition region 203. The leading end 220 may have a pointed tissue insertion tip as illustrated, for example, in FIGS. 14 to 17.

The implant is a coiled body structure. The leading end of the implant is the largest coil and initially surrounds the tissue defect with appropriate margin. As the implant is advanced the leading end provides a large surface area to effectively anchor the implant. Each subsequent coil provides (adds to) the anchoring and compression function. The smallest coil towards the trailing end provides the highest amount of tissue compression. As the implant is turned into the tissue each coil further compresses the captured tissue toward the center of the tissue defect, thus effectively completely compressing the surrounding tissue inwardly. The close approximation of tissue allows for the tissue to heal together. This compression provides an effective seal against the pressures generated in the rectum and prevents entering of passing faeces into the fistula tract thus preventing re-infection. The smaller diameters of the implant coils retain the captured tissue from separating and prevents the breakdown of the healing process or foreign material from entering the tissue defect. This is a major advantage over sutures and suture based surgical techniques such as the advancement flap (dermal flap) and the LIFT procedures.

The compression ensures close approximation of tissue throughout the center of the implant. At the most proximal surface the close approximation of tissue provides support to the healing mucosal lining of the rectum over the implant and tissue defect. Thus the healing tissue is fully supported by the implant during the healing process and is capable of surviving pressures of 150 mmHg and upwards of 200 mmHg which can be generated in the rectum.

The coil is delivered submucosal (at a predetermined depth) below the surface of the mucosa. This ensures that there is a full mucosal seal at the rectal mucosa surface to provide for a bacterial seal barrier. With the implant just below the surface the tissue is drawn inwards for complete compression and supports the mucosa healing process.

As the implant is turned into the tissue the compression becomes greater along the depth of the coil (progressive compression) and the length of the tract captured internal of the implant is compressed completely. This close approximation of tissue aids in the healing process.

In this and other embodiments the implant body is in the form of an open tapered coil body (for example, without a cross bar or other centering feature) in which the leading edge, (into the muscle) is of a larger diameter than the trailing edge, (rectum surface). The trailing portion is of smaller diameter than the leading portion. The coil is of open form, therefore there is no inward protrusion at either the proximal nor distal end of the body. This open form factor enables the implant to be driven into the tissue body to a pre-determined depth (depending on the taper) which results in progressive tissue compression.

At least the driver interface portion of the implant coil is solid and in some cases all of the implant coil is solid. Alternatively, as described above and below, the implant coil or at least part thereof may be hollow.

In this embodiment, preferably the treatment device also includes a seton of the type described above. In some cases the seton is not mounted or attached to the implant coil during delivery but may be attached so as to extend from the coil when the coil is in situ. In some cases the seton may be embedded in the sphincter muscle complex and lead so that the end of the seton protrudes through the external opening of the fistula tract.

The implant is delivered using any suitable delivery device as described. In one case the delivery device comprises a driver implement which interfaces with the implant coil and is used to rotate the coil to draw tissue surrounding a fistula inwardly. The driver implement preferably interfaces with the driver interface of the implant coil.

In some cases the driver implement comprises a driver coil which is configured for engagement with the driver interface of the implant coil. The driver coil may have a substantially uniform lateral extent along a length thereof for engagement with the corresponding driver interface portion of the implant coil.

Figure 58:
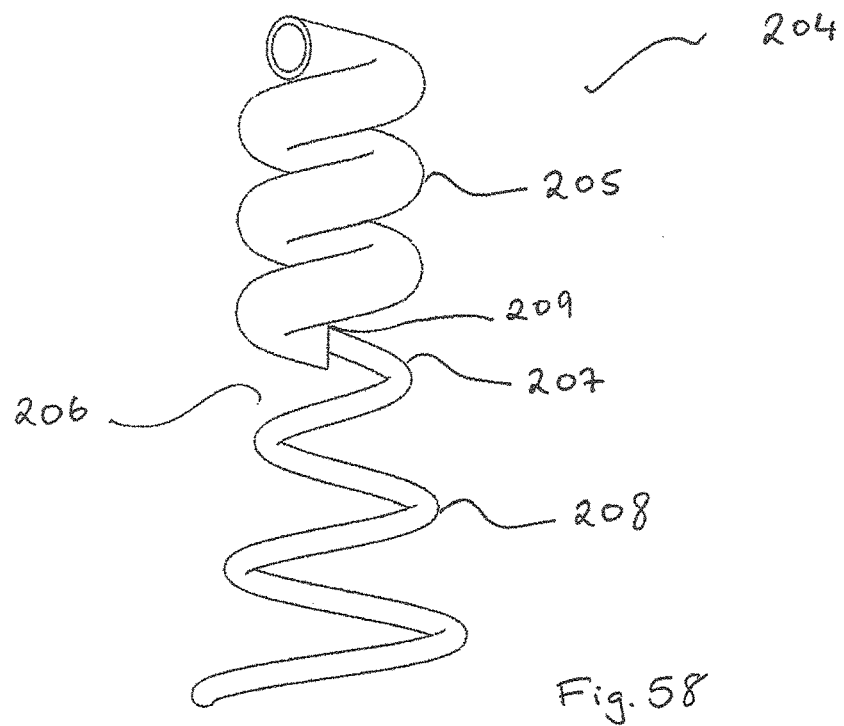
FIG. 58 and FIG. 59 are isometric views of a hollow coil delivery mechanism interfaced with a solid coil.
Figure 59:
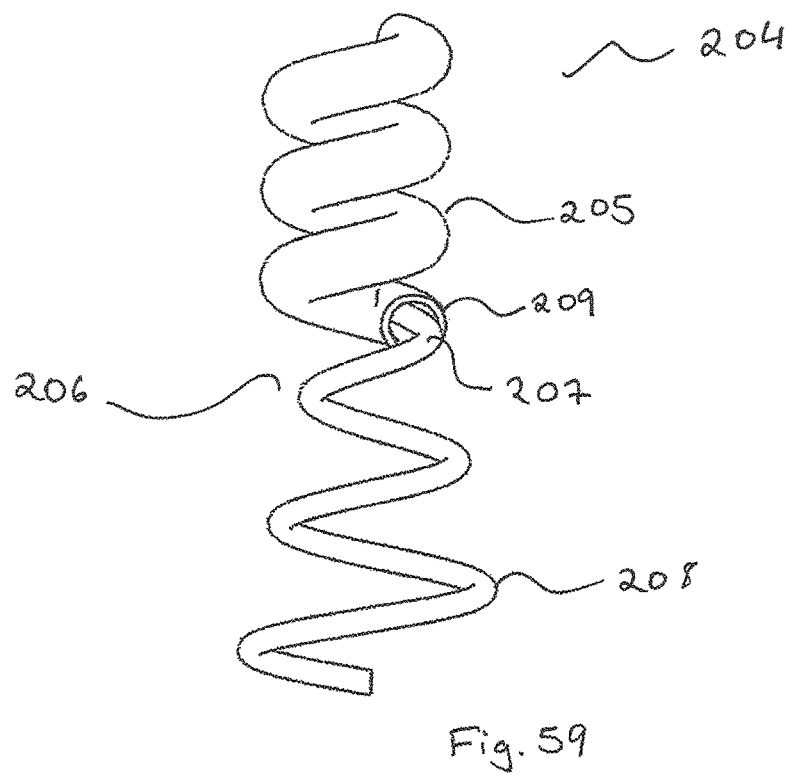

In one embodiment as illustrated in FIGS. 58 and 59 a driver coil 205 is hollow for interfacing with the interface portion 201 of the implant coil.

FIGS. 58 and 59 illustrate an assembly 204 in which a solid implant coil 206 is delivered by a straight hollow delivery coil 205. The coil implant 206 has a straight profile section 207 and a tapered section 208. The straight profile section 207 fits within the internal channel of the delivery coil 205 up to the interface 209, whereby the hollow coil 205 is rotated which in turn rotates the implant coil 206 for delivery.

The hollow sections of the delivery coil in all cases may comprise a single turn, multiple turns or part thereof or the entire construct.

Figure 60:
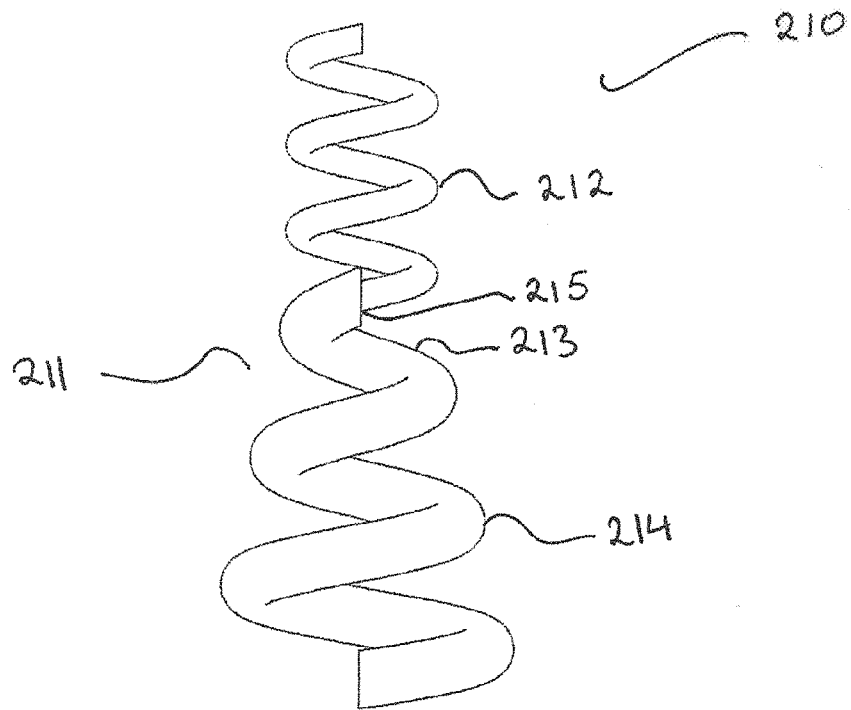
FIG. 60 and FIG. 61 are isometric views of a solid coil delivery mechanism interfaced with a hollow coil.
Figure 61:
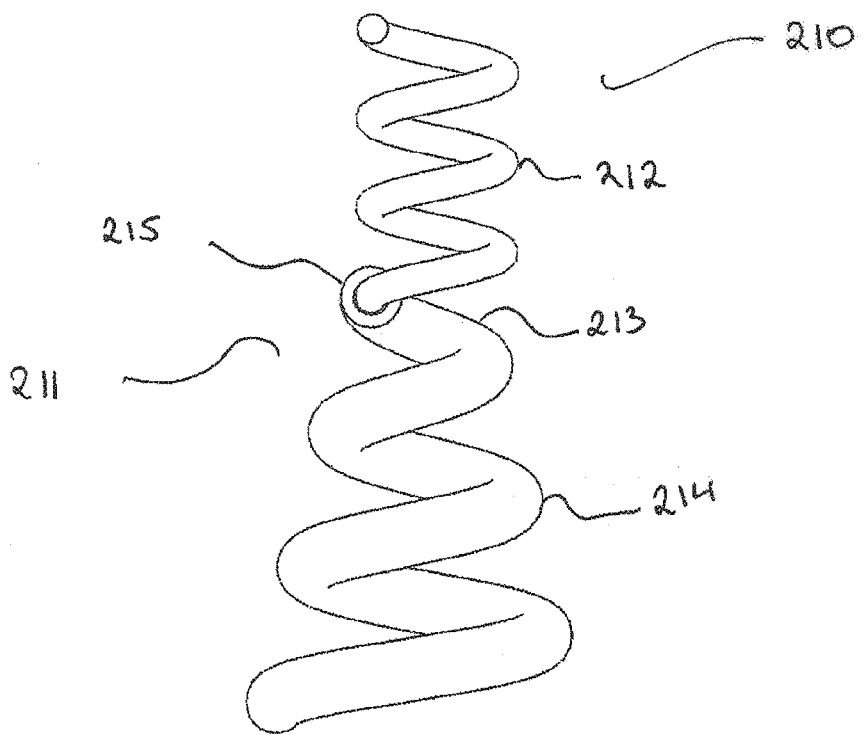
Figure 62:
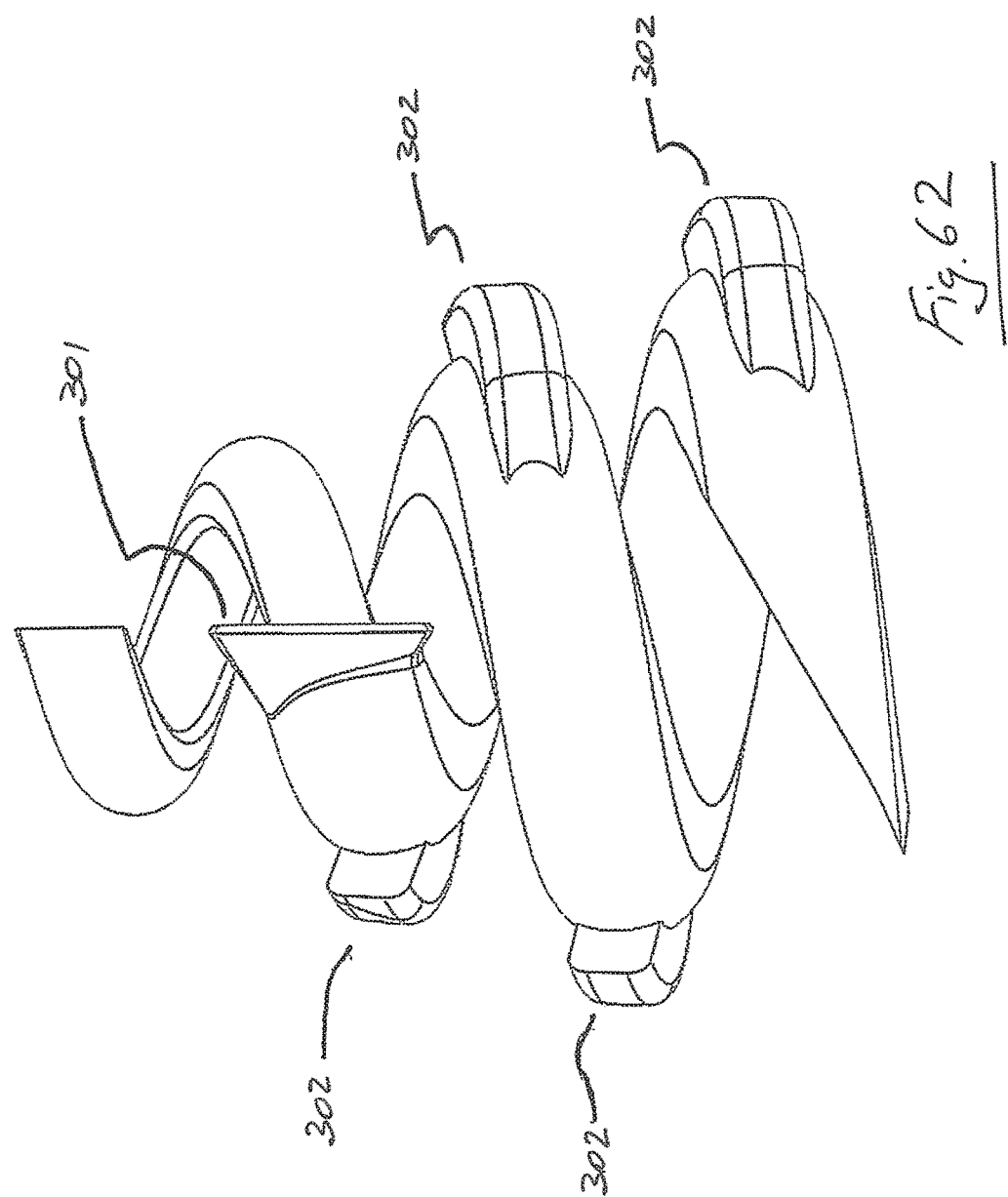
FIGS. 62 and 63 are isometric views of another fistula treatment device according to the invention.
Figure 63:
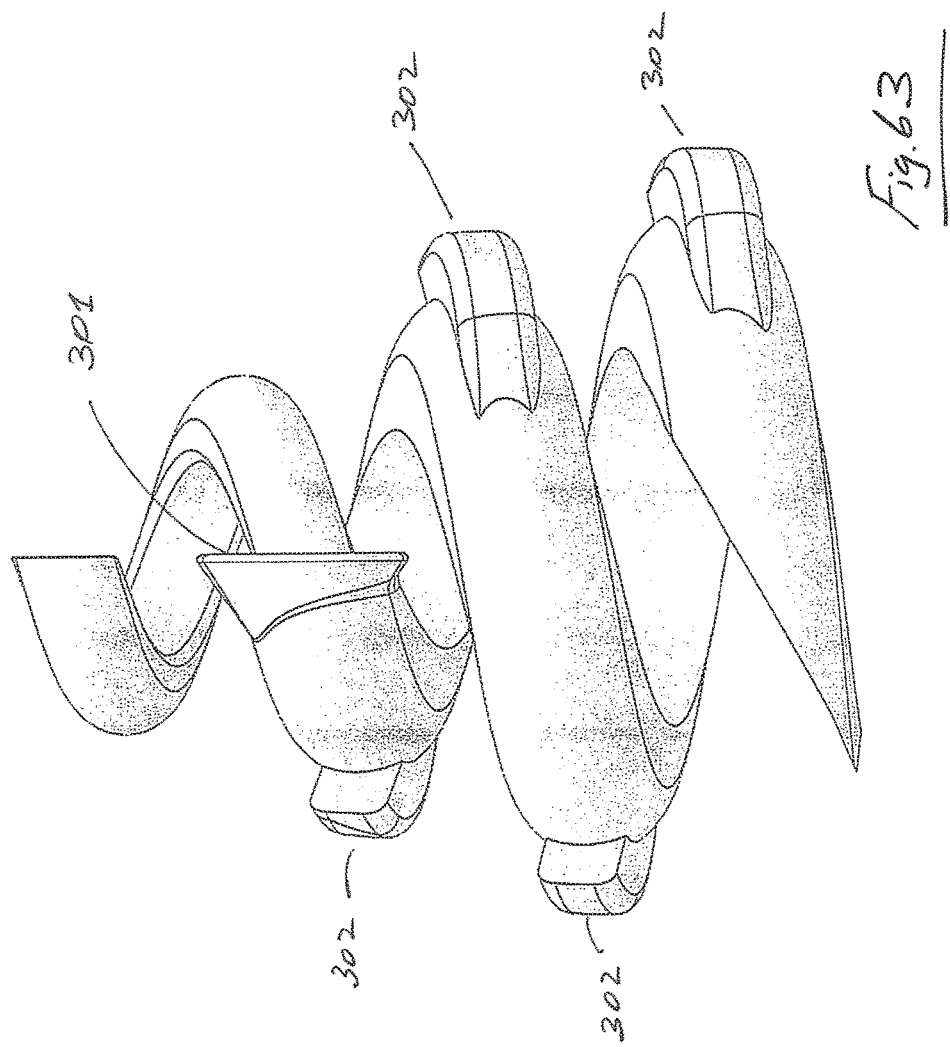
Figure 64:
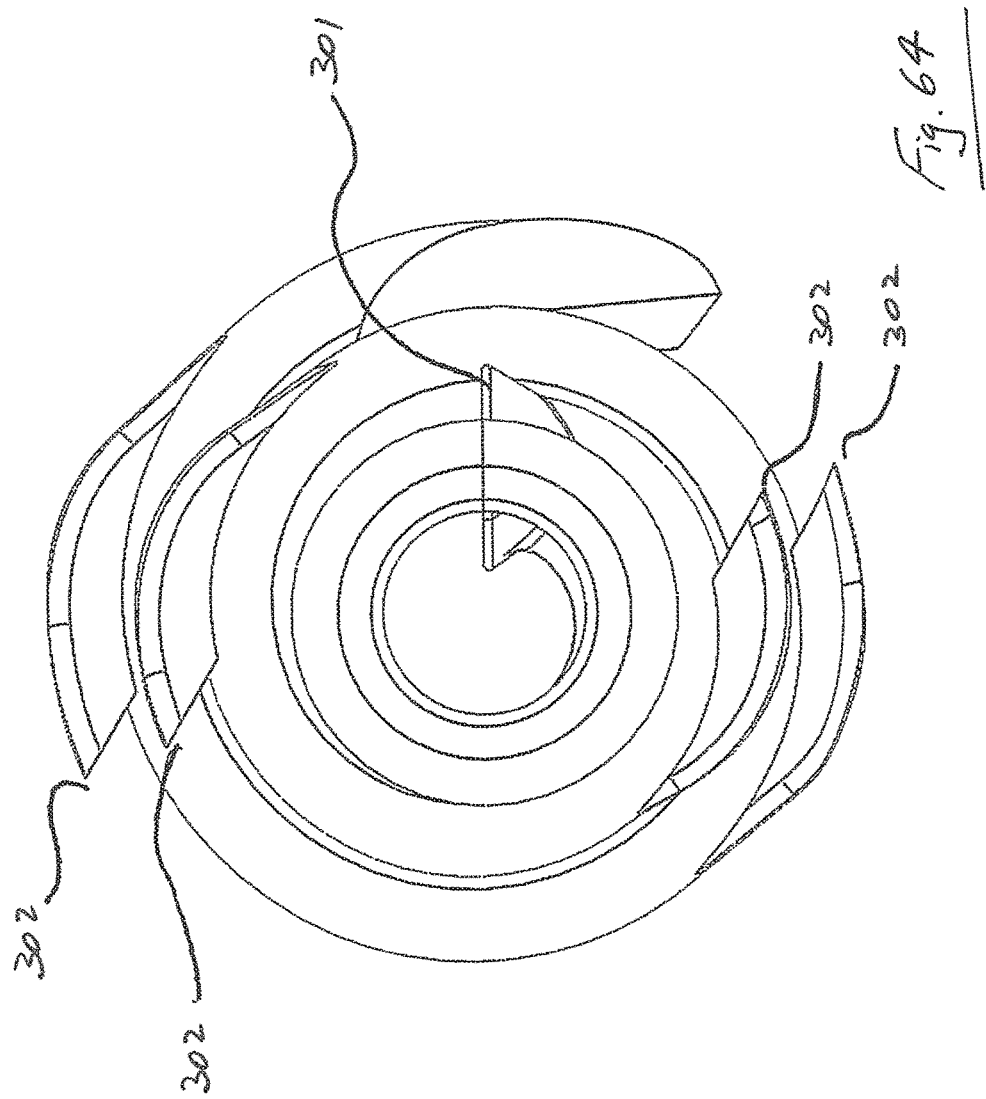
FIGS. 64 and 65 are plan views of the device of FIG. 62.
Figure 65:
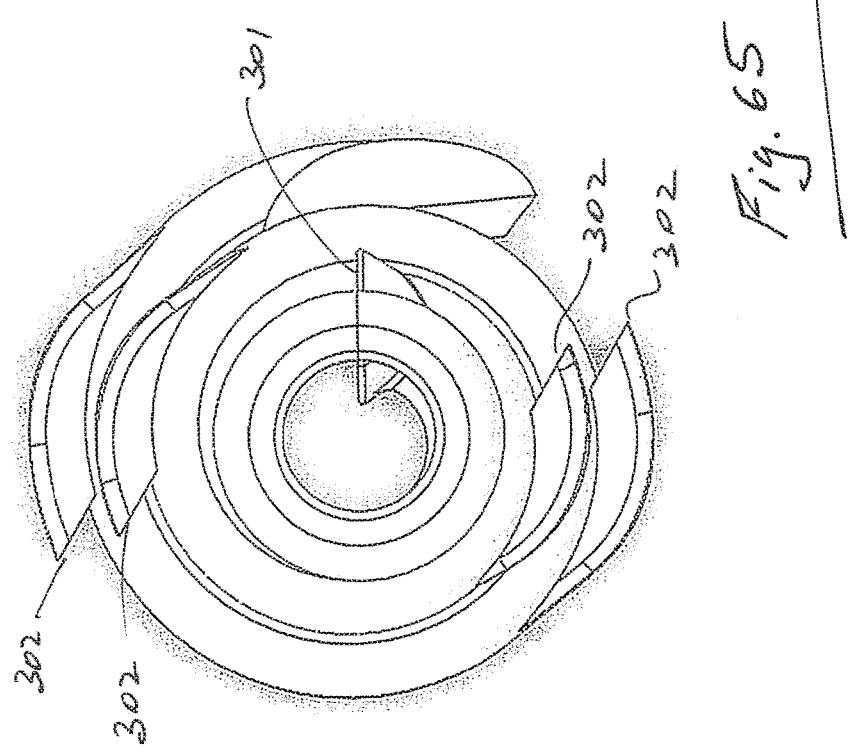

FIGS. 60 and 61 illustrate an assembly 210 in which a hollow implant coil 211 is delivered by a straight solid delivery coil 212. The coil implant 211 has a straight profile section 213 and a tapered section 214. The straight solid delivery coil 212 fits within the internal channel of the hollow coil implant 211 up to the interface 215, whereby the solid delivery coil 212 is rotated which in turn rotates the hollow coil implant 211 for delivery.

The straight sections of the coil in all cases may comprise a single turn, multiple turns or part thereof.

The hollow sections of the implant coil in all cases may comprise a single turn, multiple turns or part thereof or the entire construct.

The delivery system has the following advantages:
- Ability to follow the tract of the implant coil allowing deep delivery to the sphincter muscle complex allowing for greater anchoring and sphincter muscle apposition at the muscle defect
- Ability to disengage and retract in a spiral nature, reversing through the same tract as delivery preventing further damage to the tissue
- Prevents the mucuosa of the rectum being pulled down towards the sphincter muscle complex
- Enables the implant to be delivered through and past the anoderm resulting in lower pain due to interference with the nerve endings of the anoderm
- Prevention of bacterial tracking by delivering deep sub mucosally These delivery mechanisms may be coupled to a manually operated, trigger operated user interface or similar.

In current techniques for treating a fistula a surgeon identifies the external opening of the fistula tract and carefully inserts a probe through the external opening, through the fistula tract and through the internal opening of the fistula. The probe is then extended back through the rectum and a localisation seton or suture is attached to the end of the probe which is then drawn back through the rectum and the fistula tract until it exits through the external opening of the fistula tract. The localisation seton loop is then tied off.

The implant and delivery system of the invention is compatible with this known current technique. In the invention the probe or the localisation seton may be used to guide the leading end of the implant coil and/or the drainage seton.

The implant body in some cases is in the form of an "open" tapered coil body in which the distal edge (leading edge, into the muscle) is of a larger diameter than the proximal edge (trailing edge, rectum surface), the proximal portion is of smaller diameter than the distal portion. The coil is of open form, therefore there is no inward protrusion at either the proximal nor distal end of the body. The open form factor enables the implant to be driven into the tissue body to a pre-determined depth (depending on the taper which results in progressive tissue compression).

The open coil design allows for the mucosal layer to heal over the top of the implant, and the implant supports the healing of the mucosal layer, by preventing the pressure from opening the tract, and compromise freshly healed mucosa layer. With the implant below the mucosa it does not interfere with external rectal surface and interact with faeces that may drag the implant out of its purchase or lend to tract infection along its body. Thus, the implant is suitable for submucosal delivery which facilitates the formation of a continuous mucosal surface over the site of implantation.

The implant in some cases has anti-movement (anti-rewind) features to prevent the rotational movement of the implant in the counter-clockwise motion. Typically, the implant is driven into the tissue body in a clockwise motion consistent with the usual direction of driving fixation medical devices. However, it will be appreciated that the implant may also be driven into the tissue in the counter clock-wise direction. The anti-rewind features facilitate the forward driving motion into the tissue body in a clock-wise motion to be effortless during delivery but provide resistance to prevent the implant from working itself out or unwinding during the course of natural wound healing and normal physiological forces experienced day to day of the patient's life.

The anti-rewind features may include one or more of:

Positive feature such as a barb, fishhook, arrowhead or the like (such as features 302 of the implant illustrated in FIGS. 62 to 65). Such positive barb type features may be added in the X, Y, or Z plane to enhance the fixation of the implant;

Negative features such as trough features along the body of the implant, such trough features may be one or more of a square trough, a lead in trough, and/or a square back trough;

V-Lock type, quills may be incorporated along the body of the implant. The quills may be shaped to facilitate ease of entry into tissue but does not allow the implant to move in the opposite direction. The quill may lay fat upon insertion and then become exposed if moved in the opposite direction. A multiple of such quills increases the surface area (friction) of the implant body and prevents the implant from re-winding;

Surface modification/surface area enhancing. The surface of the implant body may be modified to increase the surface area to increase the friction interaction between the implant and the tissue it is implanted in.

Surface roughening mechanical:
    May include sandblasting, micro stamping (impression on material)

Figure 66:
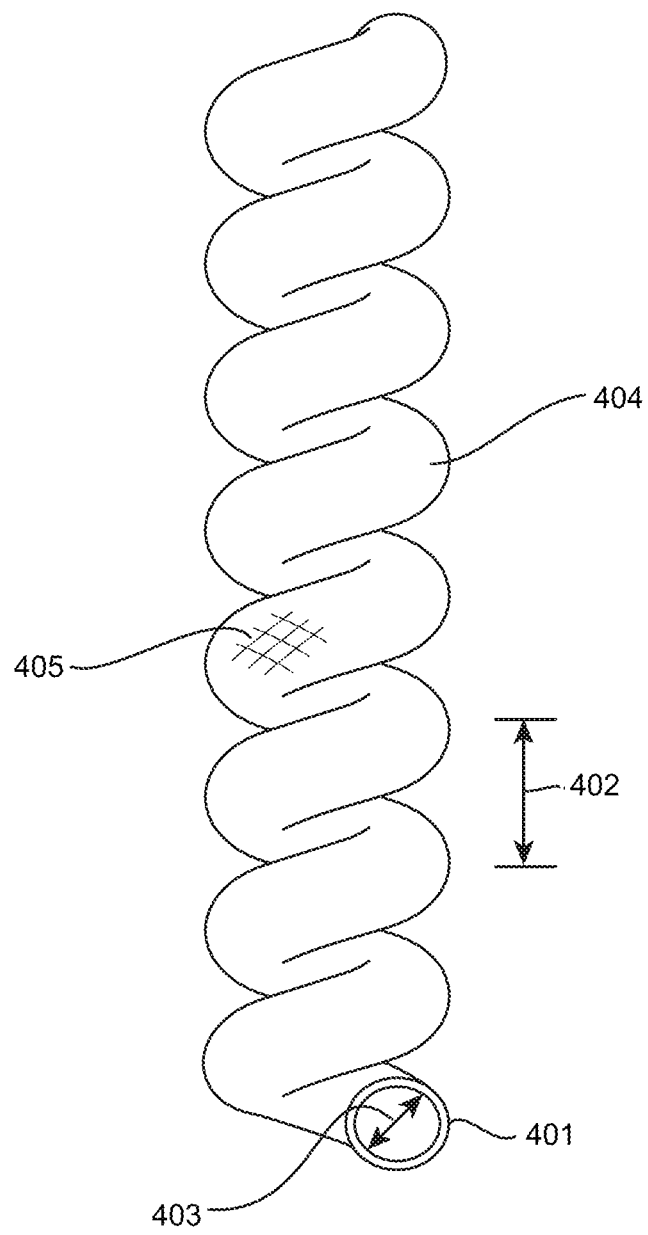
FIG. 66 is an isometric view of a delivery coil for use with the fistula treatment device.
Figure 67:
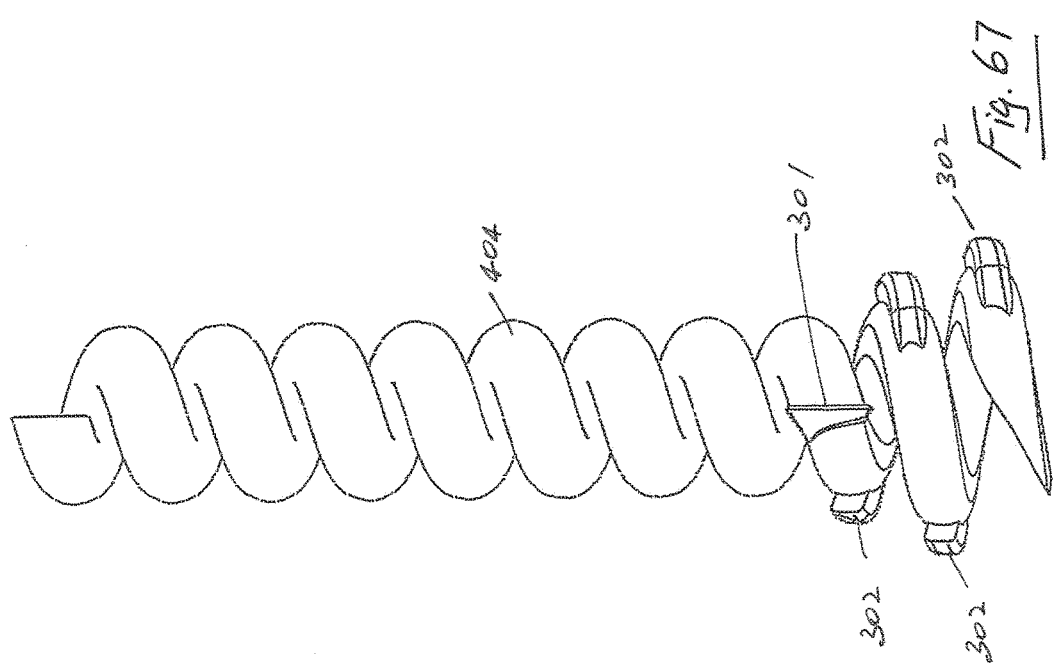
FIG. 67 is an isometric view of the delivery coil engaged with a fistula treatment device.

Surface treatment chemical:
    May include soaking (being exposed to) in a chemical agent that roughens the implant body surface
    May include chemical photo etching Surface treatment in manufacturing process:
    The tooling of a moulded implant design may have positive features that when the implant is removed from the mould, rough features are left on the body of the implant Surface "pillar" like gecko feet (Setae) Biomimicry:

As described above, a driver coil may be used to insert the implant. The driver coil (such as the coil 404 illustrated in FIG. 66) may have advantageous pitch 402 and diameter 403 dimensions to minimise tissue binding during the delivery of the implant coil.

In addition, the driver coil surface 405 may be constructed so as to have a lubricious nature (e.g. by means of a coating or surface treatment or other) in order to minimise the torque requirement associated with the tissue friction during delivery of the implant coil and during retraction of the delivery coil.

The coiled section of the delivery coil may include features to temporarily lock or fasten to the implant prior to and during implant delivery. This provides a positive interface between the implant and the delivery mechanism, to prevent premature implant detachment and related delivery issues.

When the implant has been delivered to the correct location and depth the delivery mechanism detaches/disengages from the implant and is removed from the anatomy.

The driver coil may have an interface to the implant which allows positive (interlocking) when the driver coil is turned in a clockwise direction and negative (i.e. disengagement) interaction when the driver coil is turned in an anti-clockwise direction (or vice versa). Thus when the implant has been delivered to the tissue by means of a clockwise driver coil motion, the driver coil may then turn in an anti-clockwise direction, disengage from the implant, and exit (or 'back out') from the tissue.

The implant may be attached to the delivery coil by a mechanism that prevents the implant becoming dislodged from the delivery coil prior to complete delivery. Thus, the implant coil is prevented from prematurely detaching from delivery coil.

The internal support structure of the implant coil may have a positive feature (peak) that locks into a negative (valley) feature on the implant. There maybe be several features of this type to enhance the locking grip.

The inverse of this arrangement may also be implemented in which a positive feature is provided on the implant and a negative feature is a part of the driving mechanism.

Alternatively or additionally, the implant may be attached to the internal opening of the implant driver by friction/interference fit/surface roughness. The driver col may be hollow and accept a solid implant or the driver may be solid and inserted into the hollow portion of the implant.

The cross section of the driver coil may be a channel or slot rather than closed circular. A coil with such a cross section may be more easily manufacturable. It may also allow the incorporation of internal (to the driver coil) locking features to interface with the implant.

The implant is interfaced to the driving mechanism such as a driver coil. In one case the interface comprises a flare or step that abuts against the driving mechanism. One such flare or step 301 is illustrated in FIGS. 62 to 65. Such a flare provides the push point of the implant and transfer of force to drive the implant into the tissue body.

The flare may also act as a barb or anti-rewind feature allowing only one way (e.g. clockwise) motion which in one case is forward motion (clockwise motion driven into the tissue body) and prevents the implant from moving in a backwards motion (unwinding/counter clockwise).

Such a barb feature may be achieved by having the flare surface area greater than the driving coil interface surface area.

The flare may be positioned anywhere along the implant body that is optimal for the implant driving force, driver attachment coupling, and/or anti motion control (anti-rewind can be clockwise or anti clockwise).

It will be appreciated that as an alternative to such locking features on the implant coil similar features may be provided on the engagement surfaces of the delivery coil.

The implant is in some cases in the form of a coiled body structure. The distal end of the implant is the largest coil, and the distal end initially surrounds the tissue defect with appropriate margin. As the implant is advanced the distal portion provides a large surface area to effectively anchor the implant (each subsequent coil provides (adds to) the anchoring and compression function). The smallest proximal coil provides the highest amount of tissue compression. As the implant is turned into the tissue each coil further compresses the captured tissue toward the centre of the tissue defect, thus effectively completely compressing the surrounding tissue inwardly. The close approximation of tissue allows for the tissue to heal together. This compression provides an effective seal against the pressures generated in the rectum and prevents entering of passing faeces into the fistula tract thus preventing re-infection. The smaller diameters of the implant coils retain the captured tissue from separating and prevents the breakdown of the healing process or foreign material from entering the tissue defect. This is the advantage over sutures and suture based surgical techniques such as the advancement flap (dermal flap) and the LIFT procedures.

The compression ensures close approximation of tissue throughout the centre of the implant. At the most proximal surface the close approximation of tissue provides support to the healing mucosal lining of the rectum over the implant and tissue defect. Thus the healing tissue is fully supported by the implant during the healing process and is capable of surviving pressures of 150 mmHg and upwards of 200 mmHg which are generated in the rectum.

Preferably, the coil is delivered submucosal (at a predetermined depth) below the surface of the mucosa. This ensures there is a full mucosal seal at the rectal mucosa surface to provide for a bacterial seal barrier. With the implant just below the surface the tissue is draw inwards for complete compression and supports the mucosa healing process.

As the implant is turned into the tissue the compression becomes greater along the depth of the coil (progressive compression) and the length of the tract captured internal of the implant is compressed completely, the close approximation of tissue aids in the healing process.

The implant and delivery system is compatible with current surgical technique.

Upon completion of the surgeon preparing the tissue tract, the device drain is attached to the rectal end of the fistula probe or seton/suture that was used to localize the tract.

The probe/seton is pulled toward the surgeon through the fistula tract out of the external opening until the large distal portion of the implant is abutted against the rectal wall. The Implant coil is aligned to be concentric to the internal tract opening.

The device drain is tied to the fistula probe or localization seton.

In one embodiment the drain seton runs distal of the implant and through the length of the handle and may be anchored in the proximal portion of the drive shaft or handle.

At the interface of the implant and driver a cutting mechanism (such as a snip, guillotine or the like) may be provided to automatically cut the drainage seton once the implant is delivered. The handle/delivery system may then be readily removed from the surgical field.

In another embodiment the drain seton is locked to the handle/driver mechanism during implantation (delivery of implant) to maintain traction. Once the implant is fully implanted the handle is decoupled (automatically or manually) from the drain seton. The excess drain seton material may be trimmed at the external surface of the closed tissue tract site at the surface of the rectum.

Figure 72:
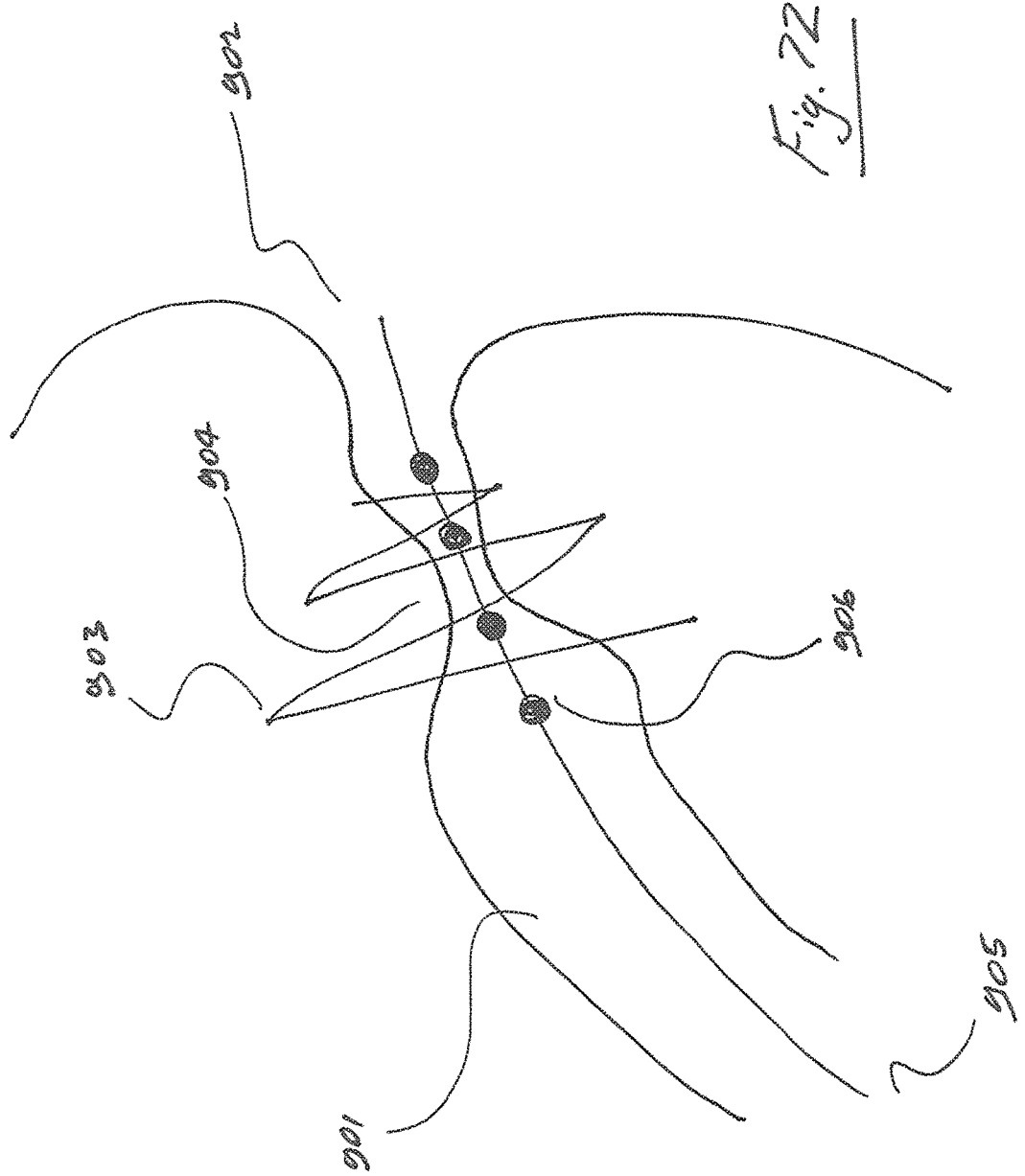
FIGS. 72 and 73 illustrate the fixing of a drainage seton into position in a tissue tract.
Figure 73:
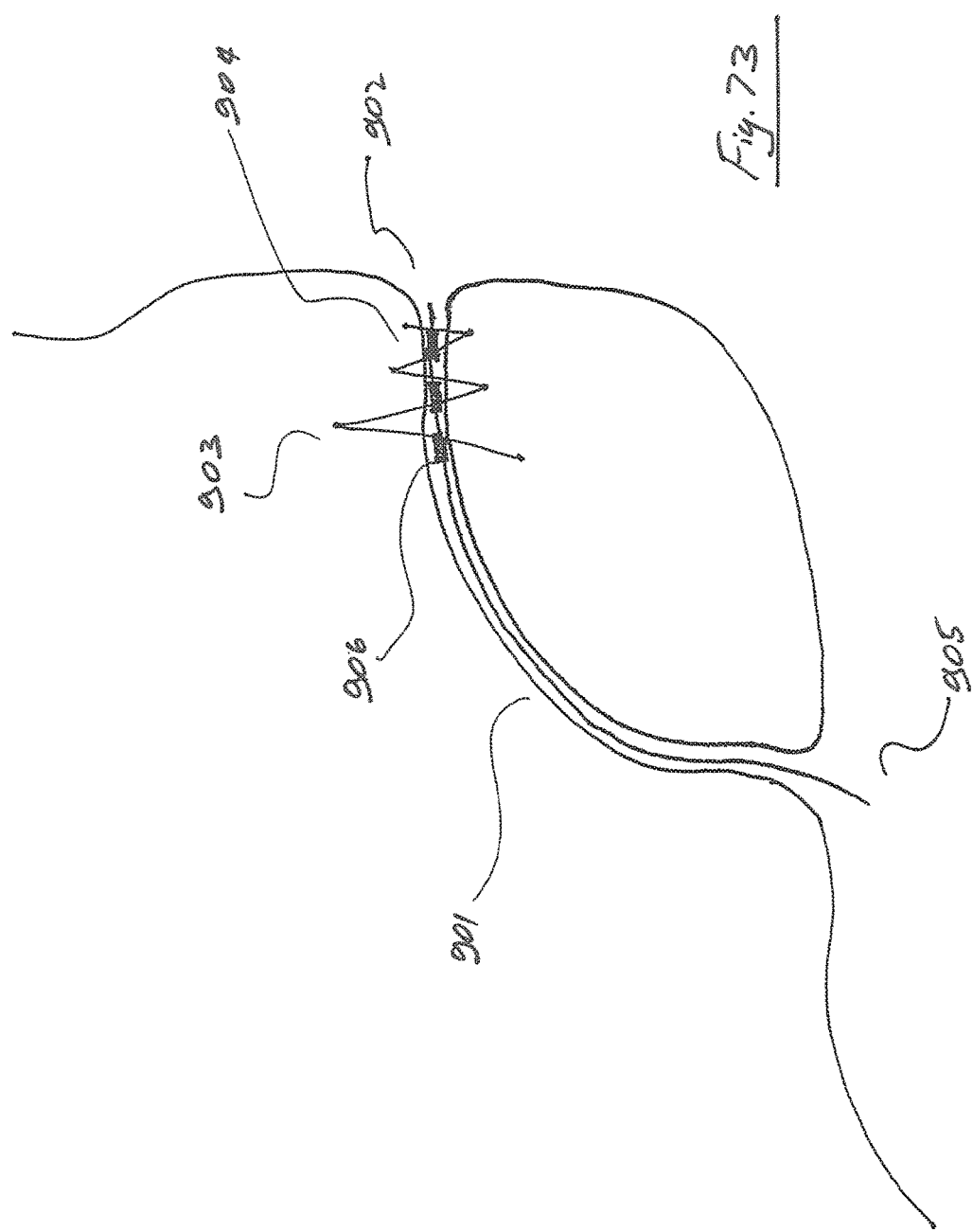

Referring to FIGS. 72 and 73, a seton 905 is held in a fixed position along the length of the tissue tract 901 due to the compression at the internal opening 902. The implant opening 903 compresses the tissue opening 904 around (onto) the drain seton 905, locking it into place. The drain seton may have a specialty designed/located compression zone and may have corresponding features to facilitate the anchoring of the seton in this zone 906.

The drain is fixed in place due to the compression forces of the internal tissue tract being compressed inwardly by the radial forces applied by the implant.

To further enhance fixation of the drain seton and prevent the drain seton from moving out of the tract distally or proximally the drain seton may be constructed with locking features 906 along the entire length, partial length, and defined/predetermined compression zone at the site of the implant tissue compression, or any combination of these.

Figure 68:
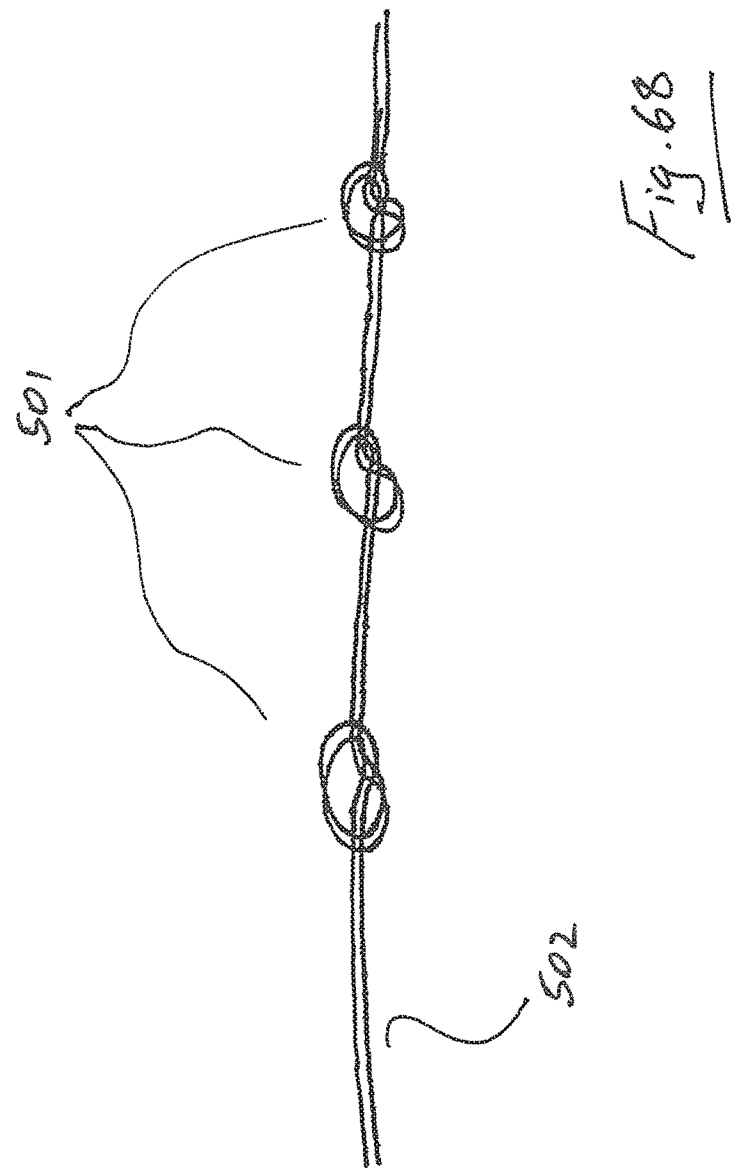
FIG. 68 is a view of a drainage seton according to the invention.

Referring to FIG. 68, knots 501 may be implemented along the length of the drain seton 502 or at a specific location such as that of the implant compression zone.

Figure 69:
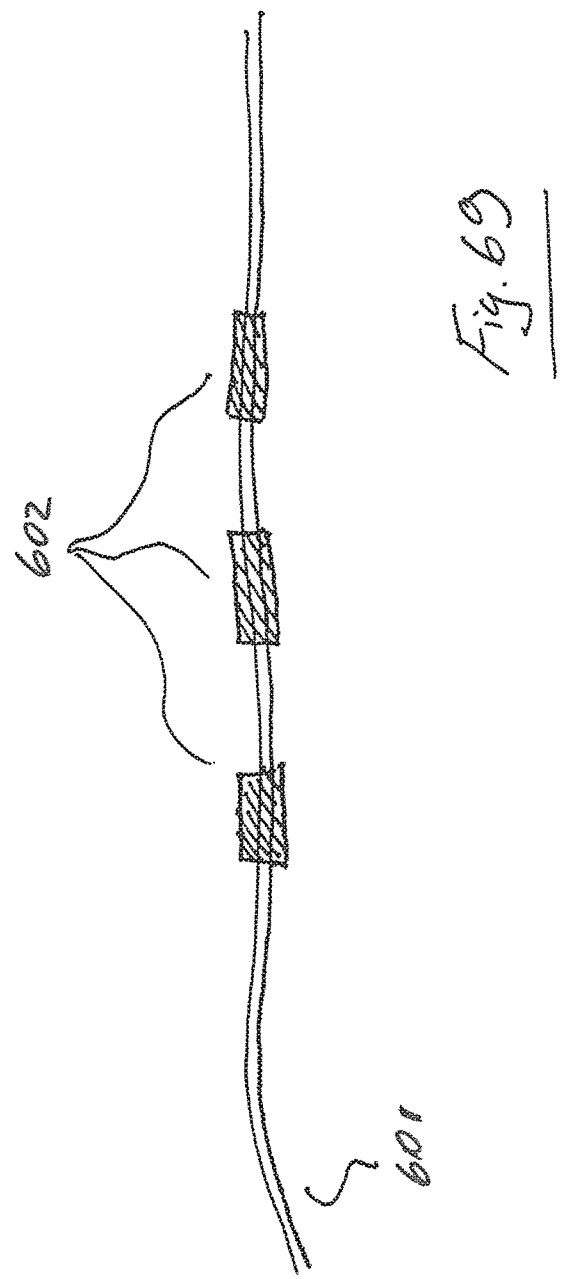
FIG. 69 is a view of another drainage seton of the invention.

Referring to FIG. 69, spheres, cylinders, triangles and other multifaceted shapes 602 may be provided such as by moulded over along the length of the drain seton 601 or at a specific location such as that of the implant compression zone.

Figure 70:
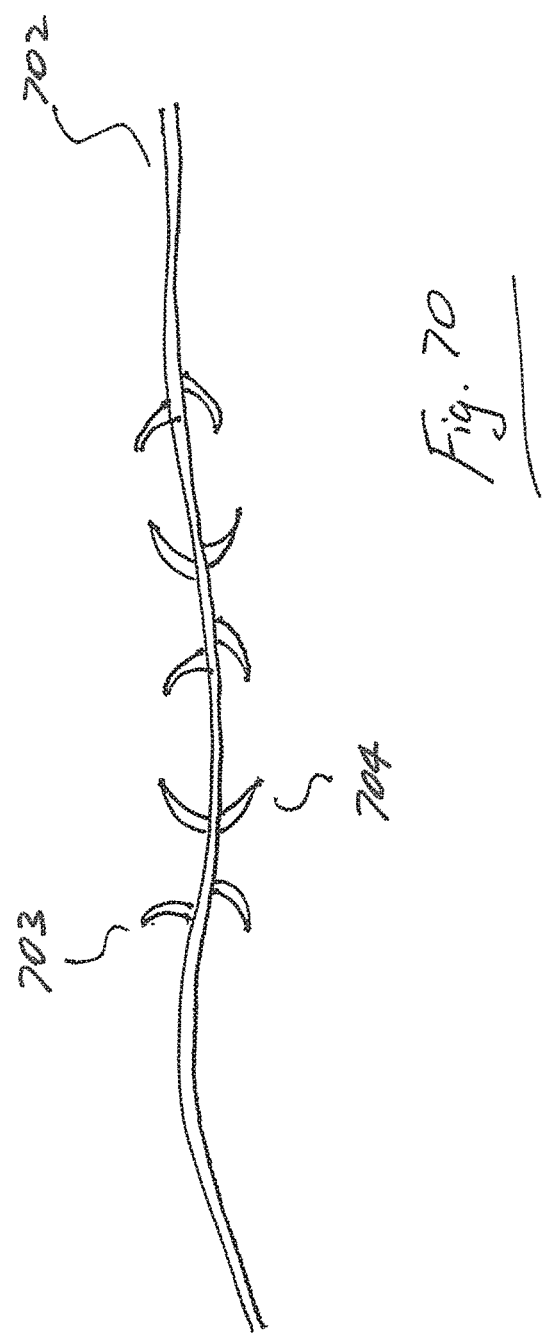
FIG. 70 is a view of a further drainage seton of the invention.

Referring to FIG. 70, enhance the anchoring of the drain seton barbs 703, 704 may be incorporated along the length of a drain seton 702 or at a specific location such as that of the implant compression zone. The barbs may face in both the external 703 and internal opening directions 704 to prevent motion in either direction.

Figure 71:
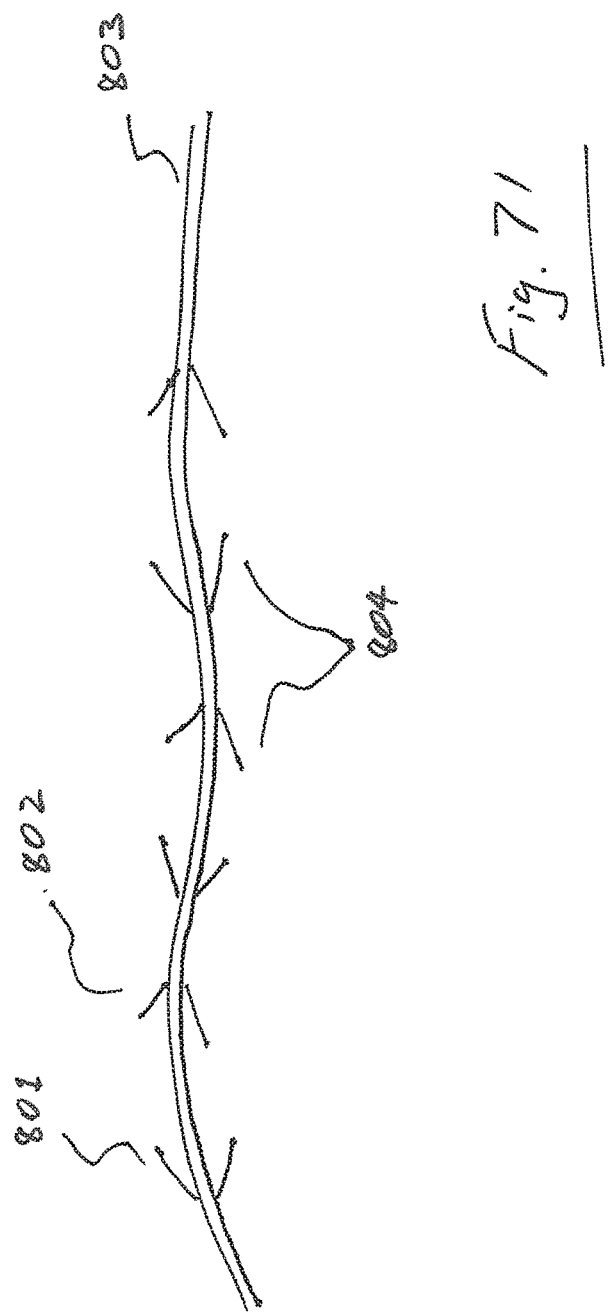
FIG. 71 is a view of another drainage seton.

To enhance the anchoring of the drain seton quills such as 801, 802, 804 (FIG. 71) may be incorporated along the length of the drain seton 803 or at a specific location such as that of the implant compression zone. The quills may face in both the external 802 and internal opening direction 801 to prevent motion in either direction.

The drain seton maybe be constructed to act purely as a drain and/or as a scaffold to enhance tissue healing.

To provide enhanced drainage, the seton may have a plurality of peripheral holes and may include (pores). The shape of the seton in cross section may be selected from one or more of round, oval, star and cross. The drain/seton is constructed to be bioabsorbable.

An example of potential materials include: PLA and PLGA (poly(lactic-co-glycolic acid)) (PLGA, PCL, Polyorthoesters, Poly(dioxanone), Poly(anhydrides), Poly(trimethylene carbonate), Polyphosphazenes), and or natural bioabsorbable materials may include fibrin, collagen, chitosan, gelatin, Hyaluronan are bioabsorbable polymers and would be a material of choice as they are commonly used bioabsorbable materials.

The shape is designed to enhance the drainage of the residual tract. The shape may also act as a scaffold to improve/enhance the healing of the tract.

The plurality of peripheral holes/pores enhance drainage of the tract to prevent the drain/seton from blockage.

To enhance scaffolding, the plurality of peripheral holes/pores may serve as a structure of a scaffold that enhances tissue integration and improves wound healing of the tract.

A variety of materials may be used as a tissue scaffold that enhance and improve tissue wound healing. Many of these materials are bioabsorbable polymers or natural tissue materials. An example of potential materials include: PLA and PLGA (poly(lactic-co-glycolic acid)) (PLGA, PCL, Polyorthoesters, Poly(dioxanone), Poly(anhydrides), Poly(trimethylene carbonate), Polyphosphazenes), and or natural bioabsorbable materials may include fibrin, collagen, chitosan, gelatin, Hyaluronan are bioabsorbable polymers and would be a material of choice as they are commonly used bioabsorbable materials.

The invention also provides a mechanism to stabilise the tissue during the delivery of the implant to prevent bunching and twisting of the mucosal layer during delivery of the implant. By preventing such tissue interaction, the delivery forces may be reduced and a more reliable and repeatable depth of delivery may be achieved.

Figure 74:
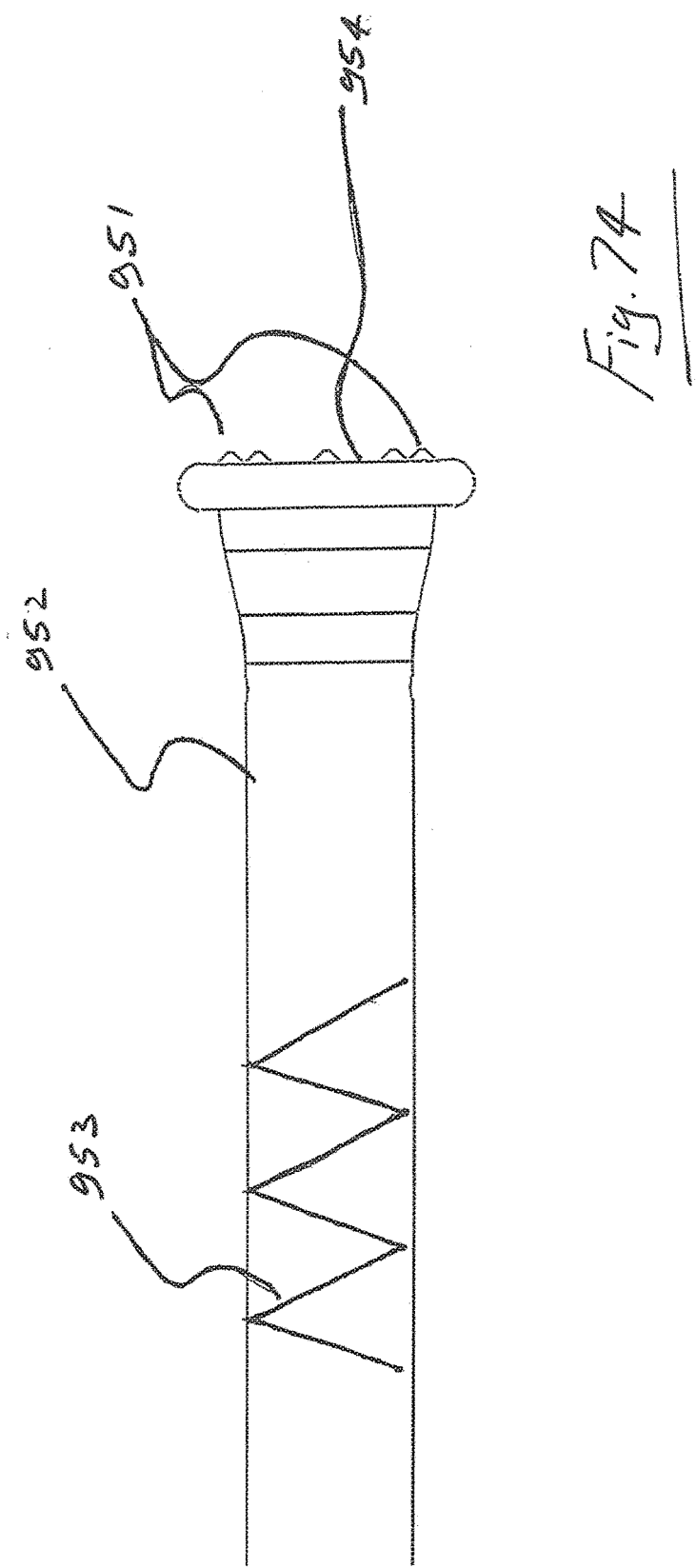
FIGS. 74 and 75 are views of a stabilising device according to the invention.
Figure 75:
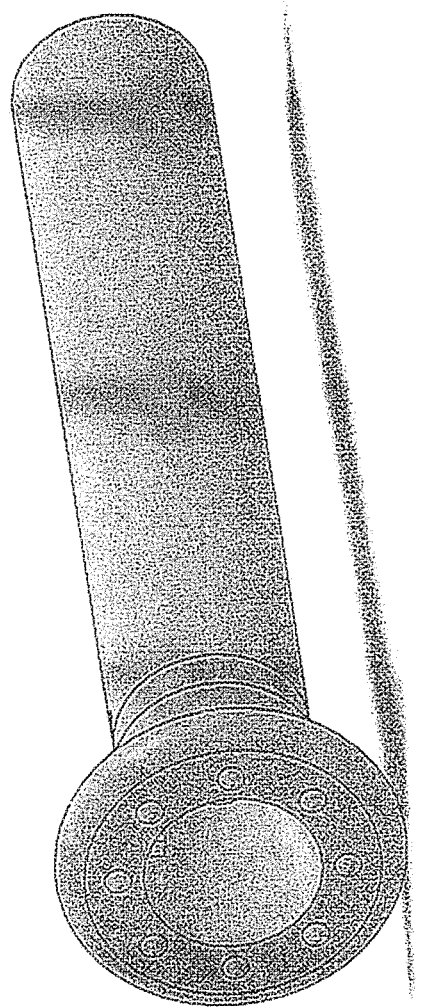

One mechanism of stabilising the mucosal tissue is achieved by utilising a hollow 'trumpet, cone, shield or pyramid' type element that is attached to the delivery mechanism and surrounds the undelivered implant. One such stabiliser 952 is illustrated in FIGS. 74 and 75.

The 'trumpet' interfaces onto the surface of the mucosal lining and may stabilise the tissue prior to and during the delivery of the implant using one or more of the following mechanisms:

Pressure—the trumpet may be spring loaded (953) or otherwise to apply pressure to the mucosal surface. The pressure may be manual force from the user's application of the delivery mechanism while abutting to the mucosal surface Spike type features. The surface of the trumpet that interfaces to the mucosal surface (954) may contain features that penetrate into the mucosal surface and hence prevent rotation or twisting of the mucosal lining. These features may be in the form of:
Needles
Microneedles
Micro-spikes (951)
Castellated features (similar to the features of a rook in a chess set)

The features may be incorporated into the trumpet by means of:
Overmoulding
Injection moulding
Press fit
Surface treatment
Rubberized surface
Surface modification
Surface roughening (sand blasting etc.).

Referring to FIGS. 76 to 79 there is illustrated a system comprising a guide or driver 1101 which in this case is in the form of a coil, and an implant element 1102. In this case the guide coil 1101 is hollow and is made of a rigid material and contains the implantable element 1102. The implantable element 1102 may be made of a malleable material and may also be bioabsorbable. The guide coil 1101 has a sharp tip 1103 to facilitate penetration into tissue. The sharp tip 1103 may be solely part of the guide 1101, or a part of the guide 1101 and implantable element 1102 or solely the implantable element 1102.

Figure 78:
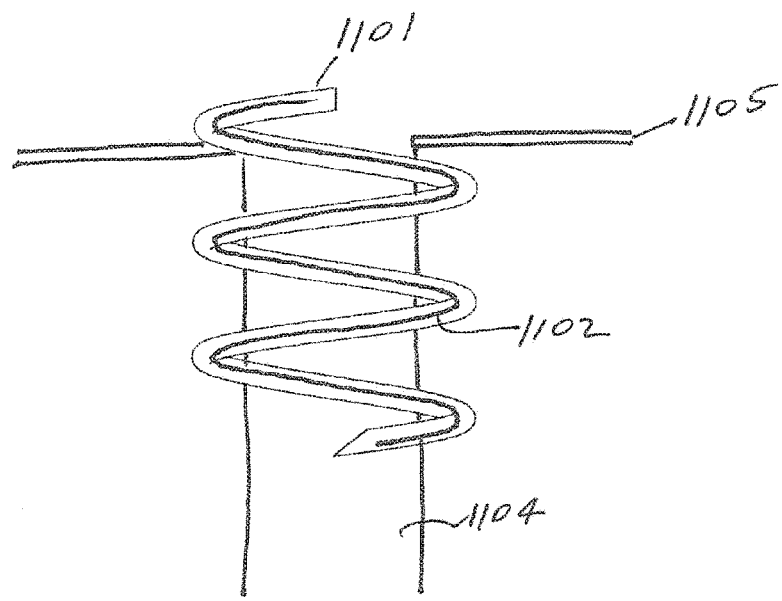
FIG. 78 shows the system in a delivery configuration.
Figure 79:
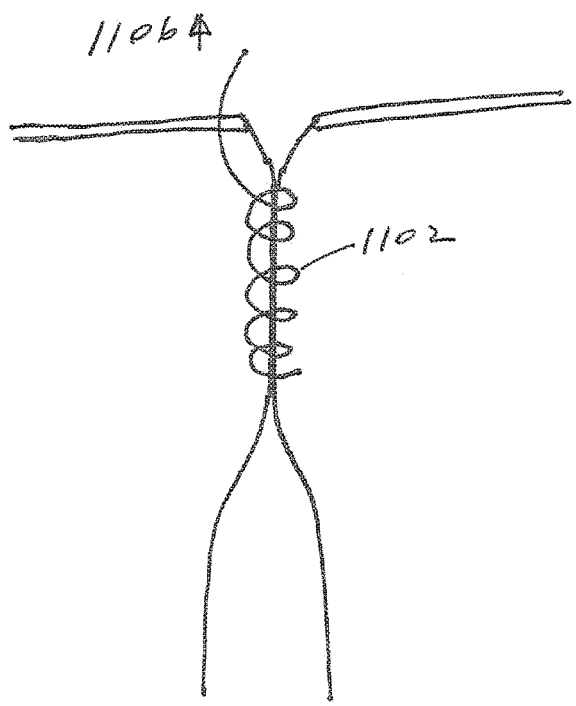
FIG. 79 illustrates an implant element in an activated configuration.

The guide coil 1101 has a distal diameter that is larger than the tissue defect such that, in use, the guide 1101 surrounds the internal opening of the fistula track FIG. 78. The guide coil 1101 is driven into the tissue, surrounding the internal opening of the fistula tract 1104 to a depth to below the tissue mucosa 1105 to capture the appropriate amount of sphincter muscle tissue. Once at depth, the guide 1101 is unwound from the tissue leaving the implantable element 1102 anchored in the tissue and surrounding the fistula tract (FIG. 79).

With the guide 1101 removed from the tissue and the implantable element 1102 anchored in the tissue, the implantable element 1102 is activated in this case by pulling in the direction of the arrow 1106. The implant 1102 is anchored distally in the tissue and collapses and compresses the tissue tract closed (like a purse string or boa constrictor snake) FIG. 79.

The guide coil 1101 may be a straight or tapered coil. The coil may be hollow or a rail type support or an internal support (such as a removable wire internal to a hollow implant element).

Figure 80:
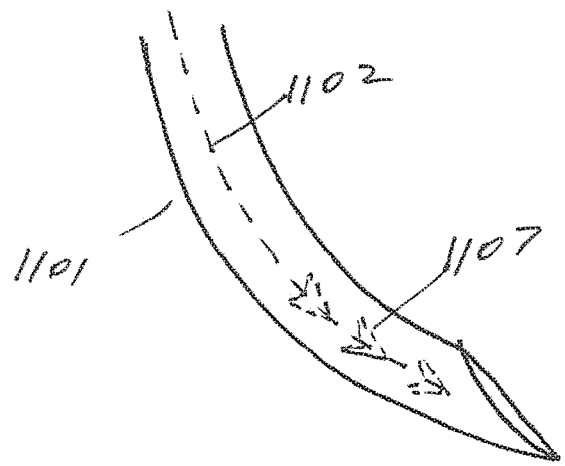
FIG. 80 is a diagram of a distal end of a delivery coil and an implant element having an anchor.
Figure 81:
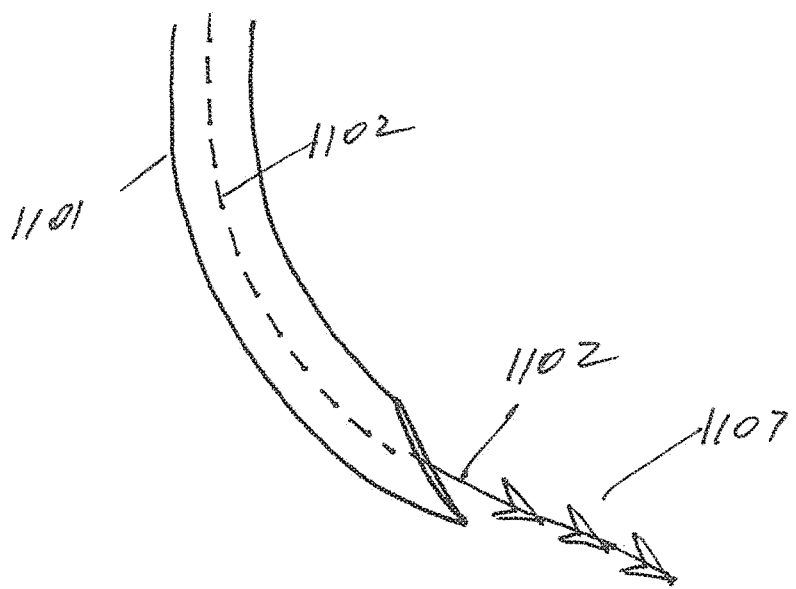
FIG. 81 shows the delivery coil in another configuration in which the anchor is exposed.

The implant element 1102 may be anchored in various ways. A single, (or multiple), barb 1107 or locking feature may be located at the distal end of the implant element 1102. The barb(s) 1107 allow the implant element 1102 to penetrate the tissue in one direction FIG. 80, but when pulled in the opposite direction the barbs 1107 catch and lock the implant in place FIG. 81.

Figure 82:
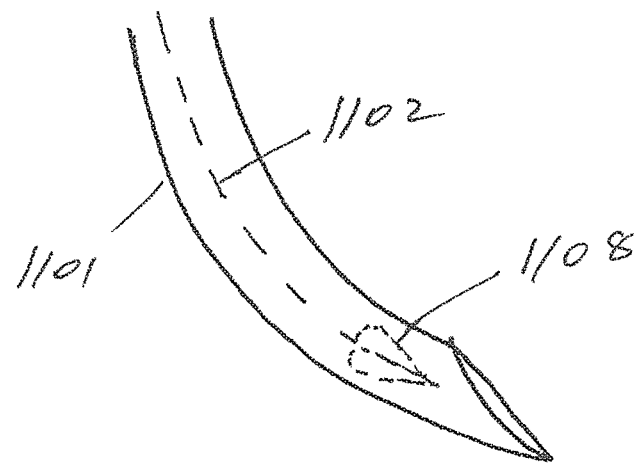
FIGS. 82 and 83 illustrate another anchor.
Figure 83:
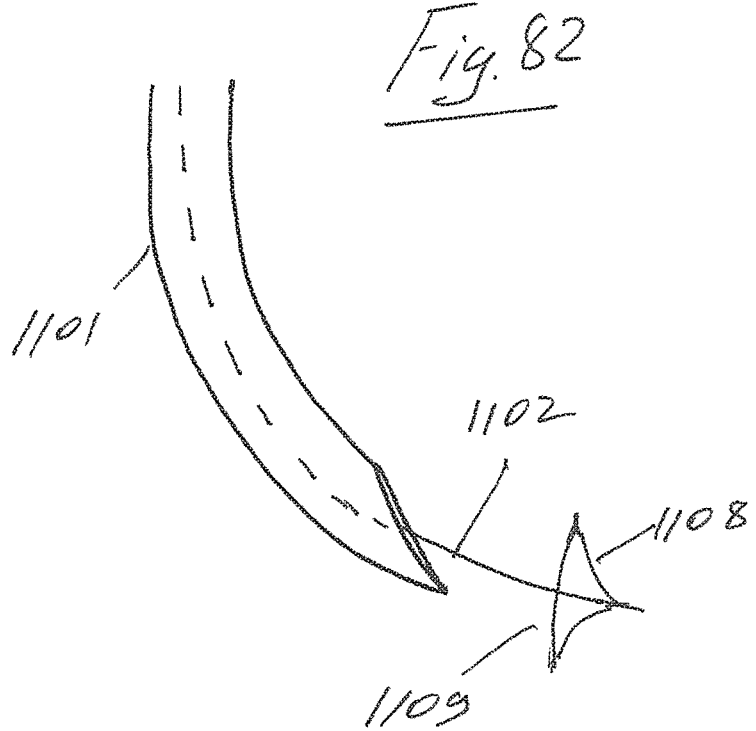

The anchor can be an "umbrella shape" or "parachute" shape element 1108 that is attached to the distal end of the implant element 1102. The "parachute" is initially stowed during delivery (FIG. 82) and is unfurled upon the driver element's extraction (FIG. 83). The large surface area of the parachute 1109 captures the tissue at the point of anchorage, locking the implant element 1102 in place.

Figure 84:
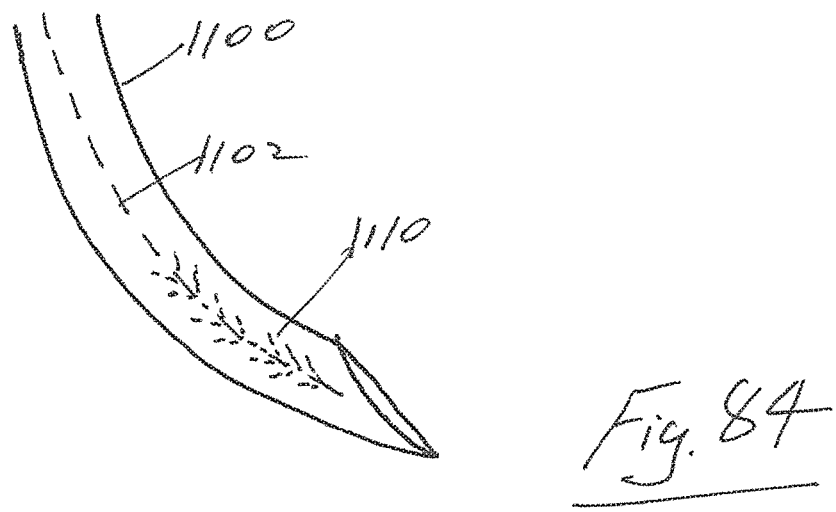
FIGS. 84 and 85 illustrate a further anchor.
Figure 85:
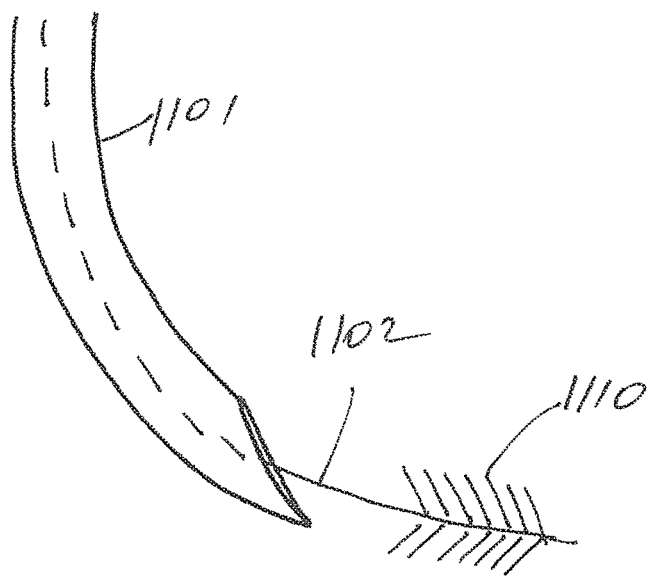
Figure 86:
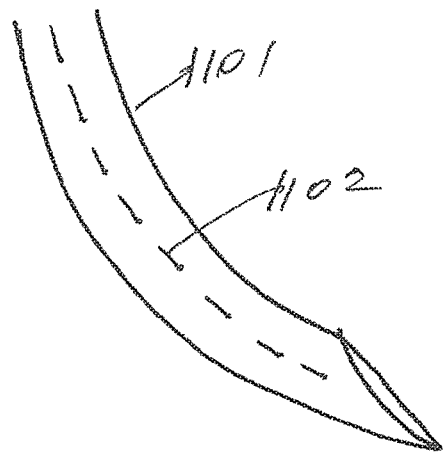
FIG. 86 illustrates another guide and an implant element.

Multiples of small "hair" like filaments 1110 may be provided along a length of the distal surface covering the full circumference, specific quadrants, and or intermittently covering the distal surface of the implant element 1102. This quill-like configuration increases the surface area of the distal end and anchors the implant element 1102 in the tissue. The bristles or quills 1110 are initially collapsed/compressed when stowed in the driver guide (FIG. 84). When the guide is removed from the tissue the bristles are exposed and lock into the surrounding tissue (FIG. 85).

Figure 87:
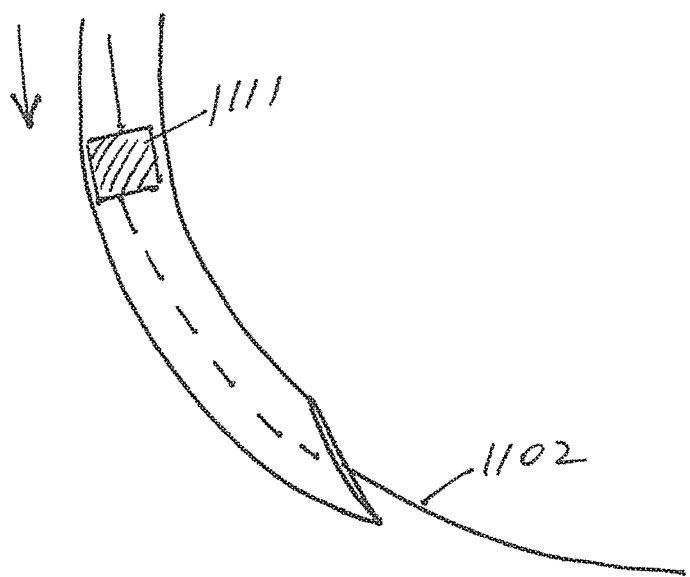
FIG. 87 illustrates deployment of the implant element of FIG. 86.

In some cases the implant element 1102 does not have an anchor. In this case the implant element 1102 may be positioned by a pusher 1111 during removal of the guide mechanism after delivery to the desired location (FIG. 87).

The implantable element 1102 may be at least partially bioabsorbable. The element may comprise a suture which is anchored distally into tissue. When the guide 1101 is removed, the suture can be pulled proximally and will then cinch the tract closed, similar to a purse string.

The implant element can be made of a shape memory material such as Nitinl or a shape memory polymer. It can be active (requires a stimulus such as electrical, mechanical, light, magnetism or the like) or passive (heat set).

The implant element 1102 may be stowed in the guide element 1101 for delivery into the tissue. Once the guide/driver element reaches the desired depth, the guide element is unwound from the tissue. As the guide is unwound from the tissue the anchored implant is no longer supported by the guide and the exposed portion(s) of the implant is free to compress the tissue tract. The passive shape set implantable element compresses the tissue tract as the guide element 1101 is unwound from the tissue. The implantable element 1102 may be preset in shape before stowage in the guide element 1101. For example, a Nitinol coil is shape set into the compressed state and is then inserted into the guide 1101.

The implantable element 1102 may be stowed in the driver/guide element 1101 for delivery into the tissue. Once the guide element reaches the appropriate depth the guide 1101 is unwound from the tissue leaving the implant element 1102 anchored in tissue. With the guide element 1101 removed from the tissue the implantable element 1102 is then activated by any suitable means such as heat, light, electrical signal, changing the state of the implantable element and activating the implantable element to be transformed to the compression state, thus compressing the tissue tract closed. The patient's body heat may passively activate the implant element to transform to the compressive state.

A sharp tip may be provided at the distal tip to penetrate into the tissue as the guide/delivery mechanism is advanced into the tissue.

Figure 76:
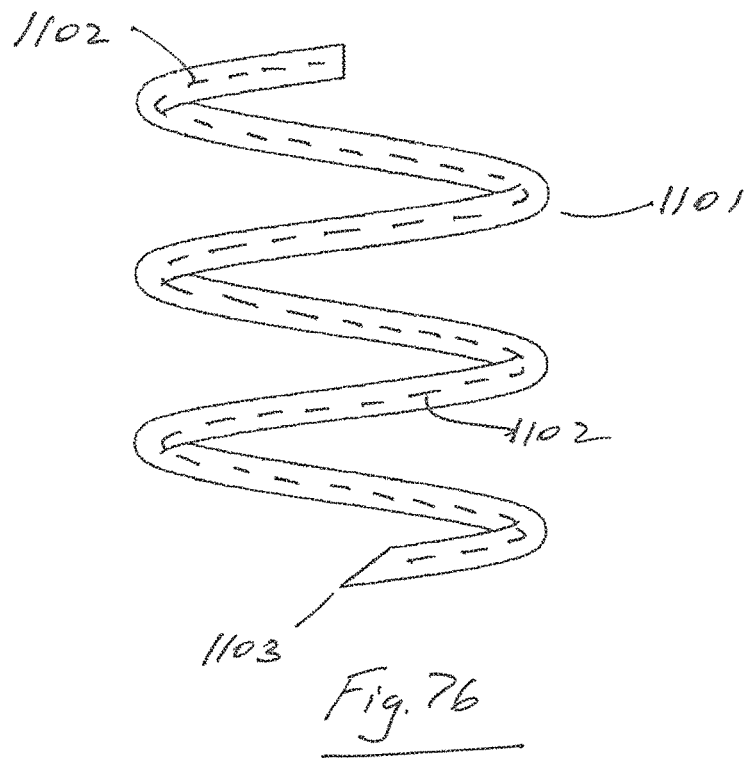
FIG. 76 is a diagram of a fistula treatment system according to the invention.
Figure 77:
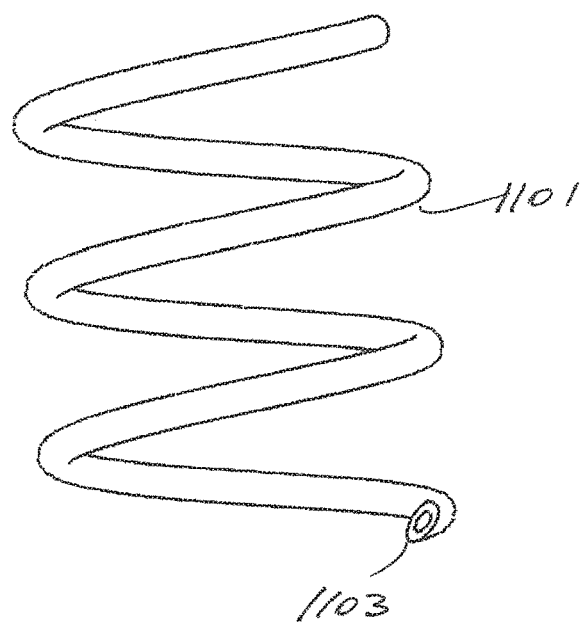
FIG. 77 is a perspective view of a guide coil of the system.

In one configuration the distal tip and leading edge of the coil guide/driver element 1101 has a sharp tip that facilitates the penetration of tissue upon insertion and during advancement throughout the tissue FIG. 76, 1103. The implant element 1102 can pass through the sharp tip when correctly located in the tissue.

Figure 88:
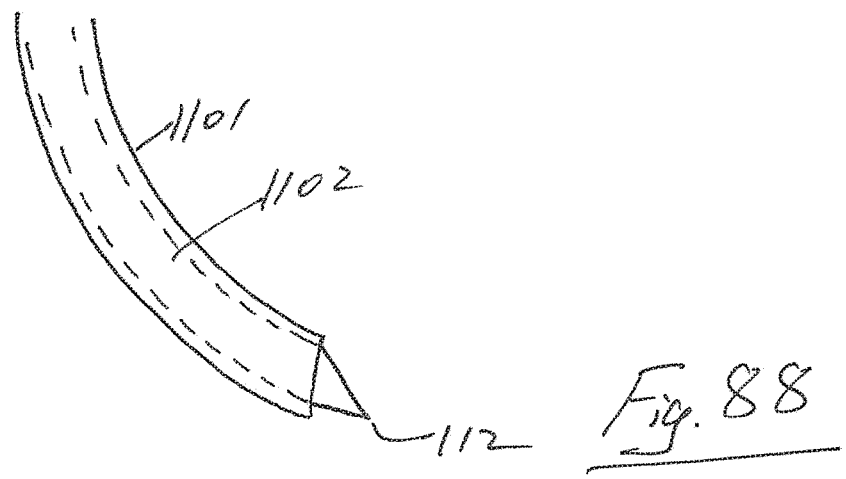
FIGS. 88 and 89 show another guide and an implant element with a sharp distal tip.
Figure 89:
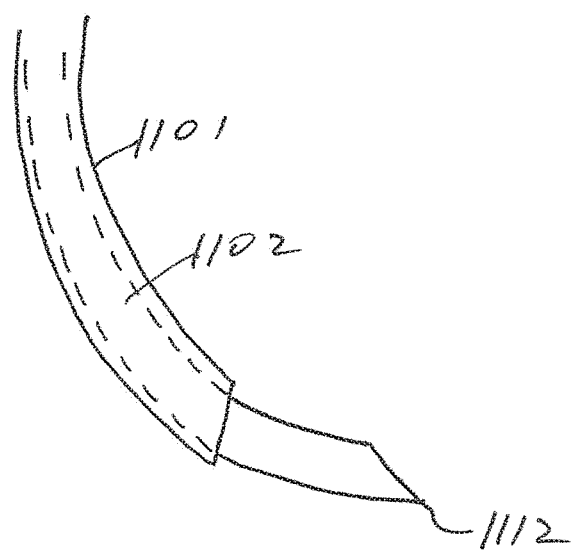

In another configuration (FIG. 88) the implant element may have a sharp tip 1112 at the distal end that facilitates the penetration of tissue upon insertion and during advancement throughout the tissue A sharp tip in some cases may be incorporated into both the driver element and the implant element.

In some cases the implant element is an activatable element which may have a collapsed delivery configuration, a deployed configuration, and an activated configuration.

The activatable implant element in some cases is an expansile element such as a balloon.

Figure 90:
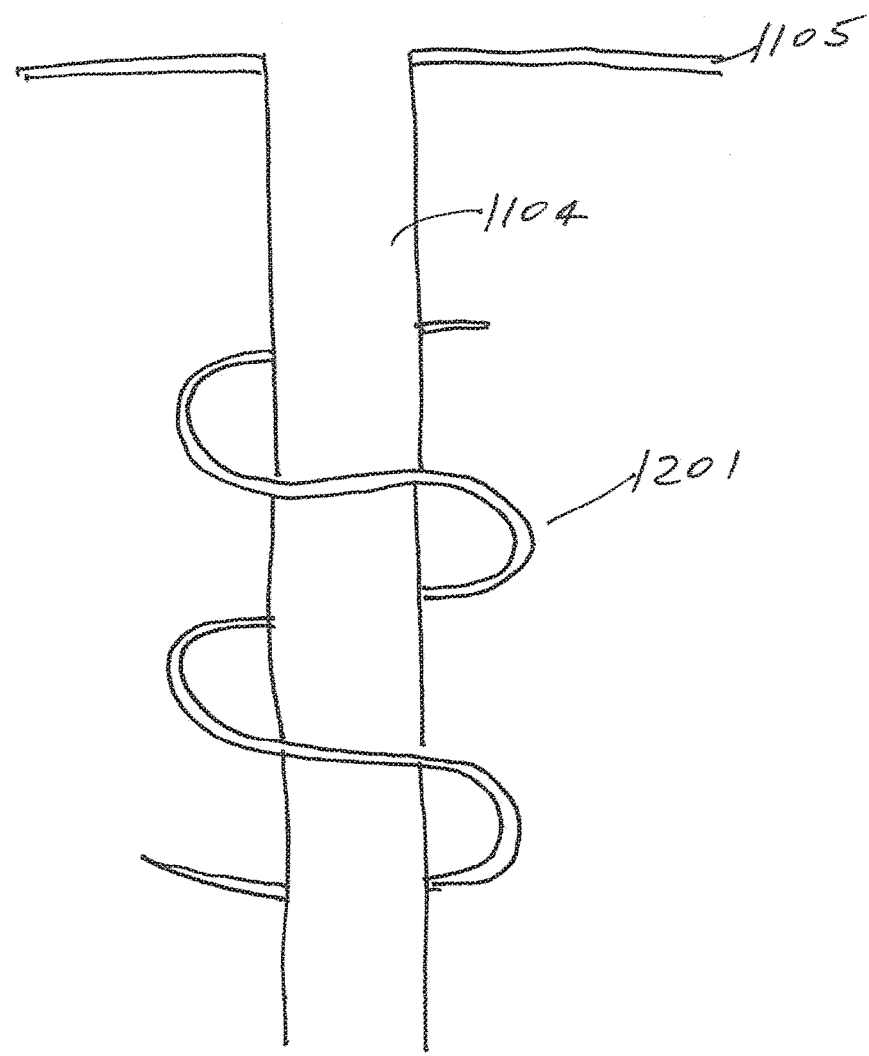
FIG. 90 is a diagram of another implant according to the invention.
Figure 91:
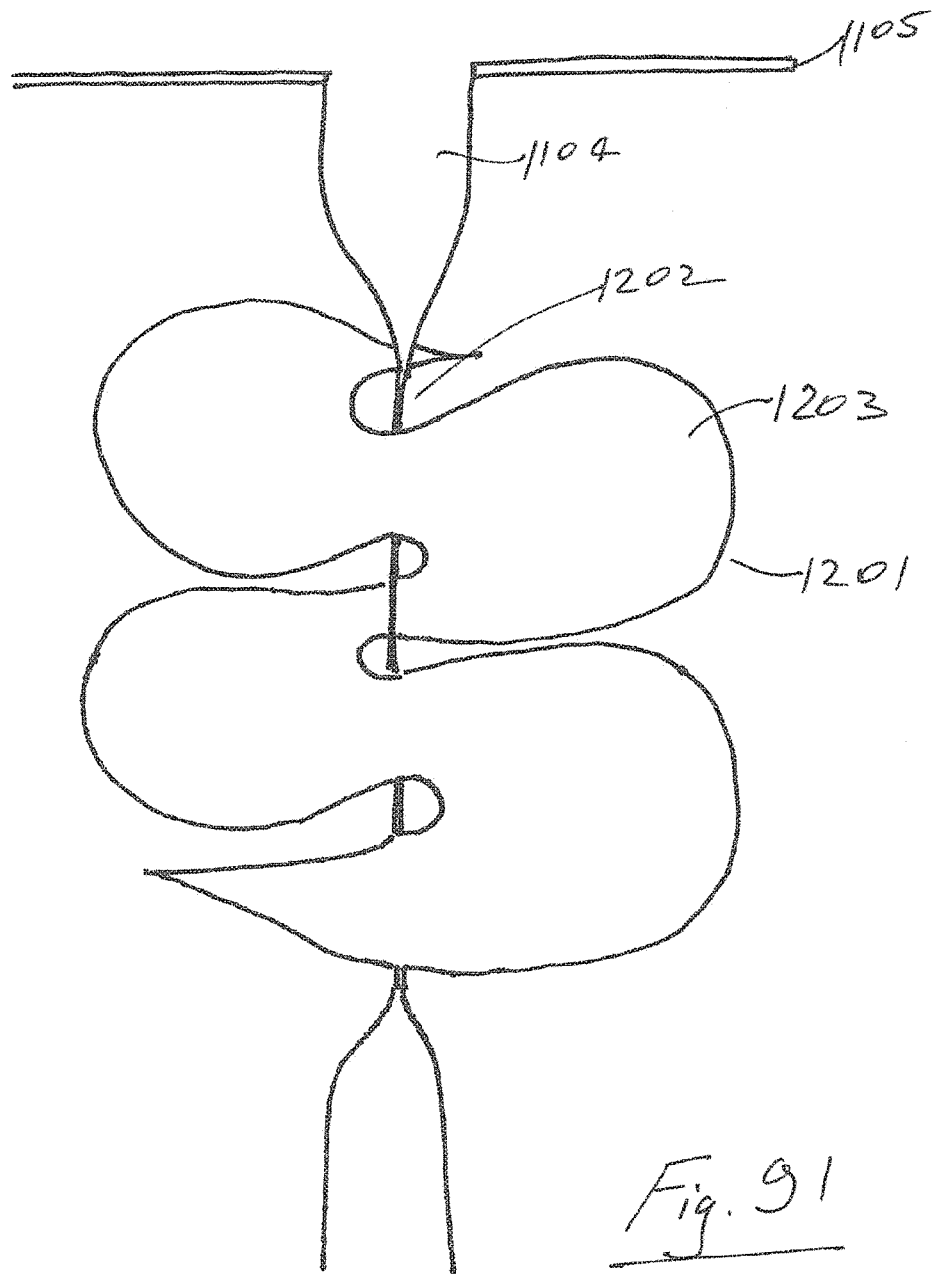
FIG. 91 shows the implant of FIG. 90 in a deployed and activated configuration.

FIGS. 90 and 91 illustrate a coiled balloon 1201 used for closing the internal opening of a fistula tract. The balloon 1201 is delivered in a coiled manner around the fistula tract 1104 (FIG. 90).

The balloon 1201 may be mounted in a rail of memory alloy or similar which assists in forming the spiral balloon shape, on deployment.

In one embodiment the balloon 1201 forms a straight coiled structure after delivery around the fistula tract.

In another embodiment the balloon 1201 forms a tapered coiled structure after delivery whereby the larger coil of the balloon is positioned deeper in the tissue than the narrow end.

The balloon 1201 may be delivered using a hollow delivery coil which locates the balloon in place. The balloon is then pushed out of the delivery coil and left in place.

Once in place, the balloon 1201 is inflated with saline, or other liquid or gas 1203 (FIG. 91). The effect of inflation is to compress the tissue surrounding the fistula tract 1202 thereby closing the internal opening of the fistula tract. This compression provides an effective seal against the pressures generated in the rectum and prevents passing faeces entering into the fistula tract, thus preventing re-infection.

The balloon may be comprised of a bioabsorbable material or similar. After a period of time corresponding to the healing of the fistula tract, the balloon material may degrade to a sufficient extent that the fluid with which it is filled (e.g. saline) is exposed to the tissue and is also absorbed. In time the entire balloon is absorbed.

The delivery mechanism may have a sharp tip to facilitate progression through the tissue.

The balloon may be dragged behind a coiled solid needle type delivery mechanism and detached to deploy the balloon.

In another embodiment the balloon is made from a non-bioabsorbable material, and is removed at an appropriate time frame post healing of the fistula tract.

The pressure to which the balloon is inflated may be variable. The balloon may be inflated to a pressure that corresponds to sufficient closing of the tract opening thereby overcoming the variability in delivery, anatomy and tract diameter.

A programmable electronic controller may be used to automatically inflate the balloon to the appropriate pressure.

Alternatively an analog or digital pressure gauge may be provided to indicate the balloon pressure to the clinician.

The activatable compressive element (balloon) may similarly be formed from a foam, pre formed structure (e.g. Nitinol cage or stent-like structure), or collapsible coil or other similar structure.

Figure 92:
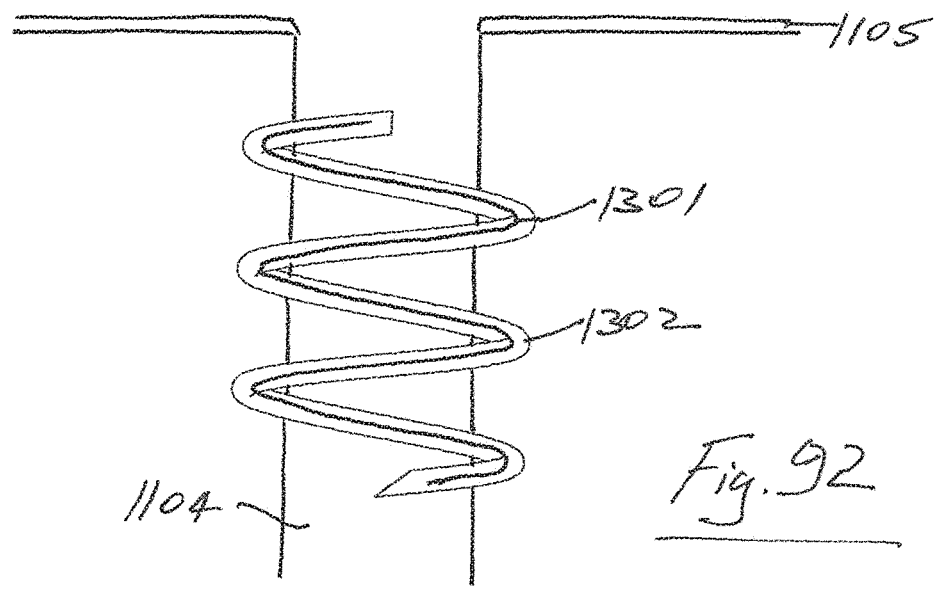
FIG. 92 is a diagram of a further fistula closure system of the invention in a delivery configuration.
Figure 93:
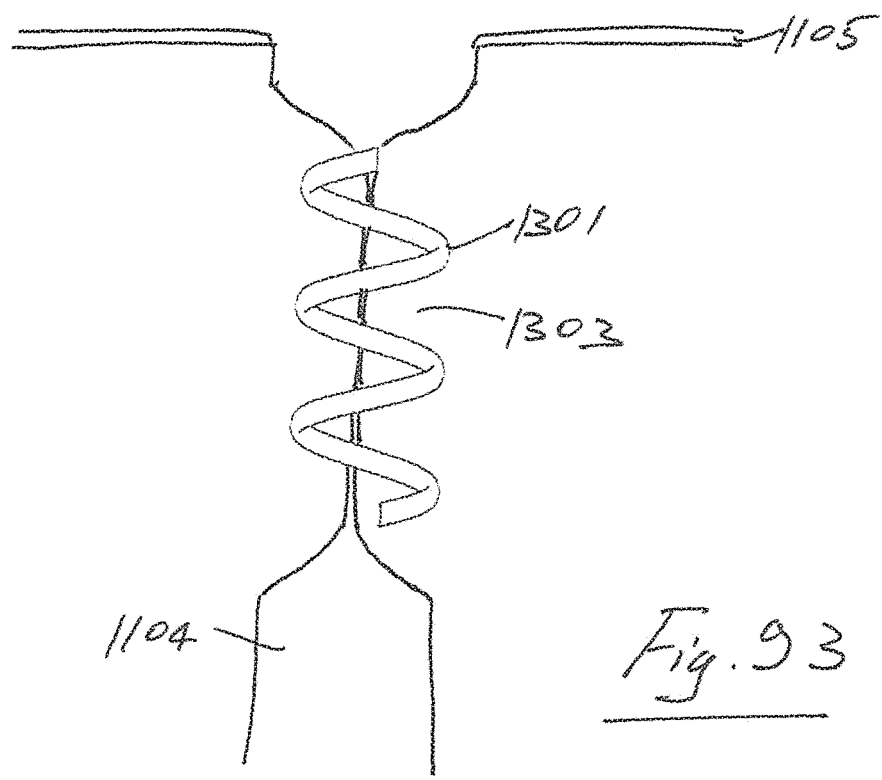
FIG. 93 shows the implant element of FIG. 92 in an activated configuration.

Referring to FIGS. 92 and 93 the implant element 1301 can be made from a shape memory material (Nitinol, shape memory polymer composite) activated by heat, light, electrical current or other energy source.

Once the implant element 1301 is delivered to the desired depth by an appropriate delivery/guide element 1302 (FIG. 92) the implant 1301 is activated by heat, light, electrical signal or other method, changing the state of the implant 1301 and activating the implant to be transformed to the compression state, thus compressing the tissue tract closed 1303 (FIG. 93). The patient's body heat may passively activate the implant to transform to the compressive state.

Figure 94:
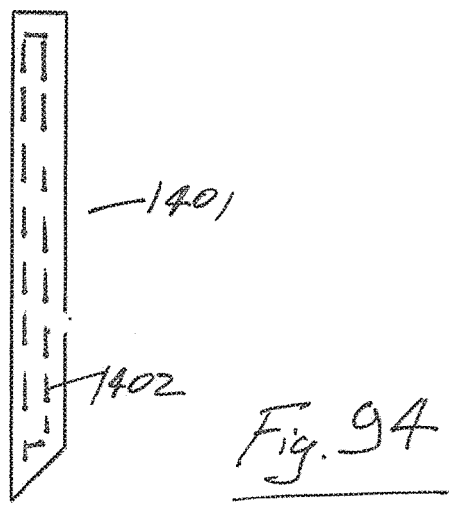
FIG. 94 is a diagram of an implant delivery system according to the invention.
Figure 95:
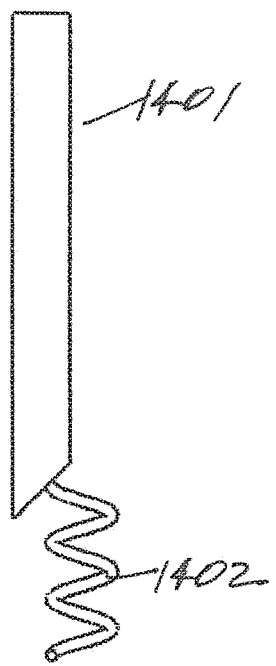
FIG. 95 shows an implant being delivered from the delivery tube of FIG. 94.

A compression coil may be delivered by placing a delivery tube 1401 a specified distance from the internal opening of the tissue tract (FIG. 94). Inside the tube an implant element 1402 is stowed. The delivery tube is inserted to the desired depth and the implant coil is forced out of the tube. As the implant coil exits the tube opening (FIG. 95) the successive diameters of the coil surround the tissue tract and compress the tissue resulting in closure of the tract.

Figure 96:
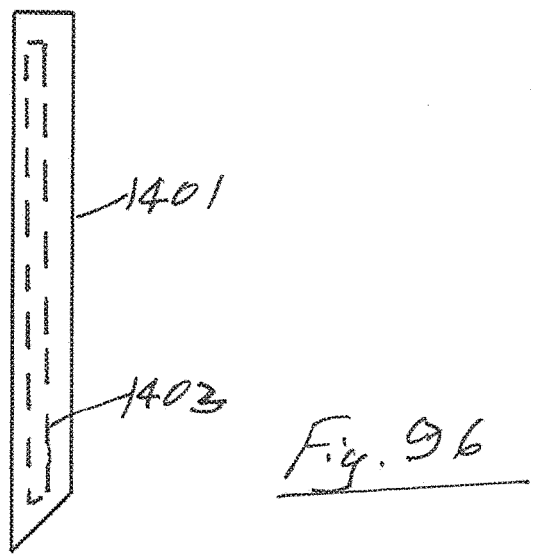
FIGS. 96 and 97 are views similar to FIGS. 94 and 95 of another implant element.
Figure 97:
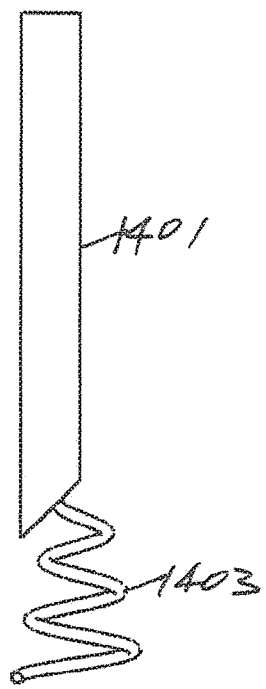

In another embodiment (FIGS. 96, 97) each additional coil of the implant element 1403 is smaller in diameter aiding in compressing the tract and achieving closure.

The coil can be made of a shape memory material. It is delivered as a straight coil and upon activation it compress the tissue tract.

Figure 98:
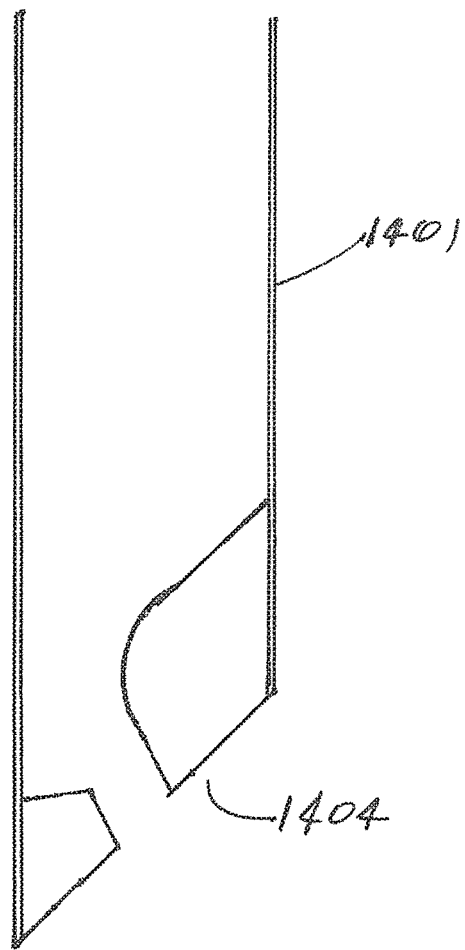
FIG. 98 is an enlarged view of a delivery system for another implant.
Figure 99:
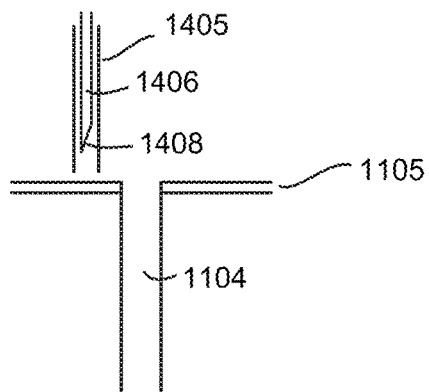
FIGS. 99 to 102 illustrate the deployment of another Implant element around a fistula.
Figure 100:
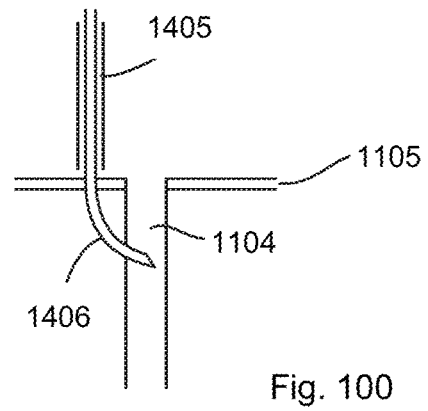
Figure 101:
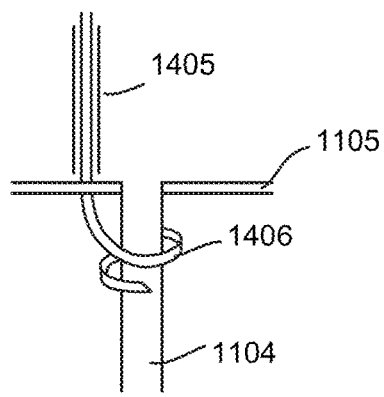
Figure 102:
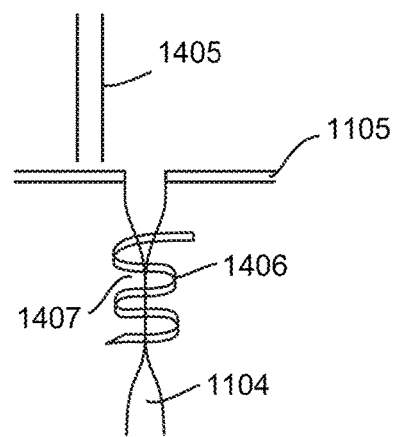
Figure 103:
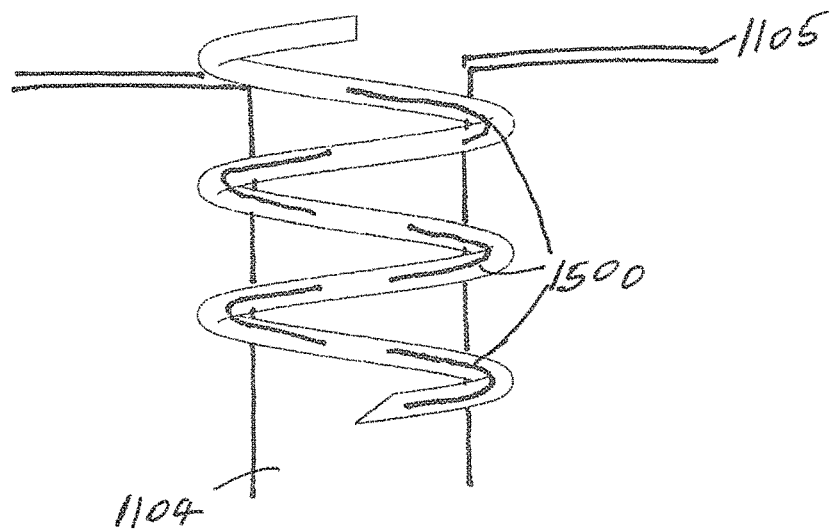
FIGS. 103 and 104 are diagrams of a further fistula treatment system according to the invention.

In another method, the implant material is not shape set and not of a shape memory material but is formed by a die built into the delivery tube (FIG. 98). As the coil exits the delivery tube and passes through the die 1404 the implant coil is formed on demand. The coils produced surround the tissue tract and compress the tract.

Referring to FIGS. 99 to 103 the implant element 1406 may also be delivered through a delivery mechanism 1405 located at the mucosal surface resulting in a 'winding' around the fistula tract tending to create a compression zone 1407 and resulting in closure of the tract. The implant may be preformed in a straight or tapered configuration. The implant element may have a sharp tip 1408 to facilitate progression through the tissue.

Figure 104:
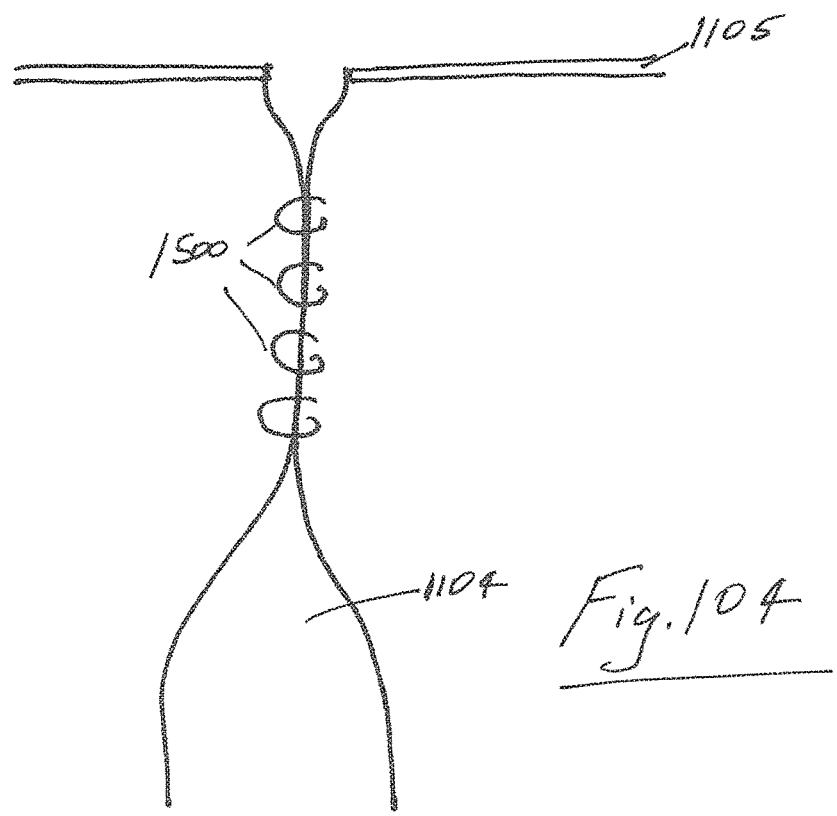

In some cases the implant may comprise a plurality of elements 1500. One such implant is illustrated in FIGS. 104 and 105. The multiple elements be delivered individually surrounding the fistula tract.

Each element may be preformed, or formed on delivery, or be activatable as previously described. The elements may be the same size in the preformed, or activated state. Alternatively the leading element may be larger in diameter and the following elements progressively smaller.

The clinician may determine the number of elements to deploy to attain adequate closure of the tract.

The device is capable of one or more of the following:
accommodating varied fistula tract physiology;
occluding and sealing the internal opening of the tract;
preventing faecal matter re-infecting the tract;
preserving sphincteric function;
enhancing fistula tract healing; and
facilitating drainage during healing.

The perianal fistula treatment device ensures sparing of the sphincter, occluding of the fistula tract internal opening, and promotion of drainage and tissue healing.

The anchoring and sealing mechanism of the device may consist of a tapered coil. The coil geometry is designed to pull tissue together as it is deployed into the sphincter muscle complex, resulting in a strong anchor but also, importantly, an effective compressive seal preventing reinfection of the fistula tract and close tissue approximation to enhance tissue healing.

The perianal fistula treatment device preserves sphincteric and anatomical conditions and functions, prevents re-fistulisation, and improves healing time over the current treatment methods. The implant closes the fistula internal opening by compressing the tract's surrounding tissue inwardly such that the tissue is brought within close approximation creating a seal impermeable to foreign materials and promoting tissue growth across the closely approximated fistula tract.

A drain may be used to provide a conduit to drain any abscess and remaining or newly formed exudate and fluids from the fistula tract throughout the time of the healing process. Such a drain or seton may be any of those described above.

The implant may be of any suitable shape in transverse cross section. For example, the implant cross-section may be round, oval, triangular, multifaced or ribbon-like. In some cases the implant may be hollow.

The implant may be intended for subsequent removal or may be bioabsorbable.

Typical materials for the implant include

Bioabsorbable magnesium (including MgFe and other magnesium alloys) would be a material of choice because it offers the strength of stainless steel and similar metals, yet is bioabsorbable. MgFe alloys are well studied and have been used in medical products.

PLA) and PLGA (poly(lactic-co-glycolic acid)) are bioabsorbable polymers and would be a material of choice as they are commonly used bioabsorbable materials and have been well studied and used in medical products for over 70 years.

The implant may also be constructed from other common materials used for suture applications A bioabsorbable implant would be beneficial to treatment of perianal fistulas due to the body's natural tendency to reject foreign materials.

The closure implant of the device may be maintained during the entire healing process. In some cases the implant remains in situ to withstand rectal pressures and maintain closure of internal tract opening for at least 10 weeks to prevent re-opening of the tract.

The implant may remain in place longer to allow full healing of the internal opening of the fistula tract.

The implant remains in place for a long enough period of time (e.g. greater than 1 week) to allow remodelling of the defect in the mucosa and formation of a mucosal layer. This mucosal layer acts as a bacterial seal preventing reinfection of the tract from entering of fasces. The reformation of the musical layer in conjunction with the sphincter muscle closure mechanism prevents fasces entering the tract.

The implant may be doped or loaded with healing and antimicrobial agents (such as stem cell, silver ions, silver particles, antibiotics, antibacterial agents and the like).

Modifications and additions can be made to the embodiments of the invention described herein without departing from the scope of the invention. For example, while the embodiments described herein refer to particular features, the invention includes embodiments having different combinations of features. The invention also includes embodiments that do not include all of the specific features described.

The invention is not limited to the embodiments hereinbefore described, which may be varied in construction and detail.

The invention claimed is:

1. A method of treating a perianal fistula with a helical implant having a proximal end and a distal end, the perianal fistula having an internal opening from the rectum, an external opening in an external surface of a buttocks, a fistula tract extending between the internal opening and the external opening, and fistula tissue surrounding the fistula tract, the method including:
engaging the distal end of the implant about the internal opening before the proximal end of the implant,
advancing the implant toward the external opening to compress fistula tissue via the implant, and
embedding the proximal end of the implant in the fistula tissue such that none of the implant is exposed to the rectum, the proximal end of the implant compressing the fistula tissue more than the distal end of the implant, and the implant sealing closed the internal opening of the fistula tract while leaving open the external opening of the fistula tract.

2. The method of claim 1, wherein the sealing includes sealing against pressure of up to 150 mmHg.

3. The method of claim 1, wherein the sealing includes sealing against pressure of up to 200 mmHg.

4. The method of claim 1, wherein the embedding of the proximal end of the implant includes embedding the implant below a mucosal lining and into a sphincter muscle complex.

5. The method of claim 1, further including locating a drain within the helical implant so that the compression of fistula tissue via the implant compresses tissue about the drain.

6. The method of claim 1, further including embedding a proximal end of a drain in a sphincter muscle complex, and a distal end of the drain protrudes through the external opening.

7. The method of claim 1, further including extending a drain through the fistula tract and using the drain to position the implant about the internal opening prior to advancing the implant.

8. The method of claim 1, wherein, following the compressing, a majority of the fistula tract remains open.

9. A method of treating a perianal fistula with an implant having a proximal end and a distal end, the perianal fistula having an internal opening from the rectum, an external opening in an external surface of a buttocks, a fistula tract extending between the internal opening and the external opening, and fistula tissue surrounding the fistula tract, the method including:
forming a perianal sinus by cinching closed the internal opening with the implant by advancing the implant distally through fistula tissue toward the external opening, wherein the implant tapers in a distal to proximal direction, and
drawing fistula tissue radially inwardly, wherein a first region of fistula tissue is drawn radially inwardly to a greater extent than at least a second region of fistula tissue, wherein the first region is closer to the internal opening than the second region.

10. The method of claim 9, wherein the forming the perianal sinus includes rotating the implant to embed the implant into bulk tissue of a sphincter muscle complex.

11. The method of claim 9, wherein the rotating of the implant includes advancing the proximal end of the implant to immediately past a mucosal lining of the rectum.

12. The method of claim 9, wherein the taper is defined by an outer surface of the implant.

13. The method of claim 9, further including positioning a drain within the fistula tract, wherein at least a portion of the drain extends from a location within the fistula tract and through the external opening.

14. The method of claim 13, further including embedding a proximal end of the drain in a sphincter muscle complex.

15. The method of claim 9, wherein the forming of the perianal sinus further includes forming a seal against pressure of up to 150 mmHg.

16. A method of treating a perianal fistula with an implant having a proximal end and a distal end, the perianal fistula having an internal opening from the rectum, an external opening in an external surface of a buttocks, a fistula tract extending between the internal opening and the external opening, and fistula tissue surrounding the fistula tract, the method including:
contacting the fistula tissue with the implant about the internal opening, wherein the implant includes a coil having a plurality of coil loops extending between the proximal end and the distal end, wherein at least a portion of the coil tapers in a distal to proximal direction along a length of the coil between the proximal end and the distal end;

rotating the implant into fistula tissue, distal end first, to advance the distal end of the implant toward the external opening, causing a diameter of at least a portion of the fistula tract to close via the tapered portion; and facilitating drainage through the external opening after the implant is in place.

17. The method of claim 16, further including compressing fistula tissue via the implant, wherein compressing includes progressively compressing fistula tissue such that a compression force imparted to fistula tissue via the distal end of the implant is less than a compression force imparted to fistula tissue via the proximal end of the implant.

18. The method of claim 16, further including, embedding the proximal end of the implant below a mucosal lining and into a sphincter muscle complex.

19. The method of claim 16, further including positioning a drain so that the closed portion of the fistula tract secures the drain, and at least a portion of the drain extends from the fistula tract and through the external opening.

20. The method of claim 19, wherein at least one of the implant or the drain are bioabsorbable.

21. The method of claim 20, wherein both of the implant and the drain are bioabsorbable, and wherein a rate of absorption of the drain is faster than a rate of absorption of the implant.

22. A method of closing a perianal fistula forming an opening in tissue comprising:

delivering a helical implant distally into tissue such that a plurality of helical loops of the implant pass through tissue surrounding the perianal fistula and compress tissue radially inwardly; and fixing a drain relative to the implant such that after the implant is delivered the drain extends from within the opening to a location outside of the opening, the drain being configured to facilitate fluid drainage from the opening along the drain, wherein fixing the drain relative to the implant includes compressing tissue radially inwardly about the drain.

23. The method of claim 22, further including drawing tissue around the opening radially inwardly toward a center of the implant, wherein a proximal region of tissue within the implant is drawn radially inwardly to a greater extent than a distal region of tissue within the implant.

24. The method of claim 22, wherein the implant comprises a tapered coil portion tapering toward a proximal end of the coil.

25. The method of claim 22, further including sealing closed only one end of the opening.

26. The method of claim 22, further including engaging a non-tapered distal section of a delivery device with an external surface of the implant.

27. The method of claim 22, further including advancing a proximal end of the implant below a mucosal lining and into a sphincter muscle complex.

28. A method of closing a perianal fistula in tissue, the fistula having an internal opening and an external opening, comprising:

delivering a helical implant distally into tissue such that a plurality of helical loops of the implant pass through tissue surrounding the perianal fistula and compress the tissue radially inwardly, wherein a proximal portion of the implant radially compresses the tissue more than a distal portion of the implant;

deploying the implant in an implanted position wherein a proximal end of the implant is completely embedded in the tissue; and fixing a drain relative to the implant such that, after the implant is delivered, the drain extends from within the fistula to a location outside of the external opening, the drain being configured to facilitate fluid drainage from the external opening along the drain.

29. The method of claim 28, wherein the embedding includes embedding the implant below a mucosal lining and into a sphincter muscle complex.

30. The method of claim 28, wherein the fixing of the drain includes compressing tissue about the drain as a result of the deployment of the implant.

* * * * *